United States Patent
Dower et al.

(10) Patent No.: US 6,309,842 B1
(45) Date of Patent: Oct. 30, 2001

(54) USE OF MODIFIED TETHERS IN SCREENING COMPOUND LIBRARIES

(75) Inventors: William J. Dower, Menlo Park; Christian M. Gates, Santa Cruz; Gregory L. Heinkel, San Jose; Guy Lalonde, Woodside; Larry C. Mattheakis, Cupertino; Christopher J. Paddon, Pacifica; Peter J. Schatz, Mountain View, all of CA (US)

(73) Assignee: Glaxo Wellcome Inc., Research Triangle Park, NC (US)

( * ) Notice: Subject to any disclaimer, the term of this patent is extended or adjusted under 35 U.S.C. 154(b) by 0 days.

(21) Appl. No.: 08/977,378

(22) Filed: Nov. 24, 1997

Related U.S. Application Data

(63) Continuation-in-part of application No. 08/758,307, filed on Dec. 3, 1996, now Pat. No. 5,958,703.

(51) Int. Cl.[7] .......................... G01N 33/53; G01N 33/543
(52) U.S. Cl. ..................... 435/7.1; 435/5; 435/6; 435/7.2; 435/7.21; 435/7.5; 435/DIG. 1; 435/DIG. 14; 435/DIG. 34; 536/23.1; 436/501; 436/518
(58) Field of Search ................................ 435/6, 7.1, 7.2, 435/5, 7.21, 7.5, 21, 23, 24, DIG. 1, DIG. 2, DIG. 14, DIG. 34, 501; 436/518; 536/23.1

(56) References Cited

U.S. PATENT DOCUMENTS

| | | |
|---|---|---|
| 4,766,075 | 8/1988 | Goeddel et al. . |
| 5,382,513 | 1/1995 | Lam et al. . |
| 5,401,629 | 3/1995 | Harpold et al. . |
| 5,436,128 | 7/1995 | Harpold et al. . |
| 5,565,324 | 10/1996 | Still et al. . |
| 5,635,598 * | 6/1997 | Lebl et al. . |
| 5,747,334 * | 5/1998 | Kay et al. . |
| 5,789,184 * | 8/1998 | Fowlkes et al. . |

FOREIGN PATENT DOCUMENTS

| | | | |
|---|---|---|---|
| 056443 A1 | 12/1992 | (EP) | ................................ C12Q/1/66 |
| WO 94/19461 | 9/1994 | (WO) | ............................ C12N/15/11 |
| WO 96/24061 | 8/1996 | (WO) | ............................ G01N/33/543 |
| WO 96/30392 | 10/1996 | (WO) | ............................ C07K/1/04 |
| WO 97/37220 | 10/1997 | (WO) | ............................ G01N/33/53 |

OTHER PUBLICATIONS

Frank R., Strategies and techniques in simultaneous solid phase synthesis based on the segmentatin of membrane type supports. Bioorganic and Med. Che, Lett. 3(3): 425–430, 1993.*

Barrett and Goldstein (1985), "A Monoclonal Antibody Specific for a Dynorphin Precursor," Neuropeptides 6:113–120.

Barrett et al. (1992), "Selective Enrichment and Characterization of High Affinity Ligands from Collections of Random Peptides on Filamentous Phage," Anal. Biochem. 204:357–364.

Bazan et al. (1994), "Platelet–activating Factor and Retinoic Acid Synergistically Activate the Inducible Prostaglandin Synthase Gene," Proc. Natl. Acad. Sci. USA 91:5252–5256.

Berke (1995), "The CTL's Kiss of Death," Cell 8:9–12.

(List continued on next page.)

Primary Examiner—Padmashri Ponnaluri
(74) Attorney, Agent, or Firm—Townsend & Townsend & Crew

(57) ABSTRACT

The invention provides methods for screening libraries of complexes for compounds having a desired property, especially, the capacity to agonize, bind to, or antagonize a cellular receptor. The complexes in such libraries comprise a compound under test, a tag recording at least one step in synthesis of the compound, and a tether susceptible to modification by a reporter molecule. Modification of the tether is used to signify that a complex contains a compound having a desired property. The tag can be decoded to reveal at least one step in the synthesis of such a compound.

4 Claims, 13 Drawing Sheets

OTHER PUBLICATIONS

Chen et al. (1995), "Tethered ligand library for discovery of peptide agonists," J. Biol. Chem. 270:23398–23401.

Cull et al. (1992), "Screening for Receptor Ligands Using Large Libraries of Peptides Linked to the C terminus of the lac Repressor," 89:1865–1869.

Gossen and Bujard (1992), "Tight Control of Gene Expression in Mammalian Cells by Tetracycline–responsive Promoters," Proc. Natl. Acad. Sci. USA 89:5547–5551.

Himmler et al. (1993), "Functional Testing of Human Dopamine $D_1$ and $D_5$ Receptors Expressed in Stable c–AMP–responsive Luciferase Reporter Cell lines," J. Receptor Res. 13(1–4):79–94.

Kinsella et al. (1991), "Molecular Cloning and Characterization of a Candida tsukubaensis α–Glucosidase Gene in the Yeast Saccharomyces cerevisiae," Curr. Genet. 20:45–52.

Kumar et al. (1992), "Saccharomyces cerevisiae Cells Secreting an Aspergillus niger β–galactosidase Grown on Whey Permeate," Biotech. 10:82–85.

Martens et al. (1995), "Peptides Which Bind to E–selectin and Block Neutrophil Adhesion," J. Biol. Chem. 270:21129–21136.

Miller (1972), "Experiment 33, Penicillin and Ampicillin Treatment for the Isolation of Auxotrophic Mutants,"in Experiments in Molecular Genetics, Cold Spring Harbor Laboratory 33:230–234.

Moreira et al. (1992), "Evaluation of Reporter Genes in Mammalian Cell Lines," Methods in Molecular and Cellular Biology 3:23–29.

Normie (1996), "System Uses Photonics for Early Tumor Detection," Biophotonics News, Sep./Oct., pp. 24–25.

Paravicini et al. (1992), "The Osmotic Integrity of the Yeast Cell Requires a Functional PKC1 Gene Product," Mol. Cell Biol. 12:4896–4905.

Price et al. (1995), "Funtional Coupling of a Mammalian Somatostatin Receptor to the Yeast Pheromone Response Pathway," Mol. Cell. Biol. 15:6188–6195.

Schatz (1993), "Use of Peptide Libraries to Map the Substrate Specificity of a Peptide–Modifying Ezyme: A 13 Residue Consensus Peptide Specifies Biotinylation in Escherichia coli," Biotech. 11:1138–1143.

Schneider et al. (1996), "An In Vitro Assay of β–Galactosidase from Yeast," BioTechniques 20:960–962.

Smith et al. (1995), "Rapid identification of highly active and selective substrates for stromelysin and matrilysin using bacteriophage peptide display libraries," J. Biol. Chem. 270:6440–6449.

Vallette et al. (1995), "Unsaturated Fatty Acids Synergisticaly Enhance Glucocorticoid–induced Gene Expression," Cellular Signalling 7:319–323.

Whitehorn et al. (1995), "A Generic Method for Expression and Use of "Tagged" Soluble Versions of Cell Surface Receptors," Bio/Technology 13:1215–1218.

Wrighton (1991), "Use of Tissue–Plasminogen Activator as a Reporter Gene," Chapter 16 of Methods in Molecular Biology, vol. 7: Gene Transfer and Expression Protocols, E.J. Murray, ed., The Humana Press Inc., Clifton, NJ, pp. 209–215.

Yamauchi et al. (1993), "Phosphatidylinositol 3–Kinase Functions Upstream of Ras and Raf in Mediating Insulin Stimulation of c–fos Transcription," J. Biol. Chem. 268:14597–14600.

Zaworski and Gill (1990), Use of Saccharomyces cerevisiae Expressing β–Galactosidase to Screen for Antimycotic Agents Directed against Yeast Cell Wall Biosynthesis and Possible Application to Pathogenic Fungi, in Molecular Biology Research, Upjohn Company, Kalamazoo, Michingan, 34:660–662.

Zuckermann et al. (1994), "Discovery of Nanomolar Ligands for 7–Transmembrane G–Protein Coupled Receptors from a Diverse N–(Substituted)glycine Peptoid Library," J. Med. Chem. 37:2678–2685.

Clontech Product Report, "Reporter Assays & Vectors 26," pp. 161–164.

Corning Product Report, "Fotoform®: a material and a capability."

Pharmacia Biotech Product Report, "Instructions Cytodex®1, Cytodex 2, Cytodex 3."

Tropix Product Report, "Phospha–Light™."

Felder et al. (1996), "A new combination of protecting groups and links for encoded synthetic libraries suited for consecutive tests on the solid phase and in solution," Molecular Diversity 1(2):109–112.

Needels et al. (1993), "Generation and screening of an oligonucleotide–encoded synthetic peptide library," Proc. Natl. Acad. Sci. USA 90:1007–10704.

* cited by examiner

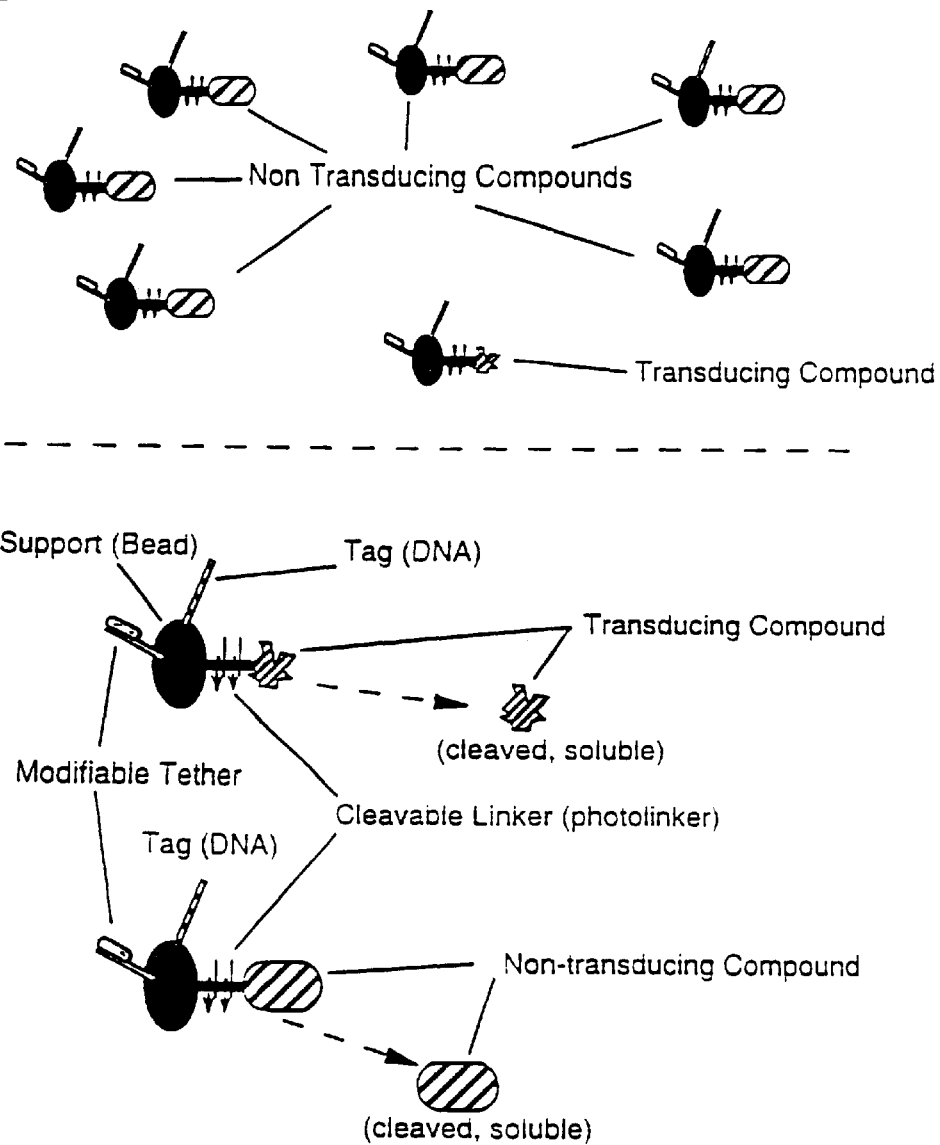

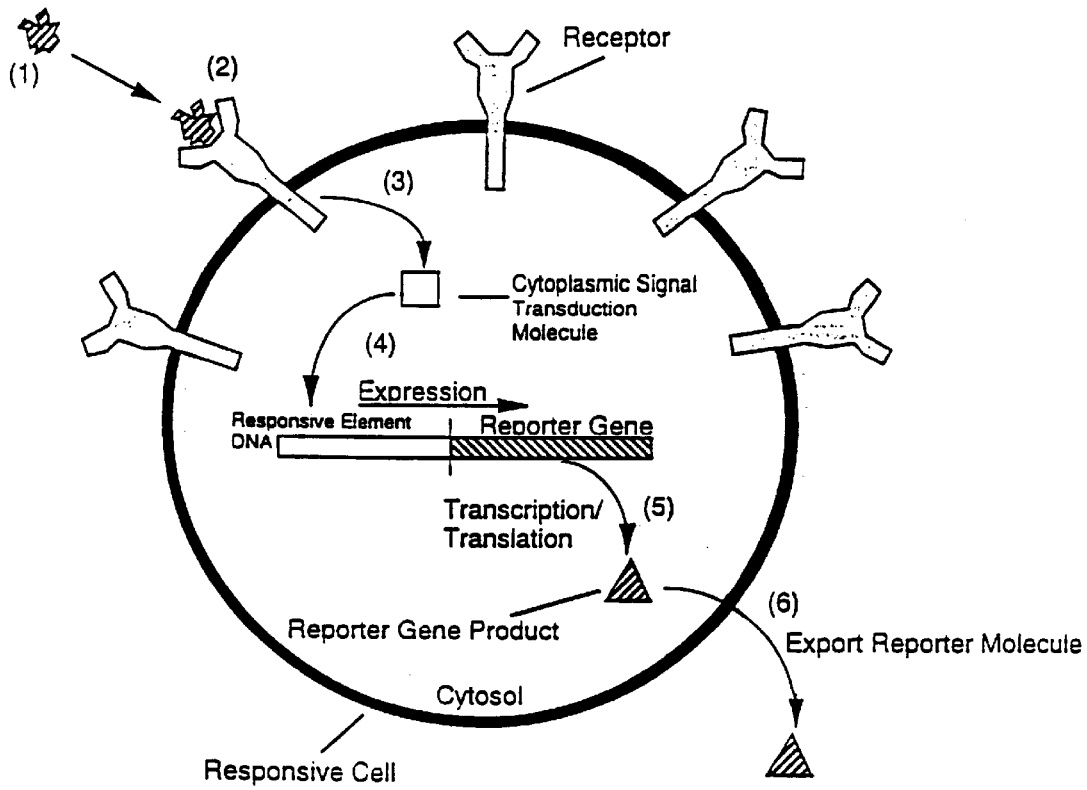

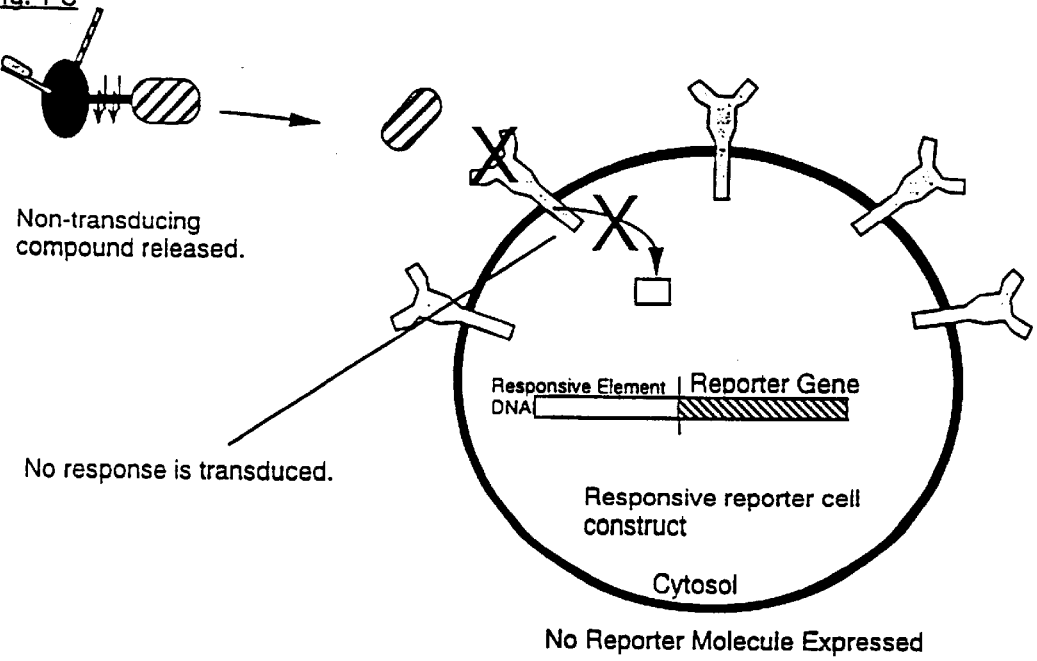
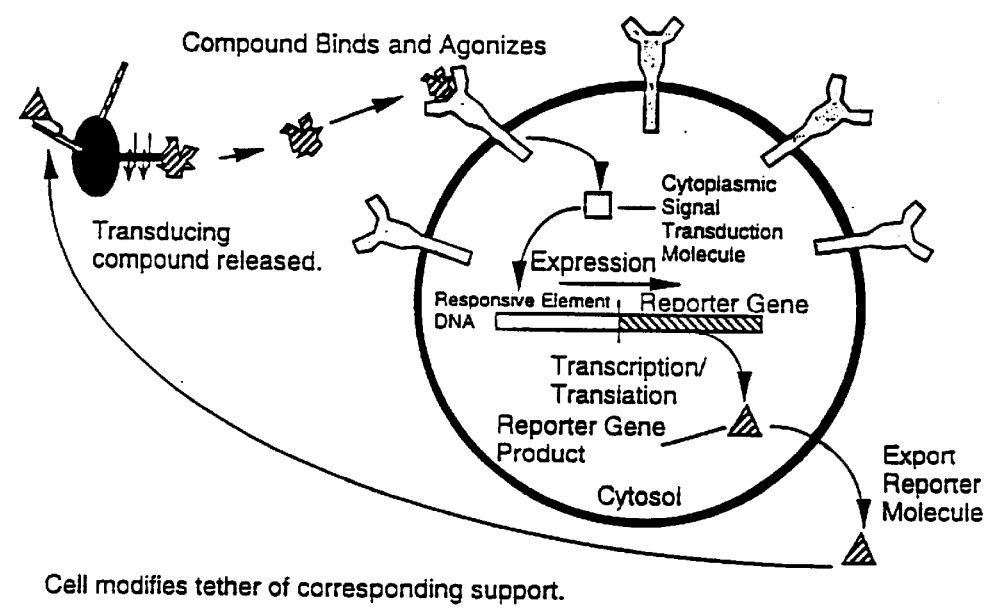
Fig. 1 C

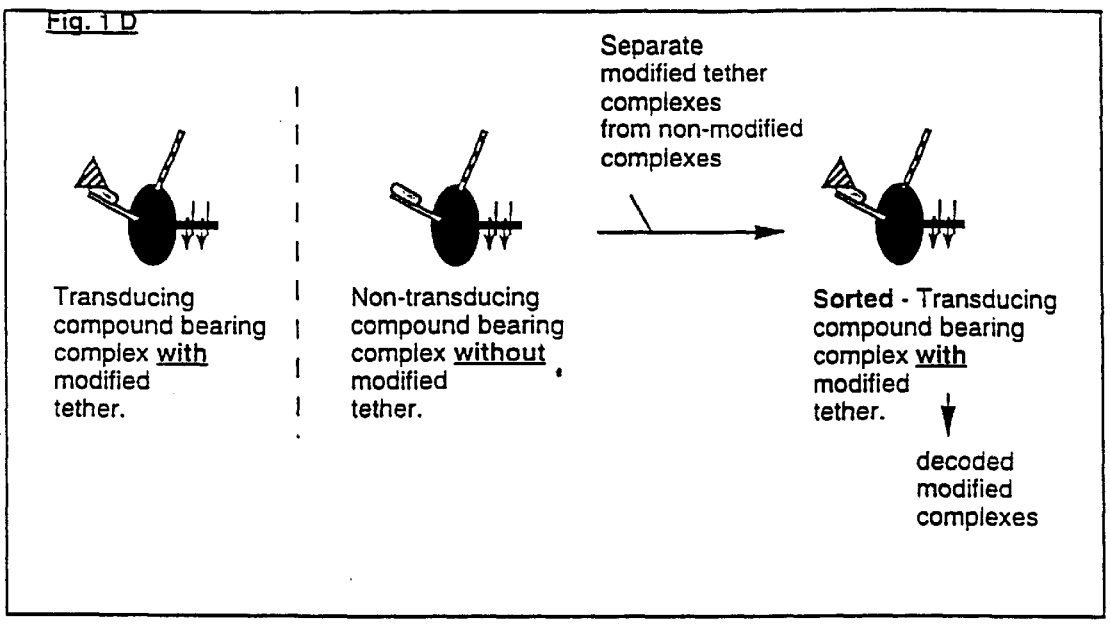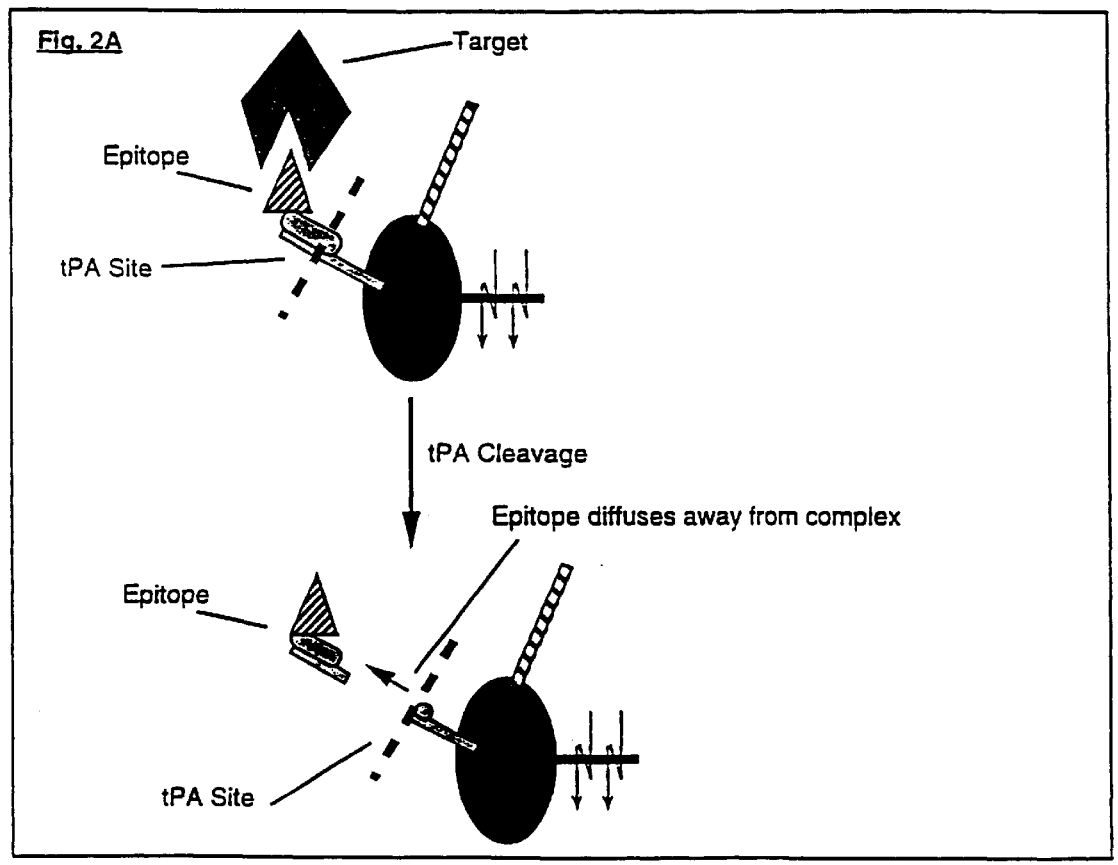

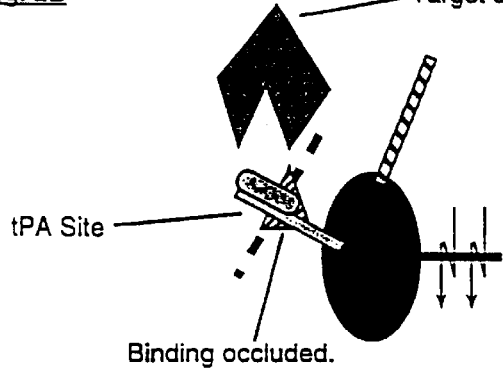
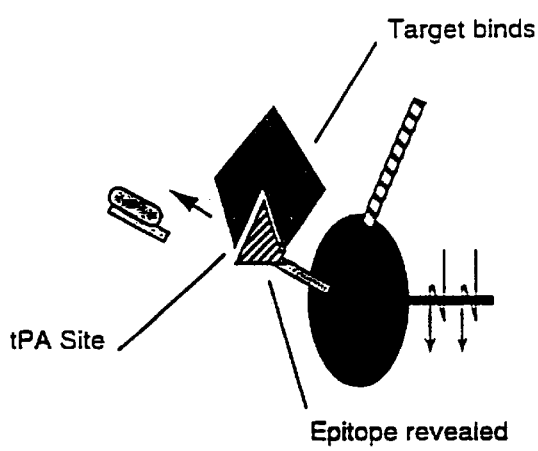
Fig. 2B

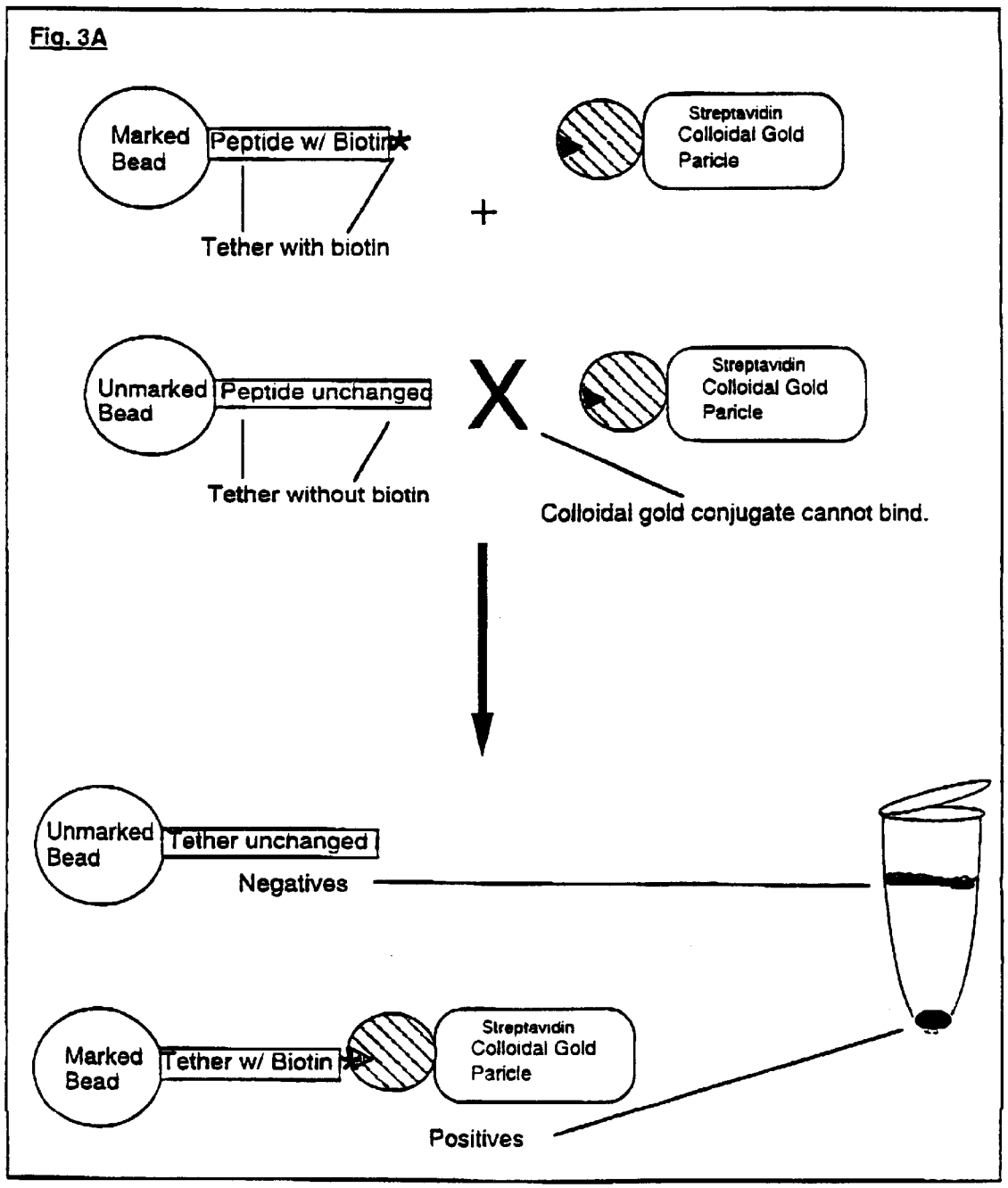

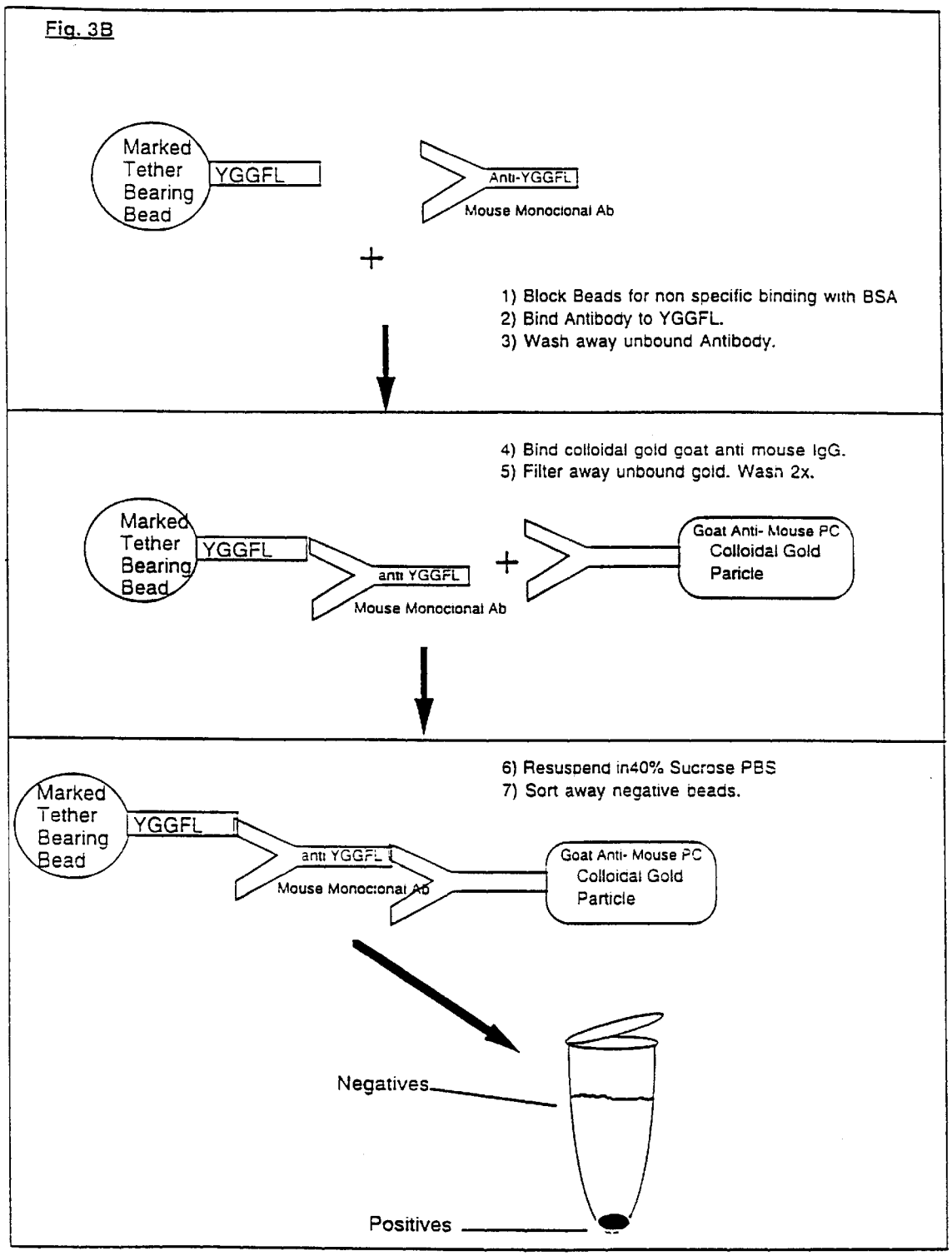

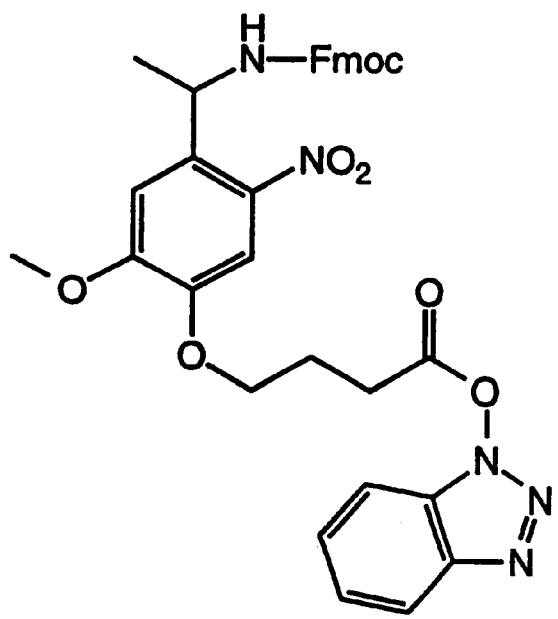
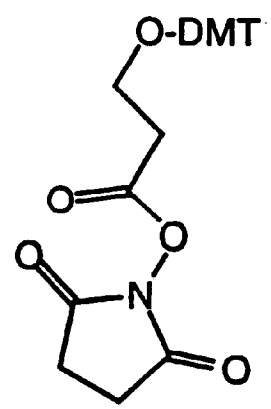
1           2
Fig. 8

USE OF MODIFIED TETHERS IN SCREENING COMPOUND LIBRARIES

CROSS-REFERENCE TO RELATED APPLICATION

This application is a continuation-in-part of U.S. Ser. No. 08/758,307, filed Dec. 3, 1996, now U.S. Pat. No. 5,958,703, which is incorporated by reference in its entirety for all purposes.

TECHNICAL FIELD

The invention applies the technical fields of combinatorial chemistry and molecular genetics to the identification of compounds with desired properties, such as capacity to bind to, agonize or antagonize a cellular receptor.

BACKGROUND OF THE INVENTION

Several methods have been reported for producing and screening large libraries to identify compounds having specific affinity for a target. These methods include the phage-display method in which randomized peptides are If displayed from phage and screened by affinity chromatography to an immobilized receptor. See, e.g., Dower et al., WO 91/17271; McCafferty et al., WO 92/01047; Ladner, U.S. Pat. No. 5,223,409 (incorporated by reference in their entirety for all purposes). In another approach, combinatorial libraries of polymers immobilized on a chip are synthesized using photolithography. See, e.g., U.S. Pat. No. 5,143,854; WO 90/15070 and WO 92/10092. The immobilized polymers are contacted with a labelled receptor and scanned for label to identify polymers binding to the receptor.

A general, and particularly useful, method for synthesizing and screening large libraries of compounds is the encoded synthetic library method (ESL) of Dower et al. In this method, the different compounds in the library are usually synthesized attached to separate supports (e.g., beads) by stepwise addition of the various components of the compounds in several rounds of coupling. A round of coupling can be performed by apportioning the supports between different reaction vessels and adding a different component to the supports in the different reaction vessels. The particular component added in a reaction vessel can be recorded by the addition of a tag component to the support at a second site. After each round of synthesis, supports from the same reaction vessel can be apportioned between different reaction vessels and/or pooled with supports from another reaction vessel in the next round of synthesis. In any, and usually in all rounds of synthesis, the component added to the support can be recorded by addition of a further tag component at a second site of the support. After several rounds of synthesis, a large library of different compounds is produced in which the identities of compounds are encoded in tags attached to the respective supports bearing the compounds. The library can be screened for binding to a target. Supports bearing compounds having a specific affinity for the target are isolated, and the identity of such compounds can be determined by decoding the tags.

All of the above methods have proved successful in isolating compounds having specific affinity for a target of interest. For example, the methods have been used to isolate compounds that bind to a cellular receptor for use as antagonists of receptor-ligand interactions. However, the repertoire of compounds that can be identified by some of the above methods is somewhat limited by the fact that compounds are screened in a tethered format. Furthermore, existing screening methods generally have not been used to distinguish between compounds that merely bind to a receptor, and compounds that are capable of transducing a biological signal through the receptor. The latter compounds are expected to have particularly useful properties, such as the capacity to agonize normal ligand-receptor interactions. These properties can be exploited in many applications such as stimulation of cell or tissue growth, and enzyme, growth factor or hormone replacement therapy.

The present invention provides methods for screening compounds for capacity to transduce a signal through a cellular receptor, thereby allowing the isolation of novel pharmaceuticals.

SUMMARY OF THE INVENTION

The invention provides methods for screening libraries of compounds for a desired activity. In many of the methods, a library of complexes is produced in which each complex comprises a compound under test, a tag recording at least one step in the synthesis of the compound, and a tether susceptible to modification by a reporter molecule. One or more, but not all, of the complexes have a tether that has been modified by the reporter enzyme, the modification indicating that the one or more complexes bear compound(s) having the desired property. At least one complex having a modified tether is separated from the library by virtue of the modified tether. The tag of the complex having the modified tether is then decoded to identify at least one step in the synthesis of a compound having the desired property.

In one aspect, the invention provides methods of screening compounds for capacity to transduce a signal through a cellular receptor. The methods entail providing a plurality of complexes, each complex comprising a compound under test, a tag recording at least one step in synthesis of the compound, and a tether susceptible to modification by a reporter molecule. The complexes are contacted with cells having a receptor and a DNA segment encoding the reporter molecule. At least one compound transduces a signal through the receptor of a cell causing release of reporter molecule expressed from the DNA segment from the cell. The complex having the modified tether is then isolated. The tag of this complex identifies at least one step in the synthesis of the compound transducing the signal.

Optionally, complexes comprise compounds linked to supports by a photocleavable linker and the compounds are freed from the supports by exposure to radiation to allow free compounds to diffuse into contact with cellular receptors. Examples of compounds that can be screened include polypeptides, beta-turn mimetics, polysaccharides, phospholipids, hormones, prostaglandins, steroids, aromatic compounds, heterocyclic compounds, benzodiazepines, oligomeric N-substituted glycines and oligocarbamates. One class of receptor of interest for screening compounds for transducing activity are G-protein coupled receptors. Often, compounds are contacted with supports in a medium that limits diffusion of released reporter, such as a gel matrix. The selection of tether and reporter molecule are interdependent; for example, in one format, the reporter molecule is a protease and the tether bears a site for the protease. In a variation, a second reporter molecule is induced by signal transduction, and the second reporter molecule modifies or induces the reporter molecule which modifies the tether.

In a further variation, the cells further comprise a second DNA segment encoding a site-specific recombinase, and the DNA segment contains a gene encoding the reporter molecule, which gene is disrupted by an inactivating sequence flanked by sites recognized by the site-specific recombinase. The transducing compound causes expression of the site-specific recombinase, which excises the inactivating sequence from the gene resulting in expression of the reporter molecule, which is released from the cell and modifies the tether of the complex from which the compound was released.

In a second aspect, the invention provides additional methods for screening compounds for capacity to transduce a signal through a cellular receptor. In these methods, a plurality of supports are provided, each support bearing a compound under test, and a tether susceptible to modification by a reporter molecule, however, the supports need not have tags. The supports are contacted with cells having a receptor and a DNA segment encoding the reporter molecule. The compounds are partially freed from the supports, whereby at least one compound transduces a signal through the receptor of a cell causing expression of the reporter molecule, which reporter molecule is released from the cell and modifies the tether of the support from which the compound transducing the signal was partially freed. The support having the modified tether is isolated, which support bears the compound transducing the signal.

In another aspect, the invention provides a further method for screening compounds for capacity to transduce a signal through a cellular receptor. In these methods, compounds are provided as an array on a membrane. The membrane is contacted with cells having a receptor and a DNA segment encoding a reporter molecule. At least one compound transduces a signal through the receptor of a cell causing expression of the reporter molecule, which reporter molecule is released from the cell and modifies the membrane at a position proximate to the compound transducing the signal. The modification allows the compound transducing the signal to be isolated. The array of compounds can be provided as an array of cells, each producing a compound under test. For example, the compounds may be secondary metabolites.

In another aspect, the invention provides still further methods of screening compounds for capacity to transduce a signal through a cellular receptor. The methods entail providing a collection of cells, each secreting a compound under test and each bearing a tether on its surface. The collection of cells is contacted with reporter cells having a receptor and a DNA segment encoding a reporter molecule; whereby at least one compound transduces a signal through the receptor of a reporter cell causing expression of the reporter molecule, which reporter molecule is released from the reporter cell and modifies the tether of the cell from the collection of cells secreting the compound that transduced the signal. The cell having the modified tether is isolated, wherein the compound transducing the signal is isolated by culturing the cell.

In another aspect, the invention provides methods of screening compounds for capacity to inhibit enzymatic modification of a substrate. The methods comprise providing a plurality of complexes, each complex comprising a compound under test, a tag recording at least one step in synthesis of the compound, and a tether susceptible to modification by an enzyme. The complexes are contacted with the enzyme and the compounds are released from the complexes within a matrix that retains a released compound in proximity to the complex from which it was released, whereby the enzyme modifies the tether of complexes from which compounds lacking enzyme inhibiting activity were released without modifying the tether of at least one complex from which a compound having enzyme inhibiting activity was released due to protection of the tether by the compound. At least one complex is isolated having the unmodified tether, wherein the tag of the complex identifies at least one step in the synthesis of the compound with inhibiting activity.

The invention further provides methods of screening compounds for capacity to bind to a receptor. The methods comprise providing a plurality of first complexes, each first complex comprising a compound under test, a tag recording at least one step in synthesis of the compound, and a tether susceptible to modification by a reporter molecule. The first complexes are then contacted with second complexes comprising a ligand specifically bound to the receptor, whereby either the ligand or receptor is immobilized to a support and the other is linked to a reporter molecule, whereby at least one compound competitively dissociates the ligand and the receptor, thereby allowing the linked reporter molecule to modify the tether of the first complex comprising the compound that competitively dissociates the ligand and the receptor. The first complex having the modified tether is then isolated. The tag of the complex identifies at least one step in the synthesis of the compound that competitively dissociates the ligand and the receptor.

In another aspect, the invention provides methods of screening compounds for capacity to antagonize a ligand of a cellular receptor. The methods comprise providing a plurality of complexes, each complex comprising a compound under test, a tag recording at least one step in synthesis of the compound, and a tether susceptible to modification by a reporter molecule. The complexes are contacted with cells and the ligand, wherein the cells have a receptor, a first DNA segment encoding the reporter molecule and a second DNA segment encoding a lethal gene whose expression is induced when the ligand binds to the receptor. In cells proximate to a complex bearing a compound that is an antagonist, the antagonist blocks signal transduction by the ligand through the receptor, the reporter molecule is expressed-and released from the cell, where it modifies the tether of the complex from which the compound was released. In cells proximate to complexes bearing compounds that are not antagonists, the ligand transduces a signal through the receptor of a cell causing expression of the lethal gene, the cells die, and the tethers of the complexes bearing compounds that are not antagonists remain unmodified. The complex having the modified tether is isolated. The tag of the complex identifies at least one step in the synthesis of the compound transducing the signal.

BRIEF DESCRIPTION OF THE FIGURES

FIG. 1: Scheme for screening a library of complexes bearing compounds, tags and tethers for compounds having transducing activity. (A) The upper panel shows a library of complexes. Most complexes bear nontransducing compounds. The lower panel shows cleavage of compounds from the complexes. Both transducing and nontransducing compounds are cleaved. (B) A transducing compounds binds to a cellular receptor and transduces a signal resulting in expression of a reporter gene and export of a reporter molecule from the cell. (C) The lower part of the figure shows the reporter molecule modifying the tether of complex from which the compound transducing the signal was released. The upper part of the figure shows that the tethers of complexes lacking transducing compounds remain unmodified. (D) Complexes bearing modified tethers are separated from complexes bearing unmodified tethers. Tags of complexes bearing modified tethers can then be decoded to reveal the identity of transducing compounds.

FIG. 2: Schemes for modification of a tether that allow separation of modified and unmodified tethers. (A) Cleavage of the tether by a protease, such as tPA, releases an epitope and the tether loses capacity to bind a target. (B) Cleavage of the tether produces a free end required for target binding.

FIG. 3: Schemes for separation of marked and unmarked supports using dense metal labelled receptor. (A) Tether modified by biotin. (B) Tether modified (SEQ ID NO:1) to acquire binding site for an antibody.

FIG. 8: Linkers for attachment of compounds (1) and DNA tags to supports (2).

DEFINITIONS

Figure 4:
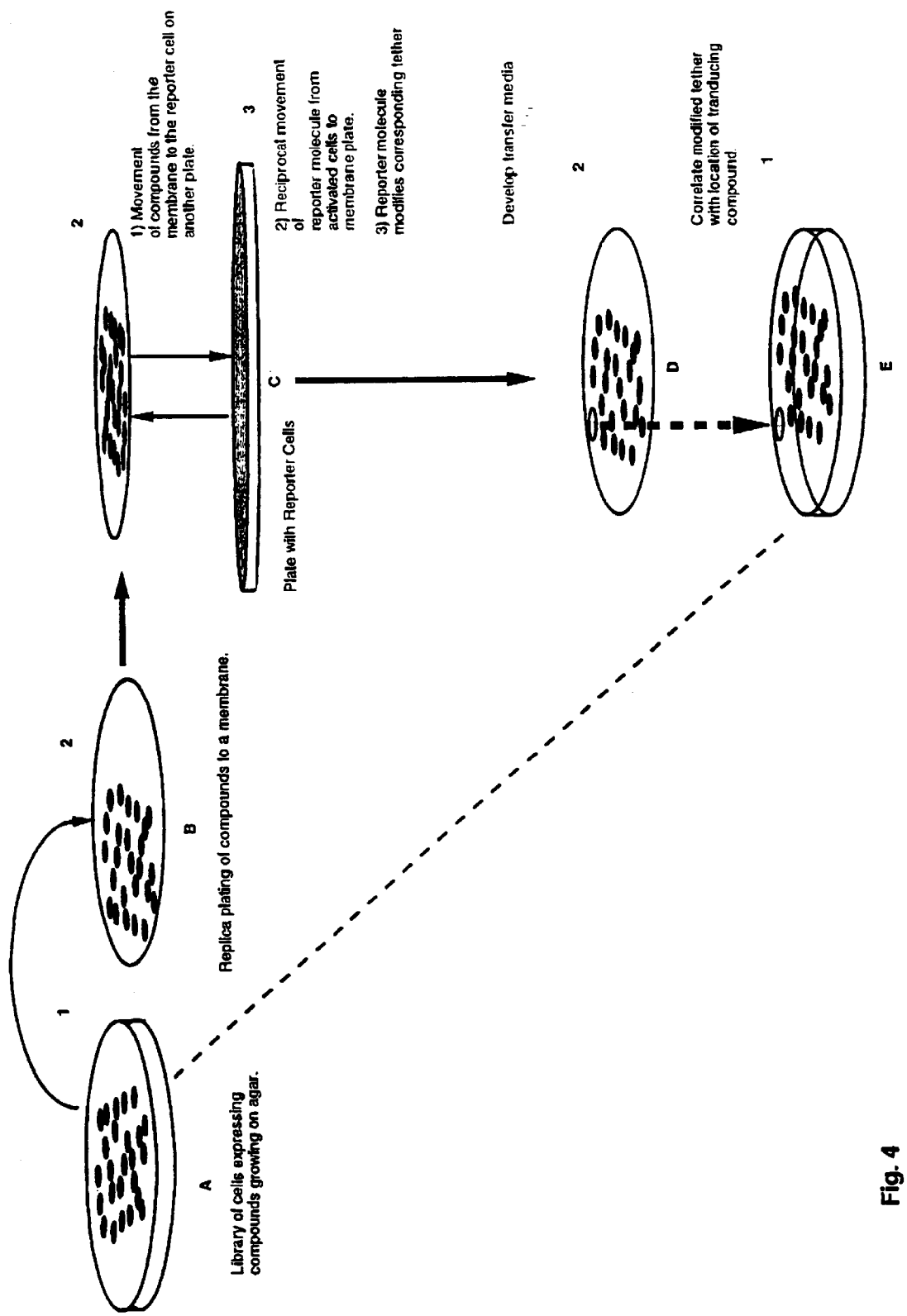
FIG. 4: Scheme for screening a library of cells producing compounds for transducing activity.

A DNA segment is operably linked when placed into a functional relationship with another DNA segment. For example, DNA for a signal sequence is operably linked to DNA encoding a polypeptide if it is expressed as a preprotein that participates in the secretion of the polypeptide; a promoter or enhancer is operably linked to a coding sequence if it stimulates the transcription of the sequence. Generally, DNA sequences that are operably linked are contiguous, and in the case of a signal sequence both contiguous and in reading phase. However, enhancers need not be contiguous with the coding sequences whose transcription they control. Linking is accomplished by ligation at convenient restriction sites or at adapters or linkers inserted in lieu thereof.

A library member is isolated from a library if it exists in substantially enriched form in a subpopulation of the library. Library members having desired activity are usually further isolated to homogeneity.

DETAILED DESCRIPTION

I. Methods of Screening Encoded Libraries

The invention provides methods for screening libraries of different compounds to identify particular compounds capable of transducing a signal through a biological receptor. The general principles of some of these methods are exemplified by the scheme shown in FIG. 1 (panels A–E). Panel A illustrates a library of compounds to be screened. In this example, the library members are complexes comprising a support with three entities attached, a compound to be screened, a tag (which serves to identify the compound or components thereof), and a tether. Such a library is similar to the ESL libraries described by Dower et al., supra except for the tether in the present libraries. Panel B shows the type of cell used in screening the libraries (i.e., a reporter cell). A reporter cell has a receptor and a reporter construct capable of being expressed when the receptor is stimulated.

Panel C shows the complexes in the library being contacted with reporter cells. After mixing of complexes and reporter cells, the compounds being screened are usually cleaved from their respective complexes. After cleavage, the compounds diffuse into contact with the cellular receptors. Some of the compounds are able to transduce a signal through a receptor, thereby inducing transcription and expression of the reporter construct to produce a reporter molecule, as shown in the lower half of the panel. The reporter molecule is secreted or otherwise released from the cell, where it comes into contact with the complex from which the compound transducing the signal was released. The reporter molecule then modifies the tether of this complex. Thus, after this series of events, the complex which originally bore a transducing compound appears as shown at the left side of panel D. The complex now has a tag, what remains of the linker following cleavage of the compound being screened from the complex, and a modified tether.

Nontransducing compounds do not cause reporter molecules to be released from adjacent report cells (see upper half of panel C). Thus, the respective complexes from which such compounds derived appear as shown in the right of panel D. The complexes have a tag, what remains of the linker following cleavage of the compound to be screened, and an unmodified tether.

Supports having modified tethers are separated from supports having unmodified tethers. Although it is known that the supports having modified tethers once bore transducing compounds, these compounds are no longer attached. Nevertheless, the identity of these compound can be determined by decoding the tags attached to the supports. Compounds having capacity to transduce a signal can then be resynthesized based on the information from the tags.

1. Library Construction
   a. ESL Libraries

The construction of encoded synthetic libraries (ESL) has been described in Affymax, WO 95/12608, Affymax, WO 93/06121, Columbia University, WO 94/08051, Pharmacopeia, WO 95/35503 and Scripps, WO 95/30642 (each of which is incorporated by reference for all purposes) and summarized in the Background Section above. The ESL method for synthesizing compounds typically involves a random combinatorial approach and the chemical and/or enzymatic assembly of monomer units. For example, the method typically includes steps of: (a) apportioning a plurality of solid supports among a plurality of reaction vessels; (b) coupling to the supports in each reaction vessel a first monomer and a first tag using different first monomer and tag combinations in each different reaction vessel; (c) pooling the supports; (d) apportioning the supports among a plurality of reaction vessels; (e) coupling to the first monomer a second monomer and-coupling to either the solid support or to the first tag a second tag using different second monomer and second tag combinations in each different reaction vessel; and optionally repeating the coupling and apportioning steps with different tags and different monomers one to twenty or more times. The monomer set can be expanded or contracted from step to step; or the monomer set could be changed completely for the next step (e.g., amino acids in one step, nucleosides in another step, carbohydrates in another step). A monomer unit for peptide synthesis, for example, can include single amino acids or larger peptide units, or both. The size of libraries generated by such methods can vary from 2 different compounds to $10^2$ $10^4$, $10^6$, $10^8$, $10^{10}$, $10^{12}$ or $10^{15}$.

Supports can be of any shape, although they are often roughly spherical. The supports need not necessarily be homogenous in size, shape, or composition; although the supports usually are uniform. The supports can be a single particle, or two or more linked particles. The latter arrangement allows the segregation of molecules or oligomers and identifier tags into discrete "zones" and permits the use of widely different chemically reactive groups and chemistries for attachment. Optionally, libraries can be formed without solid supports in which compounds are joined to tags via linkers.

Supports can consist of many materials, limited primarily by capacity for derivatization to attach any of a number of chemically reactive groups and compatibility with the chemistry of oligomer or other molecular synthesis and tag and tether attachment. Suitable support materials include solids such as glass, latex, heavily cross-linked polystyrene or similar polymers, gold or other colloidal metal particles. Such solid supports are derivatized with chemical groups typical for solid state synthesis of the intended compounds. In general, the solid support size is in the range of 1 nm to 100 $\mu$m, but a more massive solid support of up to 1 mm in size may sometimes be used. Monobeads™ (10 $\mu$m) (Pharmacia Fine Chemicals AB, Uppsala Sweden) or their equivalent, are particularly useful as solid supports.

Compounds screenable by the present methods include, for example, peptides, oligonucleotides, oligo N-substituted glycines, and polycarbamates. Other compounds include polymers formed from one or more of the following monomer types: amino acids, carbamates, sulfones, sulfoxides, nucleosides, carbohydrates, ureas, phosphonates, lipids, esters. Other compounds that can be synthesized in a component-by-component fashion can also be screened including benzodiazepines, hydantoins, and peptidylphosphonates (see U.S. Ser. No. 08/119,700, filed Sep. 9, 1993, and U.S. Pat. No. 5,339,115, each of which is incorporated herein by reference).

The identifier tags identify reaction steps that an individual compound has experienced. For syntheses proceeding to high yield and effectively generating single products (e.g., peptide and oligonucleotide synthesis), the tag explicitly specifies one, and usually all, of the components of the product, and the resulting product structure. In some situations, for example, when only a small number of monomer units of an oligomer are varied, one may need to identify only those monomers which vary among the oligomers. For other syntheses giving variable yields and frequently multiple products (such as regio- and stereoisomeric structures), a mixture of compounds is sometimes obtained on each support. In this situation, the tag may not uniquely specify the chemical structure of an associated entity. Rather, the tag encodes the synthetic protocol (e.g., reagents and reaction conditions) by which a member of the library was constructed. The library is screened to identify "active recipes" that then can be reproduced on a preparative scale and fractionated (if necessary) to isolate the bioactive component(s).

The tags can be attached immediately before, during, or after a round of monomer addition to compounds or other reaction, as compatible with the type of identifier tag, modes of attachment, and chemistry of oligomer or other molecular synthesis. The code can be contained in a single polymeric sequence of individual tags or can be embodied by the presence or absence of individual different tags on the support.

The identifier tag has a recognizable feature that is, for example, microscopically or otherwise distinguishable in shape, size, mass, charge, or emissions. This recognizable feature may arise from the spectral, chemical, electronic, or magnetic properties of the tag, or from some combination of such properties. In essence, the tag serves to label a molecule and to encode information decipherable at the level of one (or a few) molecules or solid supports. By using identifier tags to track the synthesis pathway that each member of a chemical library has taken, one can deduce the structure of any chemical in the library (i.e., the sequence of monomers of any oligomer) by reading the identifier tag.

One can construct microscopically identifiable tags as small beads of recognizably different sizes, shapes, or colors, or labeled with bar codes. The tags can be machine-readable luminescent or radioactive labels. The identifier tag can also be an encodable molecular structure. The information may be encoded in the size (the length of a polymer) or the composition of the molecule.

Oligodeoxyribonucleotides are one form of information-bearing identifier tags. Oligonucleotides are a natural, high density information storage medium. The identity of monomer type and the step of addition or any other information relevant to a chemical synthesis procedure is easily encoded in a short oligonucleotide sequence. Oligonucleotides, in turn, are readily amenable for attachment to a wide variety of solid supports, oligomers, linkers, and other molecules. To facilitate oligonucleotide tag identification, one has a variety of options. For instance, one can read the tag directly from the bead by sequencing or hybridization. One can also amplify oligonucleotide tags to facilitate tag identification, e.g., by PCR.

Inert hydrocarbon tagging molecules, which are discretely resolvable by a variety of methods, such as chromatography, can also be used. See Ohlmeyer et al., Proc. Natl. Acad. Sci. USA 90, 10922–26 (December 1993), and WO 94/08051, each of which is incorporated herein by reference for all purposes. Such tags can encrypt a binary code to each chemical building block.

Most steps of the ESL methods described above can be incorporated without modification to generate libraries suitable for screening by the present methods. However, some features of the libraries used in the present methods require further comment. Most importantly, members of some of the present libraries have an additional component to the tag and compound of previous libraries, that is, a tether. A tether is any molecule that is modified by a reporter molecule in a manner such that complexes bearing modified tethers can be distinguished from complexes bearing unmodified tethers by virtue of the modification. The choices of tether and reporter molecule are interdependent.

Usually, a tether is linked to a support, which also bears a compound being screened and a tag. However, in some instances, the tether is an integral part of the support, and the reporter molecule binds specifically or nonspecifically to the support. In many applications, the tether is a polypeptide. In some instances, the tether and identifier tags are integral parts of the same molecule. For, example a polypeptide have a tether domain susceptible to modification and an identifier domain. Because, in general, all supports bear the same tether, its attachment presents no particular difficulty. The tether can be attached either before, after, or contemporaneous with the addition of the other components. Usually, the tether is preformed before attachment (as distinct from being synthesized in a step-by-step manner). The tether is generally attached to a separate site on the support from either the tag or the compound being screened. If the tether is attached before the compound and tag, the sites at which addition of the latter two compounds are to be added can be protected during tether addition and deprotected thereafter.

Usually, the compounds to be screened are connected to the support with a cleavable linker. Preferred photocleavable linkers are 6-nitroveratryloxycarbonyl (NVOC) and other NVOC related linker compounds (see WO 90/15070 and WO 92/10092; U.S. Ser. No. 07/971,181, filed Nov. 2, 1992). Other suitable linkers include nucleic acids with one or more restriction sites, or peptides with protease cleavage sites (see, e.g., U.S. Pat. No. 5,382,513). Another suitable type of linker is one that spontaneously cleaves under the conditions of the relevant assay (usually a physiological buffer). Such a linker should be stable under the conditions in which compound, tag, and tether are added to the beads, but should allow release of the compound in the course of the assay. The tether and the tag can also be connected to the support or each other via linkers, but any such linkers should not be cleavable under the conditions in which the linker joining the compounds to the supports is cleavable.

b. Other Encoded Libraries

Libraries of compounds suitable for screening by the present methods can also be generated by other methods such as phage display. In these methods, different peptides to be screened are displayed from one coat protein of a phage and the tether, which is the same in each phage, is displayed from another coat protein. For example, the peptides to be screened can be displayed from gIII and the tether from gVIII of a filamentous phage, or vice versa. Accordingly, in the terminology of encoded libraries, the phage particle is the support and the portion of the phage genome encoding the peptides to be screened is the tag. Peptides and tethers can also be displayed from genetic entities, such as bacteria, plasmids, polysomes or spores.

2. Cells and Reporter Systems

The cells used for analysis of signal transduction should be capable of expressing the receptor of interest in functional form such that the receptor can transduce a signal to induce expression of a reporter molecule from a reporter construct. The cell types typically used in genetic engineering such as *E. coli*, yeast, insect cells, amphibian or mammalian cell lines are suitable. Yeast expressing a seven transmembrane mammalian receptor is described by Price et al., *Mol. Cell. Biol.* 19, 6188–6195 (1995). Suitable mammalian cell lines include CHO, COS, HeLa, and 3T3. Primary cultures of natural cells (e.g., hemopoietic cells) expressing receptors of interest can also be used provided the cells naturally have, or can be transfected with, an appropriate reporter construct.

The term receptor is used broadly to refer to a cellular macromolecule, which interacts with a compound, and transduces a signal as a result of such interaction that causes, directly, or indirectly a detectable change in the transcription or translation of a gene or localization of a gene product. The compound may transduce a signal alone or may act in conjunction with another ligand. Often the signal is transmitted between the receptor and the gene by a cascade of intracellular events.

Many receptors are cell surface proteins, which have one or more of each of the following domains: an extracellular domain to interact with a compound, a transmembrane domain and an intracellular domain, which transduce a signal, directly or indirectly to a gene. Such receptors include ion channels (e.g., calcium, sodium, potassium channels), growth factor receptors, muscarinic receptors, acetylcholine receptors, GABA receptors, glutamate receptors, adrenergic receptors, dopamine receptors (see Harpold, U.S. Pat. Nos. 5,401,629 and 5,436,128), and adhesion proteins such as integrins, selecting, and immunoglobulin superfamily members (see Springer, *Nature* 346, 425–433 (1990). Osborn, *Cell* 62, 3 (1990); Hynes, *Cell* 69, 11 (1992)). Often the receptor is heterologous to the cell used for screening, in which case the receptor is expressed from a recombinant construct introduced into the cell.

Some growth factor receptors, such as fibroblast growth factor receptor, have tyrosine kinase activity. When such a growth factor receptor binds to its growth factor or an analog, the tyrosine kinase activity phosphorylates an intracellular protein, thereby changing the activity of the protein in some manner. The modified protein, then directly or through further intermediates, induces or inhibits transcription of a gene (e.g., birA or tissue plasminogen activator). Other receptors include NGF and VEGF. Cytokine receptors are also of interest, as is the yeast α-mating factor receptor.

Other receptors are referred to as G-protein receptors and include substance K receptor, the angiotensin receptor, the α- and β-adrenergic receptors, the serotonin receptors, and PAF receptor. See, e.g., Gilman, *Ann. Rev. Biochem.* 56, 625–649 (1987). These receptors usually have seven transmembrane segments connected by alternating intra and extracellular domains. Binding of a ligand or analog to a G-protein receptor induces an alteration in receptor G-protein interaction. The receptor G-protein interaction releases GDP specifically bound to the G protein and permits the binding of GTP, which activates the G protein. Activated G-protein dissociates from the receptor and activates an effector protein, which in turn regulates intracellular levels of second messengers, such as adenyl cyclase, guanyl cyclase, and phospholipase C.

Some receptors are intracellular proteins, such as enzymes, nuclear receptors (e.g., FXR (Farnesoid X Receptor), PPARb (Peroxisome Proliferator Activator Receptor Delta), and RZR (Retinoid Z Receptor)), organelle receptors, and hormones. If the receptor under test is an intracellular protein, the cell type chosen should have the inherent or engineered capacity to take up the compounds of the kind being tested.

A reporter gene is any gene that produces an easily detectable gene product, which can be RNA or protein. The reporter gene can be naturally present in the reporter cell but is usually an exogenous gene transfected into the cell. The gene product should be capable of being expressed in the cell-type chosen and should be capable of directly or indirectly modifying the tether attached to supports bearing the compounds. For example, the reporter molecule can modify the tether by enzymatic reaction, or participation in a binding interaction, that leads, directly or indirectly, to a detectable modification of one or more of the library complexes. Suitable reporter molecules include lytic enzymes, such as proteases, nucleases, lipases, phosphatases, sugar hydrolases, and esterases. Such enzymes cleave a tether bearing a cleavage site recognized by the enzyme. For example, if the reporter molecule is the protease tPA (see Goeddel et al., U.S. Pat. No. 4,766,075), the tether can be a substrate containing a tPA cleavage site such as one of the substrates described by Ding et al., *PNAS* 92, 7627–31 (1995). At one terminus of this substrate peptide is attached an epitope or other molecule having affinity for a known target. For example, an epitope to any available antibody, or biotin can be used. Many high affinity hexapeptide ligands are known for the anti-dynorphin mAb 32.39, for example Barrett et al., *Neuropeptides* 6, 113–120 (1985) and Cull et al., *PNAS* 89, 1865–1869 (1992). The cleavage site and binding site are arranged so that cleavage releases the binding site from the support (see FIG. 2A). Alternatively, cleavage of a site on a tether can create a binding affinity not previously present (see FIG. 2B). For example, some epitopes are recognized by antibodies only when the epitope has a free terminus and not when that terminus is internal to a fusion protein. The MAb 3E7, for example, recognizes such an epitope (see Dower et al., WO 91/17271; Cwirla et al., *Proc. Natl. Acad. Sci. USA* 87, 6378–6382 (1990).

A variety of nonlytic modifying enzymes can also be used as reporters. For example, tyrosine kinase can phosphorylate a substrate peptide to create an epitope for anti-tyrosine phosphate antibody. Alternatively, the biotinylating enzyme, BirA, can be used to place a biotin on the short artificial peptide substrate described by Schatz, *Biotechnology* 11, 1138–43 (1993). In either case, the tether is modified to allow its ready separation from unmodified tethers. Other reporter molecules are binding proteins that recognize a hapten or epitope on the tether. Some such reporter molecules have a domain recognizable by a secondary reagent. An example of this type of reporter is a soluble extracellular domain of the IL-1 receptor containing at its C-terminus the HPAP epitope. Whitehorn et al., *Bio/Technology* 13, 1215–1218 (1995). The tether is the IL-1 ligand. Binding of the IL-1 receptor to the tether labels the affected beads with the HPAP epitope carried by the receptor. Other reporter genes that can be used include luciferase (de Whet et al., *Mol. Cell. Biol.* 7, 725–737 (1987)), chloramphenicol acetyl transferase, β-galactosidase (e.g., Kumar et al., *Bio/Technology* 10, 82–85 (1992)) and alkaline phosphatase (Toh et al., *Eur. J. Biochem.* 182, 231–238 (1989)). These reporter genes process a chemical substrate on the tether to a product having a characteristic spectral emission not present in unmodified tethers. For example, β-galacotosidase processes X-gal to generate a blue color.

In some methods, a secreted beta-galactosidase reporter molecule can be used to modify a caged β-galactosidase substrate of the structure: β-D-galactose-YGGFL-linker-biotin. (SEQ ID NO:4) Reaction with secreted beta-galactosidase cleaves off the galactose residue (caging moiety) producing a product of the structure; YGGFL-linker-biotin. (SEQ ID NO:5). The product is then bound by antibody (3E7 Hertz et al., *Life Sci.* 31, 1721–1724). The caged β-galactosidase substrate can be used directly as a tether, in which case the modification can be recognized by capacity of the modified tether to bind 3E7. Alternatively, 3E7 can be used as the tether, which is then modified by binding the YGGFL-linker-biotin product. Modified tethers can be recognized by staining with phycoerythrin (PE) conjugated anti mouse antibody in the former situation and PE- conjugated Streptavidin in latter situation followed by FACS™ separation of complexes with modified tethers from complexes with unmodified tethers. Other peptides or molecules with binding partners can used in place of YGGFL (SEQ ID NO:6) and 3E7.

In other methods, secreted beta-galactosidase is used as reporter with fluorescein di beta-D-galactopyranoside (FDG—Molecular Probes F-1179), or a variety of other fluorescent beta-galactosidase reactive molecules, as substrate. In this scheme, β-galactosidase removes the galactopyranose cage groups from solution phase non-fluorescent FDG to produce highly fluorescent fluorescein which can modify a tether of anti fluorescein antibodies (Mol. Probes A-6421 mouse monoclonal, or biotinylated Ab A-982) on complexes. In this scheme, tether modification and fluorescence staining of the bead are done in one step. Complexes with tethers modified by fluorescein are then separated by FACS™.

Other suitable reporter molecules are bifunctional molecules capable of binding to a tether at one end and a label at the other end. For example, an IL-1 receptor linked to an epitope of an antibody (e.g., Ab179) at its C-terminus can bind to a tether, such as IL-1 and to the antibody. Thus, complexes become modified by attachment of IL-1 to a tether and modified complexes can be distinguished from unmodified complexes by screening for capacity to bind the antibody.

A preferred reporter gene is secreted alkaline phosphatase (SEAP) (available from Clontech) used in conjunction with a tether comprising biotinylated form of the marker substrate peptide (phospho-YGGFLGGGGSK[biotin]). (SEQ ID NO:7) This tether can be attached to beads that have previously been treated with streptavidin, which is passively absorbed by the beads. The phosphorylated peptide is not recognized by antibody 3E7, but once tyrosine is dephosphorylated, the peptide is uncaged and reactive with the antibody. An analogous reporter system employs β-galactosidase as the reporter molecule and gal-YGGFLGGGSK[biotin] (SEQ ID NO:8) as the tether. Another preferred reporter gene is yeast secreted acid phosphatase, for example, those encoded by the *Saccharomyces cerevisiae* PHO3 or PHO5 genes.

The reporter gene is expressed from a construct in which the gene is operably linked to a promoter, and optionally, a DNA sequence encoding a signal sequence, and/or other regulatory sequences such as enhancers, activators and repressors. The promoter is chosen from a gene whose expression is activated by signal transduction through the receptor of interest. The signal sequence, if present, should be recognized by the cell type employed and be capable of directing the secretion of the reporter molecule from the cell. Other regulatory sequences, if present, are often selected from sequences flanking the promoter of the gene from which the promoter is obtained. However, they can also be obtained from other genes, which may or may not be activated by the receptor. For example, the immunoglobulin heavy chain μ enhancer can be used to stimulate expression of many kinds of heterologous genes. The inclusion of regulatory sequences serves to amplify the transduced signal from the reporter gene and/or reduce background expression in the absence of such signal, thereby increasing the sensitivity of the assay.

As an example, when the receptor is a G-protein linked receptor, the promoter and regulatory sequences linked to a reporter gene can be obtained from the 5'-flanking region of the genes fos or jun. Hill et al., *EMBO J* 14, 5037–47 (1995); Pennymaker et al., *FASEB J*, 8, 475–8 (1994). Fos and jun encode proteins that participate in the regulation of many cellular genes. The 5' flanking sequences of fos and jun genes contain elements responsive to activation by $Ca^{2+}$ and cAMP, both of which are secondary messengers in G-protein linked receptor signal transduction. For example, linkage of the reporter gene to the fos promoter and 700 bp upstream region is suitable.

3. Contacting of Compounds and Reporter Cells

The assay can be performed by placing the library of complexes in proximity to the reporter cells in a matrix that allows diffusion of compounds and reporter molecules over short distances (commensurate with the dimensions of the complexes and cells) but retains the complexes and cells in substantially fixed positions relative to one another. Usually, the cells are present in excess with respect to the complexes (e.g., about 5, 10 or 100-fold excess) to minimize or prevent "cross-talk"—the incidental labeling of a complex not carrying a transducing compound, by virtue of its physical proximity to a complex that does carry a transducing compound.

One suitable format is a suspension of an excess of cells and a controlled concentration of supports in a layer of soft agarose or agar (preferably low melting temperature) several mm thick (a "thick 2-D" arrangement). For example, a library of $10^9$ 10 μm beads can be screened with $10^{10}$ cells spread as a lawn on a thin soft agar layer on an area the size of a cafeteria tray. Another suitable format is to distribute the supports in an array on a membrane and contact the membrane with a layer of reporter cells. In a variation, supports and cells are distributed in gel microdrops, such that only one or a few supports are present in the same drop. See Weaver et al., in *Methods: A companion to Methods in Enzymology* 2(3) 234–247 (1991).

Alternatively, the assay can be performed in a 3D format by contacting cells and complexes in a column matrix. The column matrix can comprise a plurality of compound bearing supports interspersed among a plurality of cell culture microcarriers (Pharmacia) that have responsive reporter cells adhered on the surface as described by Pharmacia. See *Microcarrier Cell Culture* (Pharmacia, Sweden, 1981). The matrix of supports and microcarriers can further be diluted by the addition of inert solid beads to the matrix contained within the column. The fluid matrix can be maintained or exchanged using similar methods to that of standard column chromatography. In a further 3D format, cells and complexes can be contacted in a liquid medium with relative movement of the two constrained by temporary crosslinking. Suitable heterobifunctional cross-linking agents are described by Pierce, *ImmunoTechnology Catalog and Handbook* (1991), pp. E10–E18. Crosslinking can occur before or after addition of the cells and complexes to the liquid matrix, but is usually complete before release of compounds from the supports. After modification of the tether has occurred, the crosslink between cells and supports is usually broken before performing subsequent steps such as the separation of complexes bearing modified tethers from complexes bearing nonmodified tethers. Supports can be crosslinked to cells or cell-microcarrier complexes by several methods. They can be crosslinked by chemical methods described by Pierce, or preferably they can be crosslinked by simple absorption of the support to the cells, cell/microcarriers or, more preferably, to the microcarrier itself with the cells grown onto the carrier after the support had been linked to it. Often the supports are linked by a high affinity interaction between a support bearing a ligand and a receptor on the cell surface or an antibody or receptor linked to the support binding a ligand display by the cell (see Whitehorn et al., *Bio/techology* 13, 1215–1219 (1995)).

Having contacted the complexes with the reporter cells, compounds are usually freed from the complexes. Freeing the compounds from the complexes speeds the rate of diffusion of compounds to receptors and allows compounds to interact with a receptor without any conformational constraints imposed by the rest of the complex. Freeing compounds is particularly appropriate for libraries having compounds linked to relatively massive supports, such as beads, but is less important in libraries having small biological supports such as phage, or in libraries, in which tag, tether and compound are linked directly to each other without an intervening support. Compounds are usually freed from a complex by cleavage of a linker connecting the compounds to the complex. In the thick 2D and liquid 3D formats noted above, linkers connecting compounds to supports are accessible to photolytic cleavage. Alternatively, the compounds can be connected to the complexes with a linker subject to enzymatic cleavage, and the compounds released by exposure to the enzyme. For example, the enzyme can be included in the soft agarose or other matrix in which cells and complexes are contacted. For coordinated release of the different compounds, the complexes and reporter cells can be contacted at low temperature at which the enzyme is inactive, and the enzyme can then be activated by raising the temperature. An analogous approach can be used to release compounds connected to complexes by linkers susceptible to chemical cleavage.

After contacting the complexes and cells in a suitable medium and releasing the compounds from the complexes, a released compound diffuses to a receptor of a cell proximate to the complex that released the compound. Some compounds transduce a signal through the receptor, whereas others (usually, the vast majority of compounds) do not. If a compound does transduce a signal, the signal induces expression of the reporter molecule within the cell.

Often the reporter molecule is expressed as a fusion protein having a signal sequence, in which case, the signal directs the secretion of the reporter molecule from the cell. Alternatively, the reporter molecule can be expressed without a signal sequence, in which case it accumulates in the cell. After a suitable period of accumulation of reporter molecule, cells are lysed (e.g., by infusion of detergent into the matrix) releasing reporter molecules to the medium proximate to the cell in which they were originally contained. This alternative procedure can be advantageous in coordinating a release of a burst of reporter molecules from a stimulated cell thereby increasing the sensitivity of the assay.

Irrespective whether the reporter molecule is released by secretion or lysis, on leaving the cell, it diffuses a short distance through the surrounding media to the complex from which the compound inducing expression of the reporter was released. The reporter molecule then modifies the tether of the complex in some manner. For example, the reporter molecule can cleave the tether, bind to the tether or enzymatically alter the tether. Thus, complexes are marked (by the modified tether) as carrying a compound that activated a cell.

4. Separating Modified Tethers from Nonmodified Tethers

The next step is to separate, or at least, enrich for complexes bearing modified tethers from the total pool of complexes. The manner of separation or enrichment depends on the nature of the modification. In several of the examples discussed above, the modification either confers or destroys a capacity to bind a specific target. For example, if the modification is enzymatic cleavage, the modification can cause a suitably designed tether to lose a domain having affinity for a target. Alternatively, the cleavage can create a free terminus for an epitope that requires such a terminus for binding thereby conferring a binding specificity not present in the unmodified tether. Additional binding specificity can also be conferred by modifications in which the reporter molecule binds to the tether or enzymatically modifies the tether in such a manner that another entity is added (e.g., birA catalyzes addition of biotin). In all of these situations, complexes bearing modified tethers can be separated from complexes bearing unmodified tethers by affinity purification to the target for which binding affinity is lost or acquired. If binding affinity is acquired, complexes binding to the target are retained and other complexes discarded. Conversely if binding affinity has been lost, complexes binding to the target are discarded and other complexes are retained. Affinity purification can be performed by similar approaches to those employed in ESL or phage-display methods except that the moiety binding to the affinity reagent is the tether rather than compounds being screened. Methods from the field of protein purification can also be employed (e.g., immobilization of the target to a column).

Alternatively, a novel and particularly effective separating method uses a target labelled with a dense metal, such as gold. The method exploits a change in buoyant density imparted upon receptor/dense metal binding. Complexes to be screened for binding to the receptor are first blocked for nonspecific binding, e.g., with BSA. The blocked complexes are contacted with receptor labelled with a dense metal. Labelling can be accomplished, for example, by binding of an anti-Ig antibody labelled with colloidal gold to an antibody receptor. Binding supports are separated from nonbinding supports by centrifugation through density-adjusted media. For example, phosphate-buffered sucrose (about 40 Brix units) is suitable. Bound supports migrate to the bottom of the tube whereas nonbinding supports remain on the surface or migrate to an intermediate point of the tube.

This separation method is illustrated in FIGS. 3A and B. The upper part of FIG. 3A shows beads with a peptide tether. One tether is marked with biotin and the other is not. The support with the marked tether can bind through the biotin to a streptavidin colloidal gold particle. In the lower part of the figure, supports bearing modified tethers are separated from supports bearing unmodified tethers by centrifugation. FIG. 3B shows an alternate scheme in which a support bears a tether modified to acquire affinity for the anti-DynB antibody. Initially the support is incubated with BSA to block nonspecific binding. The support is then contacted with the antibody to which it binds via the tether. After washing away unbound antibody and support, the antibody is labelled with gold by binding of a goat anti-mouse colloidal-gold labelled antibody. The complexes are resuspended in approximately 38% sucrose phosphate-buffered saline and centrifuged at 15,000 g for 1 min. Supports binding to the target antibody are then recovered from the bottom of the tube.

Where the modification of the tether confers a change in spectral properties of the tether different approaches are used for separating complexes bearing modified and unmodified tethers. For example, complexes can be separated into different fractions by FACS™. Alternatively, the complexes can be plated in a soft agar layer and modified supports picked by color. For example, this approach works well when the reporter molecule binds the tether and also has an enzymatic activity conferring an easily detectable color change on a substrate (e.g., alkaline phosphatase).

The screening methods described above usually isolate a collection of different library members. Individual members are then isolated from the collection by means such as infinite dilution, micromanipulation, or fluorescence activated cell sorting (FACS) (*Methods Cell Biol.* 33, (Darzynkiewicz & Crissman eds., Academic Press); Dangl & Herzenberg, *J. Immunol. Methods* 52, 1–14 (1982).

5. Tag Decoding and Compound Synthesis

When complexes bearing modified tags have been isolated, the tags are decoded by conventional means. For example, if the tags are nucleic acids, they can be decoded by PCR amplification and sequencing. Other types of tags can be decoded by, for example, mass spectrometry, FACS™, gas chromatography or HPLC. The information from decoding the tag identifies the compound (or component(s) thereof) originally from the same complex as the tag. Based on this information the compound can be synthesized de novo. For example, if the compound is a peptide, it can be synthesized on a peptide synthesizer. If the compound is a benzodiazeapine, it can be synthesized by conventional organic chemistry. If a substantial collection of compounds are identified, the compounds can be resynthesized on supports and rescreened by reiteration of the same approach.

6. Variations a. Secondary Reporters and Signal Amplification

A primary reporter molecule, e.g., produced in response to signal transduction can modify the tether of a complex either directly or indirectly. By indirect modification, it is meant that the primary reporter molecule modifies a second reporter molecule, which in turn modifies the tether. In assays involving two reporters, the designation of reporters as primary or secondary can be arbitrary. Thus, the invention also includes situations in which a secondary reporter modifies a primary reporter, which in turn modifies a tether.

In some methods, a primary reporter molecule is expressed in a reporter cell and released from the cell where it modifies a secondary reporter in solution outside the cell. For example, the primary reporter molecule can be an enzyme and the secondary reporter molecule, a substrate susceptible to modification by the enzyme. Modification of the substrate can then allow it to bind to a tether. Optionally, the substrate is labelled, or becomes labelled as a result of modification, allowing for separation of modified tethers by virtue of the label. Optionally, the substrate has two domains, one of which allows binding to the tether, the other of which allows detection of the substrate by binding to another moiety, such as antibody. Binding of one or other of the domains to its partner is dependent on modification of the substrate by the reporter.

Optionally, the secondary reporter molecule can be immobilized to a solid phase. In such situations, the primary molecule can serve to cause release of the secondary reporter molecule allowing it to diffuse to nearby complexes modifying their tethers. For example, the primary reporter molecule can cleave a proteolytic cleavage site linking the secondary reporter to the solid phase. Alternatively, the primary reporter can compete for binding to the secondary reporter with an immobilized ligand to which the secondary reporter is reversibly bound.

In another variation, as an alternative to direct modification by tPA of a tether comprising a tPA substrate, the tPA can be used to convert plasminogen to plasmin, and the latter can modify a tether comprising a plasmin substrate (Wrighton, in *Methods in Molecular Biology,* Vol. 7, Ch. 16 (Humana Press, Inc. Clifton, N.J., 1991)). Such is achieved by including plasminogen in the medium in which cells and complexes are mixed. When tPA is released by a responding cell, the plasminogen in the vicinity of the cell is converted to the active protease, plasmin, which then acts on the local tether(s). For example, the tether on the supports can be of the form: XXXXX^YGGFL, (SEQ ID NO:9) where XXXXX (SEQ ID NO:10) denotes a sequence that allows efficient cleavage by plasmin at the position marked ^ in the sequence (e.g., acetyl-GIYR) (SEQ ID NO:11). Cleavage exposes N-terminally free YGGFL (SEQ ID NO:6), allowing the binding of 3E7 MAb. This cascade provides a more active marking of the complexes bearing transducing compounds thereby increasing the sensitivity (i.e., absolute number of true positives recovered). Sensitivity can be controlled by how much plasminogen is added to the system. However, in some instances, the possibility of cross-talk may also be increased. In a variation, one reporter molecule, whose expression is coupled to activation of a receptor, can be a regulatory molecule that induces synthesis of another reporter molecule, which has the capacity to modify tethers.

In another amplification cascade, the primary reporter molecule is a site-specific protease, which activates a fusion protein comprising a secondary reporter, a proteolytic cleavage site and a peptide that inhibits the secondary reporter. Cleavage of the proteolytic site by the primary reporter, separates the secondary reporter from its inhibitor peptide and allows the secondary reporter to modify tethers of proximate complexes (or a tertiary reporter). For example, a suitable fusion protein comprises BirA linked to a peptide inhibitor of BirA via a proteolytic cleavage site. Optionally, the fusion protein can also contain a tag to facilitate purification (see FIG. 6).

The primary reporter molecule is expressed in cells, and released from the cells where it cleaves the fusion protein at the proteolytic cleavage site, thereby freeing BirA from the inhibitor peptide. The freed BirA can then modify a tether on proximate complexes.

The BirA-inhibitor fusion protein can be designed by screening a library of fusion proteins to select a molecule with the desired properties. For example, a fusion gene can be selected that does not complement an E. coli birA temperature-sensitive mutant unless coexpressed with a protease. BirA-ts cells are transformed with a library of possible constructs and a protease gene controlled by a strictly regulated inducible promoter. The library is initially be plated at low temperature to allow growth of the ts strain. The resulting colonies are then replica-plated to plates plus and minus inducer, and incubated at the high temperature that normally prevents the ts strain from growing. Colonies are selected that grow at this temperature on the plates with inducer but not on the plates without inducer. These colonies encode fusion genes that express functional BirA only in the presence of the protease. Suitable starting materials for the inhibitor moiety of the fusion protein are derivative of one of the small peptide substrates for biotinylation described in Schatz, *Bio/Technology* 11, 1138–1143 (1993). For example, a 14-mer peptide (GLNDIFEAQKIEWH) (SEQ ID NO:12) is a quite good substrate for BirA, comparable to the natural protein substrate, and it is likely that a simple modification of this sequence turns a substrate into an inhibitor.

Figure 6:
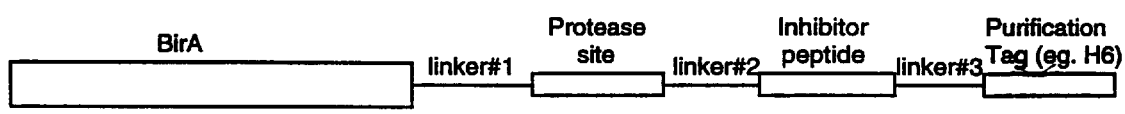
FIG. 6: BirA fusion protein as a secondary reporter in amplification scheme for tether marking (purification tag H6:SEQ ID NO:2).

Linker #1, the protease site, and linker #2 in FIG. 6 are chosen to allow the inhibitor peptide to interact with the active site of BirA such that the enzyme had low activity. The purification tag allows preparation of large amounts of protein with a low level of any unintentially activated BirA.

The sensitivity of the bead marking assay is controlled by adding different amounts of the purified fusion protein. Variation in sensitivity is desirable depending on the extent of signal transduction for different receptors under test.

In another amplification cascade, the secondary reporter is a molecule that is trapped in inactive form, and the primary reporter is a molecule that releases active secondary reporter, which modifies a tether. For example, the secondary reporter can be an enzyme that is trapped on a surface or imprisoned in a matrix so that it was inaccessible to its substrate. In this situation, the primary reporter serves to release the second from the inaccessible location and allow it to act. For example, the second component can be a reporter enzyme, such as phosphatase, beta-galactosidase, BirA, luciferase, or green fluorescent protein trapped in the interior of a microsphere in such a way as to be inaccessible to their respective substrates. The primary reporter has activity that leads to breakdown of the microsphere and the release of the secondary reporter into an active state. For example, the primary reporter can be a hydrolytic enzyme that degrades the matrix of the microsphere, thus releasing the second reporter to modify a tether (or activate a third reporter, which modifies the tether). Alternatively, the first reporter can be a molecule with capacity to change the pH of surrounding media thereby degrading a microsphere enclosing a secondary reporter. For example, some route of signal transduction activate cells so that they increase metabolism, thereby increasing the rate at which they acidy the surrounding medium. As in other amplification systems, sensitivity can be controlled by varying the amounts of the secondary reporter.

In addition to a hydrolytic enzyme, the first component could be some other agent that led to the release of the second component. For example, the first component could be a pH change brought on by the activation of the reporter cell. The altered pH could lead to the release of the second component from its inactive state, for example by degrading the matrix of a microsphere, or leading to the hydrolysis of an acid-labile linker.

Of course, these principles can be extended to a cascade of reporter molecules. For example, expression of a first reporter molecule can be coupled to transduction through a cellular receptor, the first reporter molecule can induced synthesis or modify a second reporter molecule and the second reporter molecule can induce or modify a third reporter molecule, which modifies a tether.

Reporter Systems Employing Site-Specific Recombinases

In a variation of the above approach, reporter cells contain two constructs, which can be present on the same or different replicons. One construct encodes a site-specific recombinase operably linked to regulatory sequences that result in expression of the recombinase when a target receptor on the reporter cells is activated by a transducing compound. Examples of site-specific recombinases include Cre and Flp (see Kilby et al., *Trends in Genetics* 9, 413–421 (1993)).

The regulatory sequences depend on the target receptor. For example, to screen for activators of 7TM receptors, the recombinase is placed under the transcriptional control of a promoter which responds to 7TM receptor signalling. Examples include the fos promoter, or an engineered promoter composed of repeating cyclic AMP response elements, or the Fus1 promoter if the 7TM receptor is expressed in yeast reporter cells. As a further example, to screen for activation of a T-cell receptor, the recombinase can be linked to an NFAT promoter. In a further variation, the site-specific recombinase can be expressed as a fusion protein with a target receptor, such that the recombinase is inactive in the fusion protein unless the fusion protein is bound to a ligand, which causes steric changes that activate the recombinase. Activation of recombinases fused to ligand binding domains of nuclear receptors on ligand binding has been reported. See Logie & Stewart, *Proc. Natl. Acad. Sci. USA* 92, 5940–5944 (1995); Metzger et al., *Proc. Natl. Acad. Sci. USA* 92, 6991–6995 (1995); U.S. Ser. No. 08/901,540. Suitable nuclear receptors include estrogen, glucocorticoid and androgen receptors.

The other construct in the reporter cells contains a gene comprising a coding sequence for a reporter molecule, a promoter (usually strong and constitutive, such as an SRa or CMV promoter) and an inactivating sequence present in either the coding or noncoding sequence of the gene, which prevents expression of the coding sequence from the promoter. The inactivating sequence can be virtually any sequence which disrupts expression of the coding sequence (e.g., by insertion of a stop codon) or inhibits transcription of the downstream reporter gene. Preferably, the inactivating sequence is itself capable expressing a selectable marker. Selection for this marker ensures retention of the inactivating sequence in the second construct until use in the assay thereby reducing background levels of reporter molecule.

As an example, a reporter vector for use in yeast can be constructed containing a reporter coding sequence interrupted by a URA3 auxotrophic marker flanked by loxP sites. Excision of the marker by Cre expressed from e.g., a FUS1 promoter leads to expression of the reporter. Acid phosphatase encoded by pho3 or pho5 is an example of a suitable yeast reporter.

The inactivating sequence is flanked by specific sites recognized by the site-specific recombinase, which allow excision of the inactivating sequence when the site-specific recombinase is expressed. Suitable site-specific recombinases are Cre and Flp, which recognize loxP and frt sites respectively. Selection of an inactivating sequence may also select for variants of loxP and frt that are less susceptible to recombinase action, thereby reducing background levels of the second reporter. See Senekoff et al., *J. Mol. Biol.* 201, 405–421 (1988). Cre and Flp recombinases can also be mutagenized to give less active variant forms, if desired.

Excision of the inactivating sequence results in expression of the reporter molecule which can be released from cells and modify the tether of the complex bearing the transducing compound. Signal transduction in just a few or even single cells causes a permanent phenotypic switch of gene expression, and results in the conversion of a short-term signal into a long-term response which can be amplified. Also, because the reporter can be expressed from a strong constitutive promoter rather than a weak regulatable promoter (e.g., fos or jun), the reporter can be expressed in larger amounts that a reporter directly coupled to signal transduction.

In a further variation, a construct encoding a deactivated reporter gene as described above also contains regulatory sequences that render expression of the deactivated gene inducible on signal transduction through a cellular receptor. The cells also contain a second construct encoding a recombinase enzyme, expressed from an inducible promoter, such as a tetracycline-sensitive promoter (Gossen et al., *Proc. Natl. Acad. Sci. USA* 89, 5547 (1992)). In the presence of inducer, the recombinase is expressed and excises the inactivating sequence from the reporter gene, allowing the reporter gene to be expressed to generate functional reporter molecules when the cellular receptor is activated by a transducing compound. In general, the inducer is added to cells shortly before releasing compounds from the complexes, thereby arming the reporter molecule immediately before the assay for transducing activity is performed. Accordingly, the background level of functional reporter molecule in the absence of transducing compound is reduced.

b. Reporter systems Including Nuclear Receptors

One such reporter system, in which a recombinase enzyme is linked to a ligand of a nuclear receptor has been described in the previous section. In another such reporter system, a modifying enzyme is placed under the transcriptional control of the yeast Gal4 promoter. Signal transduction is regulated by a chimeric protein comprising the Gal4 DNA binding protein and the ligand binding domain of a nuclear receptor. When ligand binds to the receptor, the chimera binds the upstream gal4 site on the DNA and activates transcription of the modifying enzyme.

C. Partial Cleavage of Compounds From Complexes

The release of only a portion of a compound from a complex is often desirable. Controlled, partial release of the library compound allows rescreening of the positive beads to confirm that they are truly positive or to enrich for the best transducing compounds. Rescreening may be desirable in instances where the primary screen is done at high bead density, and cross-talk may occur. In these instances, the positive complexes are selected and rescreened at a lower density, thus reducing the likelihood of cross-talk and false positives. Partial cleavage can be achieved by controlling of reaction conditions (e.g., temperature, time, frequency of radiation, amount of enzyme added). Alternatively, compounds can be attached to two or more different linkers on the same complex, which linkers are susceptible to cleavage by different mechanisms, thereby allowing separate release of first and second aliquots of compound. For example, this can be accomplished by having two linkers both of which have photocleavable groups, but in one of which the photocleavable group is initially masked. After release of first aliquots of compounds by cleavage of the unmasked linker, the masked linker is unmasked and second aliquots of compounds can be released.

d. Regeneration of Tethers

If the same complexes are to subjected to more than one round of screening, it is preferable to regenerate the tethers between rounds. If tethers are regenerated, a compound must independently survive both screening rounds to be scored as a transducing compound. As an example, regeneration can be achieved by covalently attaching biotin molecules to the complexes, followed by addition of streptavidin, and then a fusion protein comprising a C-terminally biotinylated tPA substrate peptide linked to an epitope for a known target. This creates a sandwich of bead-biotin-streptavidin-biotinylated tPA substrate/epitope. Primary screening is performed as described above, and after selection, the marked complexes (tPA tether cleaved) are regenerated to the unmarked state by heating or extracting the complexes to remove the streptavidin and residual tPA substrate peptide. These complexes can then be re-exposed to biotin to which fresh streptavidin and biotinylated tPA substrate/epitope can be attached.

In a variation, complexes bear at least two different tethers susceptible to modification by two different reporter molecules. Complexes are exposed to first and second reporter cells, each having the same receptor, but differing between the reporter molecules coupled to activation of the receptor. Activation of the receptor in a first round of screening results in export of a first reporter molecule, which modifies a first tether on the complexes. Activation of the receptor in the second round of screening results in export of a second reporter molecule, which modifies the second tether on the complexes.

e. Controlled Release of Reporter Molecule

As noted above, the sensitivity of the assay can sometimes be increased by allowing the reporter molecule to accumulate in cells before the controlled lysis of cells and concomitant release of a burst of reporter molecules. One method of achieving controlled release of a reporter molecule is to link the reporter molecule to a phospholipid anchoring domain and signal secretion sequence as described in commonly owned copending U.S. Ser. No. 08/309,345, filed Sep. 19, 1994 (incorporated by reference in its entirety for all purposes). Usually, the anchoring domain is linked to the C-terminus of the reporter molecule and the signal sequence to the N-terminus of the reporter. The signal sequence directs secretion of the reporter molecule from the cell where it becomes attached to the surface phospholipid layer by the anchoring domain. Controlled release can then be achieved by cleaving the bond between phospholipid and the reporter molecule by addition of a phospholipase to the matrix in which cells and complexes are contacted. For example, the anchoring sequence from the human placental alkaline phosphatase gene CLEPYTACDLAP-PAGTTDAAHPGRSVVPALLPLLAGTLLLLETATAP (SEQ ID NO:13) or a subsequence thereof, capable of anchoring the receptor is suitable. Anchored reporter molecules can released from cells by addition of the enzyme phosphoinositol phospholipase C.

In a variation, reporter cells encode first and second reporter molecules. The coding sequence for the first reporter molecule is operably linked to regulatory sequences that place expression subject to activation of the receptor. The first reporter molecule encodes a protein that can effect lysis of the cell, such as phage λ lytic protein. The second reporter molecule is constitutively expressed and has a property that renders it capable of modifying tethers. On activation of the receptor, the first reporter molecule is expressed, causing lysis of the cell and release of the second reporter molecules, which modifies the tether of beads in proximity of the cell.

f. Coincidence Circuits

The specificity (ratio of true positives to false positives) of the above methods can be increased by requiring that a compound transduce two events for the tether on the complex bearing the compound to be modified. For example, the two events can be the generation of a primary and secondary reporter molecules, whereby the primary reporter molecule modifies the secondary reporter molecule to a form in which the latter can modify the tether. Alternatively, the secondary reporter molecule might function to release the primary reporter molecule from phospholipid anchorage. The primary and secondary reporter molecules should be expressed from constructs susceptible to induction by the same receptor. However, the primary and secondary reporter may be in the same or different cells, bearing the receptor. If the two reporters are expressed in separate cell types, the two cell types are mixed before releasing compounds from complexes. The two reporters are both expressed from regulatory sequences activated by the receptor, but the regulatory sequences need not be the same for the two reporters, and are preferably different. For example, if the receptor is a G-protein linked receptor, the first and second reporter molecules can be expressed from fos and jun regulatory sequences respectively. The use of different regulatory sequences for expression of the two reporter molecules can reduce background signal not due to receptor transduction.

A different type of coincidence circuit can be used to select for compounds specific for a particular receptor. This circuit specifically selects for compounds that transduce a signal through a first receptor but which are unable to transduce a signal through a second receptor. This circuit is designed by linking the first and second receptors to expression of first and second reporter molecules, of which the second inactivates the first rendering the latter incapable of modifying the tether. For example, if the first reporter molecule is a proteinase, tPA, the second reporter molecule can be a proteinase inhibitor, such as aprotinin. In this type of coincidence circuit, the first and second receptors are different from each other and the first and second reporter molecules are expressed from constructs bearing regulatory signals appropriate for signal induction by the respective receptors. The second receptor can be a variant form of the first receptor (e.g., one or a few amino acid changes), a distinct, but related receptor (e.g., two G-protein linked receptors) or entirely unrelated, depending on the degree of specificity for which selection is desired. The first and second receptors (and respective reporter constructs) can be expressed from the same or different cell types. If expressed from different cell types, the first and second reporter molecules should be secreted, or otherwise released from the respective cells, for inactivation to occur.

g. Screening in Wells of Assay Plate

In a further variation, complexes are contacted with cells in the wells of an assay plate, and compounds are then released from the complexes. In this approach, complexes can be contacted with cells in a liquid allowing free diffusion of the compound. The wells confine a reporter molecule released from a cell such that it can only modify the tethers of complexes present in the same well. If there is only one complex per well, only that complex can be modified by the receptor. After an appropriate period of incubation, complexes are removed from the wells and pooled. Complexes having modified tethers are isolated by virtue of the modified tethers. It is not necessary to retain any record which complexes came from which wells in the screening process. Therefore, orders of magnitudes more wells, and consequently, orders of magnitude larger libraries can be screened than in conventional methods in which each well must be analyzed individually for compound activity. For example, libraries of $10^8$ compounds can be screened. The capacity to screen libraries of such size allows identification of compounds with capacity to bind to, agonise or antagonize virtually any receptor of interest.

Usually an initial round of screening is performed in which there are multiple complexes present in most wells in the array (e.g., about 10 to 1000 per well). In this situation, if a well contains a single complex bearing a transducing compound, any complex in the well can be modified. However, in wells lacking a complex bearing a transducing compound, no complexes are modified. After incubation and pooling of complexes, the complexes bearing modified tethers are enriched for transducing compounds.

The enriched pool of transducing compounds can be subjected to a second round of screening. This is most readily performed when the compounds are attached to support in such a manner that the compounds can be released in two aliquots. In this situation, the second screening commences by regenerating the modified tether. The enriched complexes are then contacted with fresh cells in the wells of a fresh assay plate, and the second aliquot of compounds is released from the cells. In the second round of screening, there are fewer complexes per well (preferably, most wells have only one complex), so that a greater degree of enrichment is obtained.

A suitable assay plate resembles a conventional microtiter dish except that the wells are smaller and more numerous. For example, an assay plate containing $10^6$ wells in an array of 1000 by 1000, each well having dimension of 100 μm×100 μm×100 μm (1 nl) measures 10 cm by 10 cm and can be fabricated by photolithographic techniques. The wells needed not be arranged in any particular geometric configuration. The library of compounds can be synthesized on monobeads and about $10^8$ beads can be conveniently screened on a single plate at an average density of about 100 beads per well. Each 10 μm mono bead has ~10 fmol of synthesis sites. Given a synthetic yield of 50%, and a two stage release in equal aliquots, each aliquot of compound released is 2.5 fmol per bead. This quantity, when released into an assay volume of 1 nl produces a concentration of 2.5 μM.

The beads can be loaded into the wells in bulk by settling from a concentrated slurry. Each well contains from about 1–1000 reporter cells, and preferably about 100 cells. Thus, for example, about $10^8$ monobeads and $10^8$ cells in a volume of about 1 ml are loaded on to an assay plate. The first aliquot of compound is released from the beads (e.g., by exposure of a photocleavable linker to light), and the assay is allowed to run a sufficient time for expression of the reporter molecule to be established.

Assuming 1 active bead per million, screening $10^8$ beads activates the reporter in about 100 wells. Each active well contains 100 beads, only one of which carried an active compound, but all of which become marked by the reporter cells. This round of screening produces a total of ~10,000 marked beads (100 true positives). All $10^8$ beads are then removed en masse from the assay plate and beads having modified tethers are isolated. The $10^4$ recovered beads are then stripped of the modified tether and a fresh tether is regenerated on the beads. These beads (along with a mass of carrier beads to aid in handling the small numbers of tiny beads) are reloaded into the assay plate along with a fresh batch of reporter cells. Because $10^4$ beads are loaded into a plate with $10^6$ wells, the probability is low that any well receives more than one bead. The second aliquot of compound is released (e.g., by exposure of a second photocleavable linker to a different wavelength) and the assay repeated. Once again, the beads are washed from the plate, and beads bearing modified tethers are isolated. The synthesis history of the beads bearing transducing compounds can then be decoded from the tags.

Several alternative approaches for limiting diffusion of reporter molecules to proximate supports. For example, library beads and reporter cells or receptor reservoir beads (see section IV, infra) can be confined within aqueous droplets sprayed into the air. Alternatively, assay components can be confined in droplets of aqueous buffer sprayed onto a surface that preserves the integrity of the droplets due to the properties of the surface and the inherent surface tension of the buffer. In a further variation, assay components are isolated in packets of aqueous buffer in tubing where diffusion is limited by isolating the packets with bubbles of air.

h. Screening for Antagonists

In a further variation, the invention provide methods for assaying complexes bearing compounds for capacity to antagonize a cellular receptor. In such methods, a reporter cell has a genotype such that cell growth is inhibited in the presence of an agonist to the cellular receptor. For example, a yeast containing the wild-type FAR1 allele arrests in the presence of agonist α-factor. The reporter cells are engineered to secrete constitutively a reporter enzyme such as acid phosphatase or secreted beta-galactosidase. After release from its complex, a compound with antagonistic properties inhibits binding of the agonist to the receptor allowing the reporter cells to continue to grow. The increased biomass resulting from growth results in increased levels of reporter enzyme in the medium, and increased modification of the tether of complexes proximate to growing cells. The majority of cells, which are not proximate to a complex bearing an antagonist arrest and only secrete low amounts of reporter enzyme.

In a variation of the above scheme, the reporter gene is placed under the control of a regulated promoter which is switched on at the beginning of the assay. For example, the reporter gene can be placed under the control of a tetracycline-regulated promoter (Gari et al., *Yeast* 13, 837–848 (1997)). At the time of exposure of the cells to antagonist (i.e., t=0), the tetracycline is removed. Shortly thereafter, the cells are exposed to agonist. In the absence of antagonist the cells arrest and only a minimal amount of reporter enzyme is expressed from the regulated promoter. In the presence of antagonist, the cells do not arrest, biomass increases, and a greater amount of reporter enzyme is expressed, and tethers of proximate complexes are modified.

i. Oligonucleotide Tethers

In a further amplification scheme, the reporter is a nucleotide polymerase, preferably a heat-stable DNA polymerase, such as taq. Library complexes are contacted with reporter cells containing a reporter construct encoding the heat stable DNA polymerase in a medium containing two primers, and other reagents required for template-directed nucleic acid synthesis (other than a polymerase). One or both of the primers are usually labelled. A template is also present either in the medium or immobilized to a support, optionally, as a component of a complexes. The tether moiety of the complex is an entity designed to bind to the amplification product of the template. Typically, the entity is an oligonucleotide complementary to the amplification product. Compounds transducing a signal through a receptor of interest in the reporter cells cause expression of the polymerase. The polymerase is released from the cell, either as a result of secretion, or cell lysis. The polymerase then catalyzes a amplification of the template generating an amplification product, which can be labelled through incorporation of a labelled primer, or by incorporation of labelled nucleotides. The amplification product constitutes a secondary reporter, which modifies the tether of proximate complexes. Modification can be by hybridization or the result of binding between a labelling moiety on the amplification product (e.g., biotin) and a binding component of the tether (e.g., avidin). Complexes with modified tethers can be isolated from other complexes by sorting for the label on the amplification product (e.g., by FACS™).

j. Complexes with Combined Tag/Tethers

Compounds can also be screened as a component of library complexes bearing a linked tether and tag. The tether and tag can be part of a contiguous molecule, such as two domains of a protein, or can be joined, e.g., through a linker. For example, the tether can be a peptide and the tag an oligonucleotide. Both compounds to be screened and the combined tag/tether are attached to complexes by a cleavable linker. The same or different linkers can be used for compounds and the combined tag/tether. On cleavage of the compound, it can transduce a signal through a cellular receptor causing release of a reporter from a reporter cell, as described before. The combined tag/linker molecule is also released from the complexes, typically concurrent with or shortly after release of the compounds. Thus, in the present methods, the released reporter molecule does not modify a tether on a complex but rather on a combined tag/tether entity. Modified tag/tethers are separated from unmodified tag/tethers by virtue of the modification. The separate modified tag/tethers are then decoded to reveal the identify of the compound(s) causing release of the reporter molecule. For example, the combined tag/tether can be a fusion protein linking a phosphorylated peptide (tether) to an identifier peptide. A phosphatase reporter enzyme removes the phosphate group from the tether moiety allowing the fusion protein to bind to an antibody that specifically recognizes the dephosphoylated form of the tether. Modified fusion proteins can be separated from unmodified by affinity purification using the antibody as the affinity reagent. Modified fusion proteins are then decoded (e.g., by the Edman degradation method) to reveal the identity of compound(s) causing release of reporter molecule.

In another example, the combined tag/tether comprises a caged peptide linked to an oligonucleotide. A primary reporter removes the caging moiety of the peptide. Combined tag/tether can then be affinity purified using a receptor that specifically binds to the uncaged peptide. The oligonucleotide moiety of purified combined tag/tethers is then decoded.

II. Other Screening Methods

The methods described so far have screened library members comprising a compound, a tag and a tether, linked to a support and/or each other. One of the basic principles of this method, i.e., using a reporter molecule to modify a tether can also be exploited to screen other types of library.

A. Supports Bearing Compounds and Tethers but Lacking Tags

In one method, libraries are produced having members comprising a support bearing a compound to be screened (differing between different members) and a tether (the same for different members) but lacking a tag identifying the compound. Such libraries can be synthesized using a similar divide-and-pool approach as is employed for ESL libraries above, with the exception that all steps associated with synthesis of tags are omitted. Synthesis of nontagged libraries is also described by Lam, WO 92/00091 and Houghten, U.S. Pat. No. 4,631,211 and WO 92/09300. As will become apparent, it is important that the supports in such libraries bear sufficient compound both for activation of a receptor and for direct analysis of the compound to determine its identity.

Such libraries are screened by a generally similar approach to that employed for coded libraries. Specifically, the libraries are contacted with reporter cells in any of the formats discussed above. Compounds are then partially cleaved from the supports (i.e., the cleavage reaction does not proceed to completion). Cleaved compound diffuses to a receptor on reporter cells, where, if the compound has capacity to transduce a signal, the compound induces expression of a reporter molecule. The reporter molecule then modifies, directly or indirectly, the tether of the support of the compound transducing the signal.

Supports bearing modified tethers are separated using the same methods as described above. The identity of compounds is determined by direct analysis of residual compound borne by the supports. Such analysis can take the form of, for example, peptide sequencing, infra red analysis or mass spectrometry, depending on the nature of the compound.

B. Libraries of Cells Producing Compounds

In another method, the libraries have members comprising cells producing compounds to be screened. The compounds may be cell surface peptides encoded by the genome or a plasmid within the cell. However, more frequently, the compounds are secondary metabolites, such as polyketides, which are produced by the cells' enzymatic apparatus but which are not directly encoded by the nucleic acids within the cell. Preferably, the compounds are secreted from the cells producing them.

In some methods, cells producing the compounds to be tested are selected, or otherwise genetically modified, so that they express a cell surface tether. Such cells are then contacted with reporter cells in any of the formats described above. Active compounds from the library transduce expression of reporter molecules, which modify the tethers of cells producing the respective compounds in similar fashion to that described above. Further, cells bearing active compounds can be isolated by virtue of their modified tethers. The difference from the above methods arises in how compounds are identified once cells have been identified. For cells producing compounds representing secondary metabolites, the identity of a compound is determined by propagating a homogeneous culture of a cell having a modified tether, purifying the compound from the culture, and directly analyzing the compound (e.g., by peptide analysis, mass spectrometry or infrared spectroscopy).

In other methods (see FIG. 4), cells producing compounds to be tested need not have tethers directly affixed to the cells. In such methods, the cells producing the compounds to be screened are plated as an array of discrete colonies (e.g., on agar plates). The colonies are then replica plated onto a membrane, such as a nitrocellulose filter that has been pre-coated with a tether molecule that subsequently blocked against non-specific binding with BSA. If the compounds to be screened are not secreted by the cells producing them, the cells should be artificially lysed after transfer to the membrane. Transfer produces an array of compounds immobilized to the membrane in which the respective positions of the compounds in the array correspond to the respective positions of colonies on the original cell culture plates.

The membrane bearing the array of compounds is contacted with a culture of reporter cells having the characteristics described above. The compounds then diffuse from the filter matrix towards the reporter cells. The activating compounds then cause the reporter cells to respond by producing reporter molecules which, in turn, diffuse back towards the location from which the activating compounds originated. Active compounds in the array transduce a signal in the reporter cells causing release of a reporter molecules, which modifies the membrane at a site at, or proximate to, that at which the compound transducing the signal is attached. For example, if the reporter molecule is BirA and the membrane is impregnated with a substrate for BirA, the modification constitutes attachment of a biotin molecule to the membrane. The marked membrane is separate from the reporter cells and if, necessary, developed (e.g., by exposure to labelled avidin) to reveal the location of the markings. The membrane is aligned with the original plates of colonies producing the compounds and colonies aligning with marked regions of the membrane are picked. If markings are close together and precise identification of aligned colonies is difficult, picked colonies are rescreened by the same approach. Finally, a colony corresponding to a marked region is propagated to produce sufficient amounts of compound for direct analysis of the compound to reveal its identity.

C. Use of a Membrane as a Tether

Many of the principles discussed above, can be exploited in a further variation, in which complexes bearing compounds and tags are screened in an array format immobilized to a membrane. In this situation, the area of the membrane proximate to each complex effectively forms a tether for that complex. The membrane format is also effective for screening complexes having a compound, a tag and a separate tether.

In either situation, the array of compounds is provided on a membrane, such as the nylon or nitrocellulose membranes used in conventional blotting experiments. Discrete aliquots of each compound usually occupy discrete sites in the array, although some overlap of sites is permissible if several rounds of screening are to be performed. It is not necessary to know in advance which compound occupies which site in the array, or for the sites to form any particular geometric configuration.

Often the compounds are synthesized as ESL libraries (i.e., an aliquot of each compound is attached to a bead bearing a tag identifying the synthetic route of the compound). The ESL libraries may or may not have tethers of the kind described above. About $10^8$ monobeads can be immobilized on a membrane surface of 320 cm$^2$ (16×20 cm) with beads separated on average about 10 microns from their nearest neighbor. Beads can be deposited on the membrane suspended in sucrose buffer as a slurry under vacuum. Visible microscopy is used to check the distribution of beads on the membrane. If the distribution is uneven, more buffer is added to the membrane, and the beads are resuspended until a monolayer is achieved. Binding of the beads to the membrane can be strengthened by irradiation or chemical conjugation.

The membrane bearing an array of compounds is laid down on a surface of reporter cells of the kind described above, and compounds are released from the membrane. Sometimes first and second aliquots of compounds are attached by different linkers and only the first aliquot is released in the first round of screening. Released compounds diffuse into contact with cells, and active compound(s) transduce a signal through a cellular receptor resulting in release of a reporter molecule from reporter cells. The reporter molecule diffuses toward the membrane and modifies either the tether of the complex from which the active compound was released or a site on the membrane proximate to the location of the active compound. This depends on the selection of reporter molecule, and whether the complexes being screened have tethers. SEAP is a suitable reporter molecule to mark a membrane. SEAP is very stable once bound to a nylon membrane surface (Kirchhoff et al., *TIGS,* (June 1995)). The membrane is peeled off the agar overlay and developed for SEAP activity in NBT/BCIP buffer (pH 9.8) to visualize the region of the membrane containing active beads.

If the modification is designed to occur to the membrane, modified areas of the membrane are cut out and supports recovered. The supports can then, if desired be subjected to a further round of screening, which proceeds as the first round, except that the second aliquots of compound are released. If the modification is designed to occur on support-bound tethers, supports bearing modified tethers are isolated as previously described. If the supports still bear a second aliquot of the compounds, the supports can be subjected to a second round of screening before decoding of tags to reveal the synthesis route of active compounds.

D. Screening for Compounds Having Receptor Binding Activity

The strategy for identifying compounds that transduce a response through a receptor can be adapted to identify compounds that merely bind to a receptor irrespective of transducing activity. Libraries of compounds can be provided in the same format described above, (e.g., complexes comprising a support bearing a compound, a tag and a tether). The libraries are screened by contacting these primary complexes with secondary complexes. The secondary complexes comprise a support, such as a bead, a receptor (or a ligand-binding domain thereof), a ligand to the receptor and a reporter molecule. Beads used to support secondary complexes are sometimes referred to as reservoir beads in distinction from the library beads used to support compounds to be screened. Either the ligand or the receptor (but not both) is irreversibly immobilized to the support. The immobilized moiety is then specifically but reversibly bound to whichever moiety is not immobilized. That is, if the receptor is immobilized, it is reversibly bound to the ligand and vice versa. Optionally, multiple ligands can be bound to the same receptor or vice versa, thereby increasing the avidity of binding. Bivalent or higher multivalency is an advantage for ligand-receptor pairs having low affinity interaction since it reduces dissociation of pairs in the absence of competing compounds but does not prevent dissociation in the presence of a competing compound. Whichever moiety is not immobilized to the support is linked to the reporter molecule in such a manner that the combined molecule retains the functions of both of its constituents. For example, if the receptor is immobilized, the ligand is linked to the reporter, such that the ligand retains its ability specifically to bind to the receptor and the reporter retains its ability to report. The two components can be linked as a fusion protein or by chemical crosslinking, antibody capture on common fused epitopes, or attachment of several copies of each molecule to nano-supports, such as colloidal particles.

The format in which the receptor is irreversibly immobilized to the support is particularly useful when a soluble form of the receptor is not easily available, as is the case for seven transmembrane receptors and ion channels. In this situation, the support in the secondary complex can be a cell expressing the receptor on its surface.

After contacting the primary complexes with secondary complexes, compounds can be released from the primary complexes and diffuse into contact with the secondary complexes. A compound having affinity for the receptor, competitively displaces either the ligand or receptor (whichever is not immobilized) from the secondary complexes. The displaced ligand or receptor is linked to a reporter molecule, which after release from its secondary complex, is free to diffuse into contact with the primary complex from which the active compound was released and modify the tether of the same. (Intact secondary complexes are too massive to diffuse into contact with the tethers of primary complexes at significant frequency.) Other aspects of the screening method, such as suitable matrixes or wells for contacting primary and secondary complexes, methods of identifying complexes having modified tethers, and the variations described in Section I.6, are as described in other methods of the invention. More flexibility is possible in choice of reporter molecules because in the present methods it is not necessary that these molecules be proteins.

Figure 5:
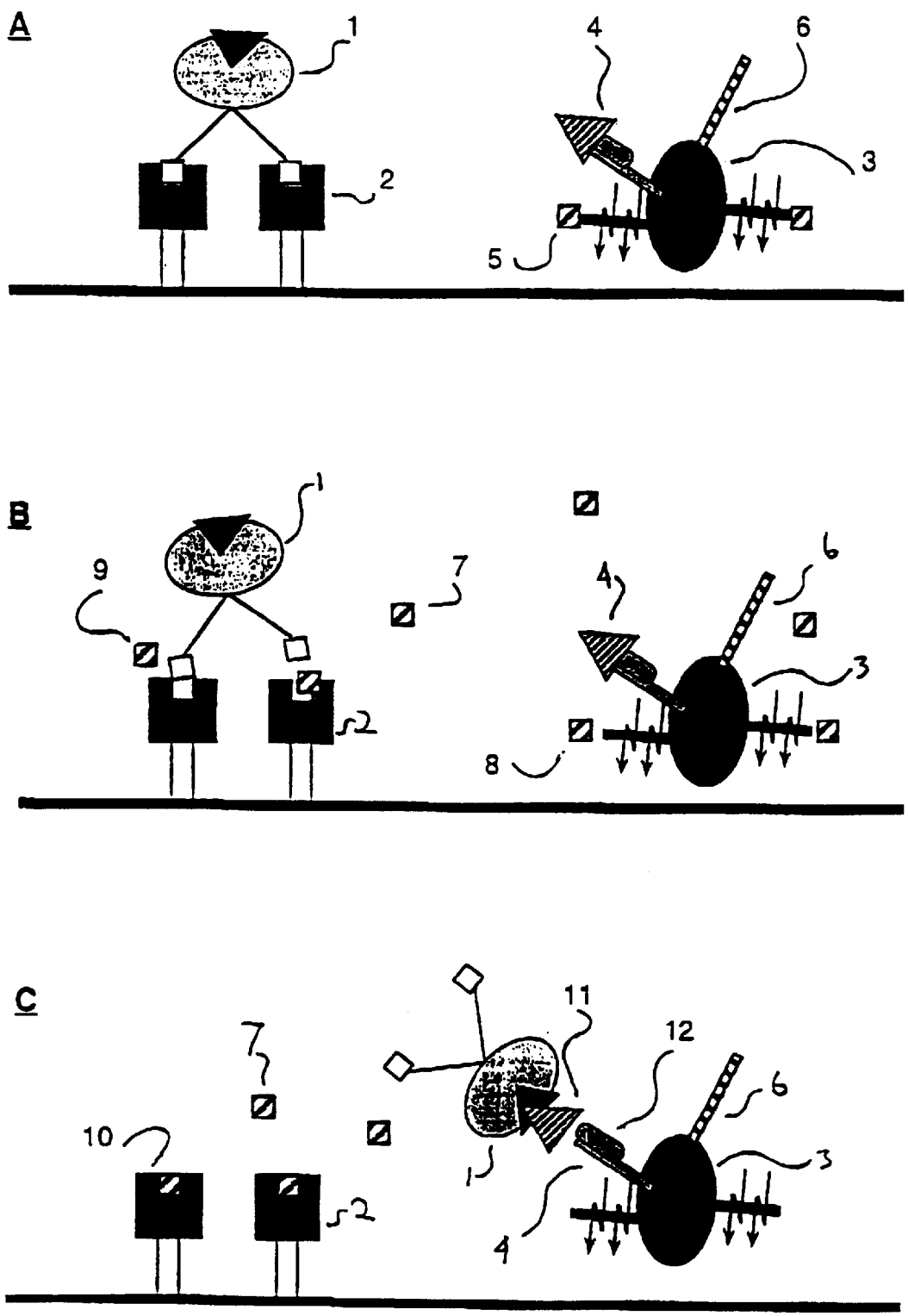
FIG. 5: Scheme for screening a library for compounds that bind to a receptor by a competitive binding assay.

FIG. 5 shows an exemplary competitive binding assay. Panel A represents the situation before compounds are released from supports. The reporter-fusion (1) is bound to its corresponding immobilized receptor pair (2). Nearby is a bead (3) comprising a tether (4), a compound on a cleavable linker (5) and a tag (6) correlating to compound (5). Panel B represents the events after the compounds are released (8). A compound having affinity for the receptor (7) diffuses from its support (3) and displaces the reporter-fusion (1) from the receptor pair (2). Panel C represents the soluble reporter fusion (1) acting on (11) the tether (6) leaving a modified tether (12).

As in other methods, the reporter molecule can modify the tethers of supports bearing active compounds indirectly through activation of a secondary reporter molecule. Thus, the amplification cascades described in Section I.6 are equally applicable to competitive binding formats with the modification that primary reporter is supplied as a fusion protein rather than being expressed by reporter cells. For example, a first reporter might be a site-specific protease fused to the target receptor bound to an immobilized ligand. Competition-mediated release of the protease fusion then allows the proteolytic release of a large amount of reporter two which is fused via a peptide containing the protease recognition site to a support, such as a bead. Reporter two then marks the supports of the primary complex. Thus, a stoichiometric release of reporter one results in a catalytically-amplified release of reporter two, thereby amplifying the response signal.

Figure 7:
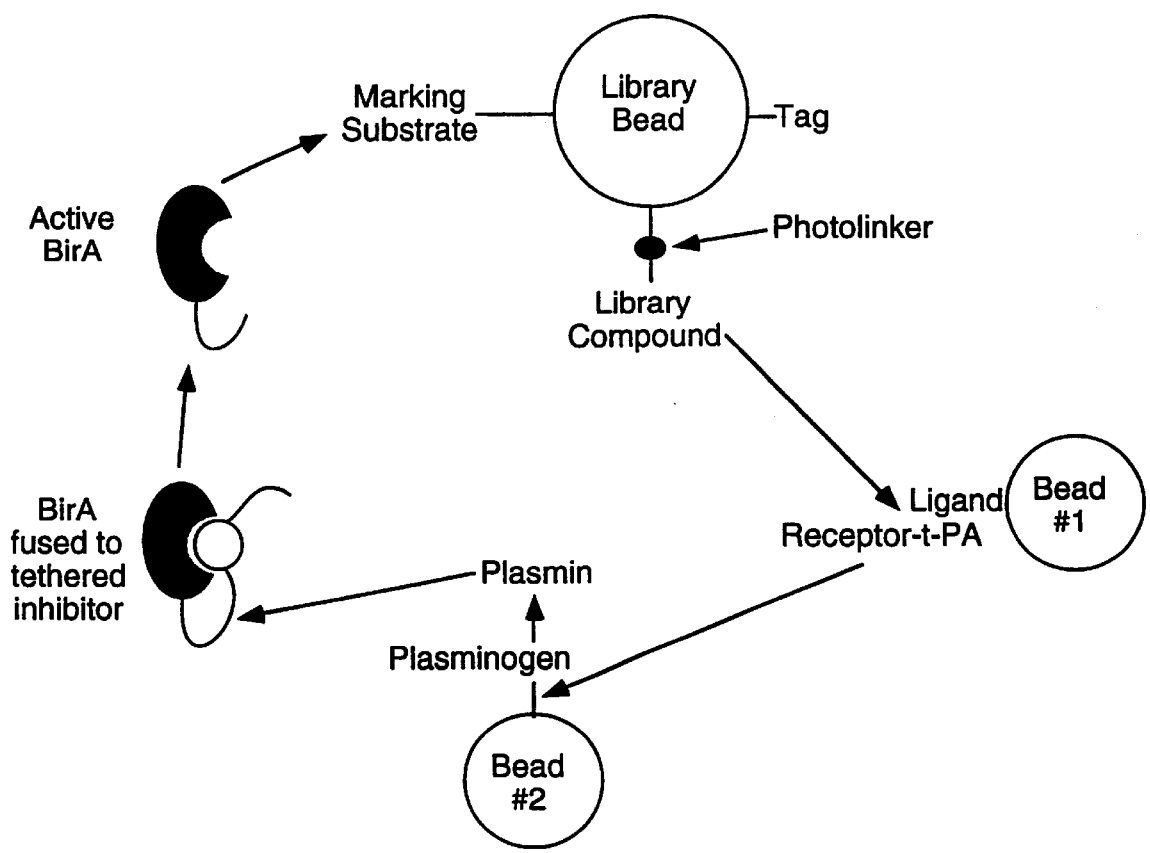
FIG. 7: Exemplary scheme for screening for receptor if antagonists by competitive dissociation of a receptor-reporter fusion from immobilized ligand.

An exemplary amplification reporter system for analyzing tether marking in a competition binding format is shown in FIG. 7. The library bead contains a library compound linked via a labile linker such as the photolinker, an encoding tag, and a tether. In this example, the tether is a peptide substrate for BirA. Close to the library bead are two other beads. Bead #1 is irreversibly bound to a ligand for the receptor under study, and a fusion protein comprising the receptor linked to tPA is reversibly bound to the ligand. Library beads carrying a compound that competes with the receptor-ligand interaction cause the dissociation of the receptor from bead #1, allowing the receptor-tPA fusion to diffuse over to bead #2. Bead #2 carries a tethered form of plasminogen that is activated by the receptor-tPA fusion to form plasmin. The plasminogen can be attached to the beads via antibodies specific for the "pro" peptide of plasminogen. Of course, either or both bead #1 or bead #2 can be replaced by the appropriate immobilized reagent(s) on the sides of the well in which the reaction takes place. Activated plasmin released by tPA cleavage is then be used directly as the tether marking enzyme, or can activate a tertiary reporter such as the BirA fusion protein described in Section I.6.

In another amplification format, the reporter molecule can be a ligand or other agonist (e.g., a synthetic short peptide) of a secondary receptor present on reporter cells of the kind described above. Release of a compound from a primary complex displaces a first reporter molecule from a secondary complex. The reporter molecule then diffuses into contact with a secondary receptor on a cell, and transduces a signal through the secondary receptor causing release of a second reporter molecule from the cell. The second reporter molecule then modifies the tether of a primary complex bearing the compound that displaced the first reporter molecule.

III. Screening for Inhibitors of Enzymes

Some of the principles underlying the methods of screening compounds for signal transducing capacity can also be exploited to screen compounds for capacity to inhibit a selected enzyme. In some such methods, the compounds to be screened are again provided as components of complexes that also bear tags serving to identify the compounds and a tether susceptible to modification. The tether is chosen to be susceptible to modification by the enzymatic activity to which it is desired to isolate inhibitors. Again, the tether is usually the same for all complexes in the library. Such libraries of complexes are produced by the same procedures as described above.

Compounds are screened for enzymatic activity by contacting the complexes bearing the compounds with enzyme in a matrix, such as agar or agarose. Before, concurrent with, or after contacting complexes with enzyme, the compounds are released from the complexes (e.g., by cleavage of a photocleavable linker). Release should occur after compounds have been incorporated into the matrix. Release can be partial or complete. If the enzyme is contacted with complexes before release of compound, it is desirable that the enzyme activity initially be substantially absent. This can be achieved by performing the contacting at low temperature, and/or in the absence of a cofactor. After release of compounds, the enzyme can be activated by raising the temperature or impregnating the matrix with the cofactor.

The matrix allows diffusion of the compound over short distances commensurate with the dimensions of the complex, but substantially prevents diffusion of the compound to neighboring complexes. After release, a compound diffuses forming a halo around the complex from which it was released. If the compound has enzyme inhibiting activity, the halo of compound protects the tether of the complex releasing the compound from modification by the enzyme. For compounds lacking such activity, the tethers of complexes releasing the compounds are modified by the enzyme. Thus, the result of contacting complexes with the enzyme is that a subpopulation of complexes have modified tethers and a second subpopulation have unmodified tethers and the second subpopulation is enriched for complexes that originally bore compounds with inhibiting activity. The probability of a tether undergoing modification is substantially higher (e.g., about 5–, 10, 50 or 100% higher) for complexes having compounds lacking inhibiting activity than for complexes having compounds with inhibiting activity. Complexes having unmodified tethers can be subjected to further rounds of screening using the same principles. Ultimately, individual complexes bearing unmodified tethers are isolated and the identity of compounds determined from the tags.

Selection of the tether is, of course, dependent on the nature of the enzyme for which isolation of inhibitors is desired. If the enzyme is a protease, the tether should be a protein including a site recognized by the enzyme. If the enzyme is a DNA polymerase, the tether should be a nucleic acid fragment capable of being extended by the polymerase. If the enzyme is a kinase, the tether should be a peptide having a site susceptible to phosphorylation. If the enzyme is a phosphatase, the substrate should be a peptide bearing a phosphate group.

Many of the variations and alternative described for screening for activating compounds are also applicable to screening for enzyme inhibitors. For example, the method can be practiced using supports bearing a tether and compound, but lacking a tag identifying the compound, provided the compound is present in multiple copies per support and is subject to only partial release from the support leaving sufficient residual compound for direct release. As a further example, compounds representing the products of secondary metabolism, can be screened for inhibiting activity when produced by cells that express a tether as a cell surface marker. Cells producing compounds and displaying a tether from their outersurface are contacted with enzyme in a matrix in the same manner as described above. Compounds are secreted, or otherwise released from the cells, and a compound having inhibiting activity protects the tether of the cell from which it was released from enzymatic modification. Cells having unmodified tethers are isolated, cloned by limiting dilution, and propagated to express large amounts of compounds having inhibiting activity.

In another variation, the enzyme for which inhibitors are to be identified does not modify complex tethers directly, but indirectly via a fusion protein comprising a reporter linked to a product of the enzyme. The fusion protein is immobilized to a support via reversible binding of a ligand to the product moiety of the fusion protein. The medium into which compounds are released from compounds contains the immobilized fusion proteins together with enzyme and substrate for the enzyme. In regions of the medium proximate to complexes lacking compounds with inhibitory activity, the enzyme metabolizes the substrate generating product. The product competes for binding with the immobilized fusion protein releasing some of the fusion protein to the medium. The fusion protein then modifies the tethers of proximate complexes. In regions of the medium proximate to complex(es) bearing a compound with inhibitory properties, released compound forms a halo around the complex preventing enzymatic activity in this region. The fusion protein is not released from its immobilized state and does not modify the tethers of proximate complexes. Complexes with unmodified tethers are separated from complexes with modified tethers, as above.

IV. Screening for Antagonists

The principles described above for screening for agonists of cellular receptors can be adapted to screen for antagonists. In one variation, complexes bearing compounds, tags and tethers are contacted with reporter cells with a receptor in the presence of a ligand to the receptor. The reporter cells contain a segment encoding a reporter molecule whose expression is coupled to signal transduction by the ligand through the receptor. In this situation, in cells proximate to complexes bearing antagonist compounds, the antagonist blocks signal transduction and modification of the tethers of complexes proximate to such cells does not occur. In other cells, proximate to complexes lacking antagonist compounds, the ligand causes signal transduction, the reporter molecule is expressed and released from the cells, and modifies the tethers of the complexes proximate to the cell. The result is a collection of complexes, some of which bear modified tethers and some unmodified tethers. Complexes bearing unmodified tethers are isolated, these being enriched for compounds having antagonist activity.

In a variation, the reporter cells have a DNA segment encoding a reporter molecule such that the reporter molecule is constitutively expressed and secreted. The reporter cells have a second DNA segment encoding an enzyme that is lethal to the cell whose expression is coupled to signal transduction through a cellular receptor by a ligand. Suitable lethal genes include the *Bacillus amyloliquefaciens* ribonuclease (Hartlet, *J. Mol. Biol.* 89 (1985)) and the *Bacillus amyloliquefaciens* ribonuclease expressed with or without its inhibitor, barstar. Another example of a lethal gene is the catalytic A fragment of diphtheria toxin (Tweeten et al., *J. Bacteriol.* 156, 680–685 (1983)). Expression of diphtheria toxin within yeast cells causes ADP-ribosylation of elongation factor 2, which leads to inhibition of protein synthesis and eventual cell death (Mattheakis et al., *Mol. Cell. Biol.* 12, 4026–4037 (1992)). A library of complexes having compounds, tags and tethers is contacted with reporter cells in the presence of the ligand. In cells proximate to a complex bearing a compound that is an antagonist, the antagonist blocks signal transduction by the ligand through the receptor. Accordingly, the lethal gene is not expressed and the cell survives. The cell constitutively expresses the reporter molecule which is released from the cell and modifies the tether of the complex which bore the antagonist compound. Conversely, in other cells that are not proximate to an antagonist compound (usually the majority of cells), the ligand transduces a signal through the receptor causing expression of the lethal gene and death of the cell. Expression of the reporter molecule is thereby terminated. Accordingly, the level of reporter molecule surrounding complexes lacking antagonist compounds is low, and the tethers of such complexes remain largely unmodified. Separation of complexes bearing modified tethers enriches for complexes from which antagonizing compounds were released. The identity of such compounds can be decoded from the tags.

V. Analog Compounds

The compounds isolated by the above methods also serve as lead compounds for the development of analog compounds. The analogs should have a stabilized electronic configuration and molecular conformation that allows key functional groups to be presented to the receptor in substantially the same way as the lead compound. In particular, the analog compounds have spatial electronic properties which are comparable to the binding region, but can be smaller molecules than the lead compound, frequently having a molecular weight below about 2 kD and preferably below about 1 kD. Identification of analog compounds can be performed through use of techniques such as self-consistent field (SCF) analysis, configuration interaction (CI) analysis, and normal mode dynamics analysis. Computer programs for implementing these techniques are available. See Rein et al., *Computer-Assisted Modeling of Receptor-Ligand Interactions* (Alan Liss, New York, 1989).

VI. Pharmaceutical Compositions

Transducing compounds identified by the above methods or analogs are formulated for therapeutic use as pharmaceutical compositions. The compositions can also include, depending on the formulation desired, pharmaceutically-acceptable, usually sterile, non-toxic carriers or diluents, which are defined as vehicles commonly used to formulate pharmaceutical compositions for animal or human administration. The diluent is selected so as not to affect the biological activity of the combination. Examples of such diluents are distilled water, physiological saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

EXAMPLES

1. Synthesis of Bead Complexes Bearing Peptides, Identifier Tars and Tethers

Polystyrene beads (10 micron diameter) containing reactive amines were treated simultaneously with the two acylating reagents shown in FIG. 8. 1 is a photocleavable linker upon which a compound to be screened is synthesized and 2 is a permanent linker which provides the anchor point for identifier tag synthesis. The molar ratio of 1 and 2 coupled to the beads is about 750:1.

The resulting beads were treated with piperidine to remove the Fmoc protecting group and the sequence Phe-2-Nal-Gly was prepared by solid-phase peptide synthesis. In a typical coupling reaction 0.075 M Fmoc-protected amino acid was treated with 0.10 M HATU and 0.30 M DIEA. The mixture was applied to the beads and the reaction allowed to proceed 1 hr at room temperature. At the end of each coupling cycle, excess reagents were washed away and the Fmoc-protecting group was removed by treatment with piperidine (20%, 10 min).

A 10 $\mu$m bead complex was created by synthesizing onto beads (differential of 727:1) a single sequence 38 mer DNA tag and a single sequence peptide trimer coupled to a photolinker. The sequence of the DNA tag is 5'-CTCC CGG CCA ATT GTT TCA CAG CGT TAT GCT CCG CACC-3' (SEQ ID NO:14), the italics indicating the identification code for the trimer. The oligonucleotide tag was synthesized using standard DNA coupling techniques (detritylation with TCA; tetrazole-catalyzed phosphitylation; capping with acetic anhydride; oxidation with iodine in acetonitrile/water). The sequence of the trimer peptide on photolinker was (from N to C) Phe-2-Nal-Gly. After synthesis of both peptide and oligonucleotide, the beads were treated sequentially with piperidine/DMF (2:8 for 2 hours), ethylenediamine/ethanol (1:1 for 4 hr), and TFA/water/TPS (95:3:2 for 1 hr) to deprotect fully both the peptide and oligonucleotide chains. 7-deaza analogs of adenine and guanine were used to avoid TFA-mediated DNA strand cleavage during the final acid deprotection step.

For attachment of a tether, 2 mg beads was aliquoted into a 1.5 ml eppendorf tube. Streptavidin (Gibco BRL) was passively absorbed to the 2 mg of the beads @ 1.0 mg/ml in 0.01% azide/phosphate-buffered saline PBS) for two hr at room temperature on a shaker. The beads were washed twice with 1 ml PBSTB [PBS, 0.05% Tween20 (Sigma), 0.1% BSA (USB, Fraction V, RIA grade), 0.01% azide] by centrifuging at 14 krpm for 1 min, removing the supernatant from the bead pellet and resuspending the pellet. The beads were then blocked in 1 ml PBS, 0.05% Tween20, 1.0% BSA, 0.01% azide, overnight at 4° C. on a shaker. The beads were washed 2× as before. Next, a soluble biotinylated peptide, YGGFLGGGGSK[biotin] (SEQ ID NO:15), at 10 $\mu$M, was bound to the streptavidin on the beads in 250 $\mu$l PBSTB for one hr at room temperature on a shaker. The modifiable tether is thus, YGGFLGGGGSK[biotin]-streptavidin and synthesis of the complex is complete.

The beads were washed 1× in PBSTB as before, resuspended in 200 µl PBSTB and stored at 4° C. The beads were counted in a hemocytometer and the concentration was 60,000 beads/µl.

2. Decoding DNA Identifier Tags

This examples shows that DNA identifier tags can be decoded after exposure to typical conditions in a tether marking assay. Two aliquots of 3×10$^5$ beads (5 µl of stock) were added to 1 ml of cell culture assay media and dispensed separately onto two monolayers of adherent CHOK1 cells growing in 6-well cell culture plates (Limbro, Flow Laboratories). The monolayers had 2.6×10$^6$ cells/well. The cells had been grown in DMEM/F12, 10% FBS (Gibco), 1% Pen/Strep Fungizone (Bio Whittaker) and then immediately prior to the assay washed twice with D-PBS (Gibco BRL). The assay media was DMEM/F12 (Gibco) containing 10 mM L-Homoarginine (Sigma), 1% BSA, 1% Pen/Strep Fungizone (Bio Whittaker).

Two plates, both containing the same number of beads and cells in 1 ml media, were covered with microplate press-on adhesive sealing films (Packard). Then one plate was photolyzed (360 nm) for 30 minutes @ 8.0 mW/cm$^2$. The second otherwise-identical plate, was left at room temperature-exposed to only ambient light for 30 minutes. The sealing films were removed and lids placed back on the plates. Both plates were then placed into a 37° C. cell culture incubator for six hours. (Six hours is longer than typically required in a bead marking assay.) The beads were then pipetted off the monolayers and the cells discarded. The beads were pelleted and washed twice with 1 ml PBSTB. The beads were resuspended in 1 ml PBSTB and stored at 4° C. overnight.

The next day the beads were sorted for single beads. The Becton Dickinson FACStar™ Plus machine was used to sort, out of the bulk bead populations, single beads into 96-PCR tube arrays. After the sort, there were 2 plates of 96 PCR tubes each. One plate held tubes containing single beads that were not photolyzed and the other plate held tubes containing single beads that were photolyzed PCR was performed on 8 single beads, 4 from each plate.

PCR cocktail was prepared to allow for 100 µl per reaction, plus 100 µl for a negative control (no complexes) and 100 µl for a positive control (untreated complexes). The cocktail recipe per reaction (100 µl) was 10 µl 10×Thermo Buffer (Promega), 10 µl 10×stock dNTP U (10× is 2.0 mM dATP, dCTP, dGTP and 4.0 mM dUTP from Pharmacia) (dNTP U is used instead of dNTP T to help alleviate contaminating sequences), 10 µl 10×Stock Mg buffer (10× is 20.0 mM) (Promega), 10 µl 10×Stock Primer 4861 (10× is 10.0 µM), 10 µl 10×Stock Primer 4860 (10× is 20.0 µM), 10 µl of 10×Stock Primer 4246 (10× is 30.0 µM), 38 µl sterile ddi H$_2$O.

After mixing, 1.0 µl of uracil deglycosylase (UDG) 1.0 unit/µl (GibcoBRL) was added per 100 µl and mixed well. 1.0 µl Taq DNA polymerase at 5.0 units/µl (Promega) was added and mixed well. 100 µl of cocktail was added to each reaction tube containing a single bead, and to the negative and positive controls. The tubes were topped with three drops of mineral oil and capped.

A 3-primer scheme was employed for optimal PCR with minimal prime-dimer artifacts. Primer-dimer and other artifacts might occur due to the length of the complementary primer 4861, a 46mer, in comparison to the DNA tag itself which is shorter, a 38mer. By off-setting the PCR reaction with another, 21mer complementary primer, the occurrence of primer-dimer was minimized. Because the 21mer does not contain the sequencing primer annealing site as does the 46mer, the 21mer does not contaminate the PCR product for direct product sequencing.

The sequences of the primers are as follows:
4246 (homologous primer) 5'-TGA GCC GGC ACT CCC GGC CAA-3' 21mer (SEQ ID NO:17)
4860 (complimentary primer1) 5'-ACG CTG ACC CGT GGC GGA GCA-3'21mer (SEQ ID NO:18)
4861 (complimentary primer2) 5'-TTA CGG GCT AGC CAT AGG GCA GAA GAC GCT GAC CCG TGG CGG AGC A-3' 46mer (SEQ ID NO:19)

The expected full-length PCR product from amplification from these primers is an 83mer.
5' TG AGC CGG CAC TCC CGG CCA ATT G TT TCA CAG CGT TAT GCT CCG CCA CGG GTC AGC GTC TTC TGC CCT ATG GCT AGC CGG TAA 3' (SEQ ID NO:20)

Small Pont=primer appended sequence
Bold=13 base code region available for compound identification
Italics=6 base code region used in present example

| Thermocycling was carried out on an MJ Research cycler using the following profile: | |
|---|---|
| 37° C. | 30 minutes |
| 94° C. | 10 minutes-for UDG activation and inactivation |
| Thermocycle 2 times: | |
| 45° C. | 2 minutes |
| 72° C. | 1 minute |
| 94° C. | 30 seconds |
| Thermocycle 1 time: | |
| 45° C. | 2 minutes |
| 72° C. | 1 minute |
| Thermocycle 34 to 40 times: | |
| 94° C. | 20 seconds |
| 62° C. | 30 seconds |
| 72° C. | 30 seconds |

Hold at 72° C. until processed

The PCR products were processed using Qiagen PCR clean up columns. After processing the PCR product was analyzed by PAGE on a ten-well 1.0 mm, 10%, 19:1, 5% cross-linker polyacrylamide TBE gel. A Gibco BRL 10 base pair ladder was used as a standard for the PCR samples. 10 µl of each PCR sample was loaded with 2 µl of loading buffer (30% glycerol v/v, 0.5% bromophenol blue w/v, 1% SDS w/v). The gel was run at 120 V for 1.5 hr. The gel was stained with ethidium bromide in water for 15 min at room temperature and photographed. The gel showed an 83-bp PCR product in each lane. This experiment was successful: Both sets of beads, containing full complex, incubated for six hours with cells and cell products, +/−photolysis, showed clean, 83mer PCR-amplified products.

1.0 pmol of each of the products was then directly sequenced using 30 pmols of a reverse sequencing primer, 5'-TTA CGG GCT AGC CAT AGG GCA-3' (SEQ ID NO:21) to verify the correct code region (identifier tag). Direct sequencing of these products was by a slightly modified version of the traditional T7 DNA polymerase methodology. The sequences on all the single beads were verified as correct, each revealing the code TCA CAG.

Instead of directly sequencing the PCR products, the products can be cloned into the pBS KS(+) vector at the EcoRI and SpeI sites. Complementary sites can be generated from the full-length PCR products by digesting the products with MunI and NheI. Once the vector and digested PCR products are ligated, the *E. coli* 24 strain ARI 837, (F′, proAB, lacIq, lacZδM15, Tn10(tetR) // recA::cat, ung, endA1, nupG, araD139, δ(araABC-leu)7696, thr, δlacX74, galU, galK, hsdr, mcrB, rpsL(strA), thi) can be transformed with the plasmid. The transformed bacteria can then be plated and colonies chosen for plasmid preparation and sequencing. The cloning method is useful for decoding when a pool of beads containing multiple tags is amplified by PCR in one reaction. The direct sequencing method is useful for single bead decoding.

3. Photolytic Release of Compounds from Supports a. Photolysis Without Impairment of Reporter Cells In a tether-marking assay, the cells need to survive photolysis of compounds from beads so that the cells adequately express the reporter gene in response to signal transduction. One reporter gene is secreted alkaline phosphatase (SEAP), a soluble variant of HPAP. SEAP is available from Clontech, (*Gene* 66, 1–10 (1988)). A SEAP cassette, driven by a constitutive CMV promoter was stably transfected into adherent CHOK1 cells. These cells were then clone-sorted into 96-well cell culture plates (Falcon) using the Beckton Dickinson FACStar™ Plus machine. Individual clones were tested for SEAP production using the Tropix Chemiluminescent Assay Kit. The results of the assay were read in a Packard TopCount machine from which SEAP activity was read in units of counts per second (CPS). CPS were then converted to units of SEAP using a purified SEAP protein standard assayed in parallel. The best clone isolated, called 3B9, produced 0.52 units of SEAP in four hours when grown to a 90% confluent monolayer containing $2.6\times10^6$ cells in one ml media.

Monolayers of the 3B9 cells were tested for their ability to withstand light exposure. The 3B9 CHOK1 CMV-SEAP cells and a pool of CHOK1 (without SEAP) cells were seeded into 2 wells each on 2, 6-well cell culture plates. All were seeded with $1\times10^6$ cells/well. The cells were grown overnight in 2 ml DMEM/F12 (Gibco) with 10% FBS (Gibco), 1% Pen/Strep (Bio Whittaker). After 24 hr growth with $2.6\times10^6$ cells/well, all cell monolayers were washed 2× with 5 ml D-PBS (Gibco) and 1× with 2 ml DMEM/F12 SF (DMEM/F12, 10 mM L-Homoarginine (Sigma), 1% BSA (USB Fraction V, RIA grade), 1% Pen/Strep). 1 ml of the same SF media was then pipetted onto each monolayer. The plates were covered with microplate press-on adhesive sealing films (Packard).

One plate of cells was exposed to 360 nm light at 8.0 mw/cm$^2$ for 30 min. The other plate was exposed only to ambient light for 30 min. Exposure to 360 nm light for 30 min at 8.0 mW/cm$^2$ releases an ample concentration of soluble compound from bead complexes.

After 30 min, the sealing films were replaced by the lids for the plates. The plates were placed into a 37° C. cell incubator. 100 μl of supernatant was removed from each monolayer at different time points from 0–6 hr incubation. The supernatants were tested for SEAP production/activity using the Tropix Chemiluminescent Assay Kit. At each timepoint, the 360 nm light-exposed SEAP cells produced the same active amount of SEAP as the non-exposed cells.

b. Accessibility of Complexes to Photolysis in Nanowells

An array of nanowells is one assay format for placing a library of complexes in proximity to reporter cells to allow diffusion over a short distance (the nanowell) but retain small numbers of the cells and complexes in restricted positions. A nanogrid is an array of 40,000 wells, each of dimensions 100 μm×100 μm×100 μm and capable of holding 1 nl of fluid. 100 cells and 100 beads can be loaded in each single well. An individual grid has dimensions 2 cm×2 cm and provides a high-throughput screening tool. Given a starting amount of compound on the complexes of about 10 fmol, a desired concentration of about 1–10 μM compound in the wells, a 1–10% release of compound from complexes provides adequate soluble compound in the wells.

10 μm bead complexes were produced as described in Example 1 above at a concentration of 93,000 beads/μl. In a first experiment, photolysis of the tripeptide from the beads was performed in 400 μl DMEM/F12 (Gibco BRL) per mg ($5\times10^6$) of beads in 6-well plates (surface area 7.5 cm$^2$). 30 min photolysis at 360 nm and 8.0 Mw/cm$^2$ gave 12% release of peptide. Release of peptide in nanowells was tested using the same beads to make sure 10% of peptide was still released.

One test and two controls were set up as follows.

0.8 mg bead complexes (4–106) in 1 ml DMEM/F12 was added to the top of a nanogrid. The beads were allowed to settle through the media into the nanowells on the grid for 45 min. There was an average of 85 bead complexes in each nanowell after settling. 1 ml DMEM/F12 was removed from the top of the grid. The only remaining volume was that inside the wells. As there are 40,000 wells on the grid, each holding 1 nl, the total volume on the grid is 40 μl. As a control for photolysis volume, 0.8 mg ($4\times10^6$) bead complexes were added to 1 well of a 96-well plate (Falcon) in 40 μl of DMEM/F12. The other assay control was 1 mg ($5\times10^6$) bead complexes added in 400 μl of DMEM/F12 to one well of a 6-well plate (Limbro, Flow Laboratories). Plates were all covered. The nanowell grid was covered with a glass coverslip, the 96-well plate and 6-well plate were covered with microplate press-on adhesive sealing films (Packard). All three plates were photolyzed for 30 min with 360 nm light at 8.0 Mw/cm$^2$.

The beads and photolysis supernatants were recovered from the plates and saved for HPLC analysis to determine % peptide release, i.e., how much soluble peptide was released and therefore present in the photolysis media. The supernatants were diluted 1:50 and analyzed in a Dynamax microsorb reverse phase HPLC. The column was a C8–5 μm particle size, 4.6 mm diameter×25 cm length. Flow rate was 1.0 ml/minute.

HPLC results showed that release of peptides from beads in the nanowells was 9.4%, similar to the 11.8% release from beads in 6-well plates. The release from the 96-well plate volume control was only 5.4%. These results indicated that a large surface area for better light exposure is more important for efficient photolysis than a large volume of photolysis media. Thus, it is concluded that adequate concentrations of soluble compound can be achieved from photolysis in a nanowell format.

4. Expression of Reporter Genes a. Production SEAP by Agonist Stimulated Reporter Cells A transfected CHO-Ki cell line was constructed containing the cholecystokinin b (CCKb) receptor and a reporter construct consisting of 6 copies of the consensus cAMP response element (Arias et al., *Nature* 370, 226–229 (1994)), a minimal tk promoter, and the SEAP gene (Clontech). The cell line was grown in Dulbecco's modified Eagle medium/ Nutrient Mixture F12 (DMEM/F12) containing 5% Fetal-Clone II (Hyclone, Logan, Utah) supplemented with penicillin, streptomycin, and amphotericin B. The cells were transferred to serum-free medium prior to measuring SEAP activity.

Cells were washed twice with PBS and resuspended to a final concentration of $2\times10^6$/ml with DMEM/ F12. Each well of a 48-well plate was seeded with $2\times10^5$ washed cells at 37° C., overnight. The wells were washed once with PBS.

100 nM CCK solution with DMEM was prepared and serial diluted 1:3 4 times. 200 μl diluted CCK solution was added per well. Then 200 μl/well DMEM/F12 was added to negative control wells. The wells were incubated at 37° C. overnight. 100 μl supernatant was transferred from each well to a Topcount Assay Plate. 100 μl assay buffer and 100 μl of 1× reaction buffer from Tropix Phospha-Light Kit was added and incubated at room temperature for 25 min on a shaker.

The plate was read with a Topcount luminometer (Packard). At 33 nM CCK, the reporter cells secreted 23-fold more SEAP than the negative control wells without CCK induction.

b. Activation of Cells in a Nanogrid Format

Murine lymphoid cell line Baf/3 expressing the human thrombopoietin receptor (huTPOr) linked through the fos transduction pathway to the luciferase gene (fos promoter-lux) was used in this example. These cells, termed, Baf/3 huTPOr/fos/lux, respond to the presence of thrombopoietin (TPO) or of a thrombopoietin mimetic (Cwirla et al., *Science* 276, 1696–1699 (1997)) with the production of luciferase which is detectable and quantifiable by measuring the light emitted after addition of its substrate, luciferin.

Baf/3 huTPOr/fos/lux were grown in the following medium and conditions: RPMI 1640; Hepes 25 mM; 10% fetal bovine serum; 3% WEHI-3 supernatant and antibiotics at 37° C. in 5% CO2. Before the assay, the cells were starved of WEHI-3 supernatant by transferring them to a medium consisting of RPMI 1640; Hepes 25 mM; 10% fetal bovine serum; 0.03% WEHI-3 supernatant and antibiotics for 12–18 hr. The cells were washed in assay medium (RPMI 1640; Hepes 25 mM; 10% FBS) and adjusted to a concentration of $2–10^6$ cells/ml for the standard assay and $1\times10^7$ cells/ml for the nanoreactor assay. In the standard assay, 50 μl assay medium was added to each well, followed by 10 μl 2 nM TPO agonist (Cwirla et al., Science, supra). 50 μl cells was added and the plate transferred to 37° C. for 2 hr.

In the nanogrid assay, a dam and gasket were fastened to a nanogrid having 40,000 cubic wells. 500 μl of the $1\times10^7$ cell/ml preparation was added in the cavity formed by the dam. Cells were left to sediment for 30 min. The fluid above the grid was decanted and replaced with 500 μl 200 pM TPO agonist for 10 min. Thereafter, the dam was removed, a dialysis membrane (1000 or 12000 MWCO) was overlayed on the grid and the dam reassembled. The nanoreactor was transferred to 37° C. for 2 hr.

After incubation, 100 μl of substrate was added to each well of the standard assay. The nanoreactor was disassembled and cells flushed out of the grid. Cell concentration was adjusted to $1\times10^6$/ml. 100 μl of this cell preparation was added to separate wells of the 96-well plate and substrate was added as for the standard assay. Light emission was measured on a Packard Topcount luminometer. Assays were done in triplicate and reported as average and standard deviation. The response of cells was about 5000 CPM for both the cells in the 96-well assay format and the cells in the nanogrid format The results demonstrate that cells can be activated in the nanoreactor to a level comparable to that achieved in the standard 96-well assay.

c. Expression of a Secreted Acid Phosphatase Reporter in Yeast (1) Yeast Strain Construction The strain used in these experiments is designated ARY84 (Mata prc1-407 prb1-1122 pep4-3 leu2, 3-112 ura3-52 trp1 far1::ura3 Δhis3::APT2 FUS1::HIS3 Δste2::ura3 Δsst2::ura3 Δpho5::TRP1 LEU2::pCMGy64(::FUS1-PHO3) [pRS416(URA3)-STE2]. This yeast is engineered to grow in the presence of an agonist, and also to secrete acid phosphatase as a result of agonist stimulation. The yeast strain used in these experiments bears a mutation in the SST2 gene to enhance sensitivity to agonist, an inactivating mutation in the FAR1 gene to allow growth in the presence of agonist and an inactivating mutation in the HIS3 gene. The FUS1 gene promoter stimulates transcription of two reporter genes. The first reporter gene is HIS3. 3-aminotriazole can be used to titrate out the background activity of the HIS3 gene product resulting in growth arrest due to histidine starvation. Stimulation of HIS3 transcription from the FUS1 promoter overcomes the inhibitory effect of 3-aminotriazole, allowing growth of agonist-stimulated yeast cells. The second reporter gene is PHO3 (which was obtained by PCR from yeast genomic DNA). This gene encodes secreted yeast acid phosphatase (see Johnston & Carlson, in *The Molecular and Cellular Biology of the Yeast Saccharomyce*, (eds. Jones et al., CSHP, 1992) Vol. 2, Ch. 5). STE2 encodes the yeast α-factor receptor. The mutation in the phos gene reduces the background of acid phosphatase secreted by the yeast, though this mutation may not be necessary.

(2) Secretion of Acid Phosphatase from Yeast in Response to α-Factor

α-factor is the natural peptide agonist of the yeast α-factor receptor. The term "Growth selection" refers to growing the yeast in a defined medium (e.g., synthetic complete) (see Rose et al., *Methods in Yeast Genetics: A Laboratory Course Manual* (CSHLP, 1990)) lacking histidine and containing sufficient 3-aminotriazole to inhibit growth such that yeast only grow when the HIS3 gene product is expressed from the FUS1 promoter following stimulation of the STE2 receptor by α-factor. Lack of growth selection is achieved by leaving out the 3-aminotriazole and adding histdine.

Acid phosphatase activity in the yeast growth medium was quantitated using a calorimetric assay with the substrate para-nitrophenyl phosphate (pNPP), measuring the appearance of yellow color (Payne et al., *Gene* 163, 19–26 (1995). When yeast were grown under various growth conditions (+/−saturating (500 nM) concentrations of α-factor, between 26% and 69% of the total acid phosphatase activity is secreted into the medium (Table 1).

TABLE 1

Secretion of acid-phosphatase activity into the medium by ARY84

| Time (Hrs) | alpha-factor | Growth Selection | % of total activity in medium |
|---|---|---|---|
| 24 | − | − | 26 |
| 24 | − | + | 49 |
| 24 | + | − | 69 |
| 24 | + | + | 63 |

When ARY84 is grown in the presence of 500 nM α-factor in the absence of growth selection (i.e., yeast grows irrespective of whether α-factor is added) there is a 16–20 fold increase in acid phosphatase activity in the medium after 24 hr compared to yeast grown under identical conditions in the absence of α-factor (Table 2).

TABLE 2

Acid phosphatase activity in the medium after growth of ARY84 under various conditions for 24 hours. Activity is in $OD_{405}$ units/minute utilizing the pNPP assay described in Payne et al (1995)

| | | Clone Number | |
|---|---|---|---|
| selection | alpha-factor | #1 | s3 |
| − | − | 0.003238 | 0.0061237 |
| − | + | 0.0648085 | 0.1000857 |

TABLE 2-continued

Acid phosphatase activity in the medium after growth of ARY84 under various conditions for 24 hours. Activity is in $OD_{405}$ units/minute utilizing the pNPP assay described in Payne et al (1995)

| selection | alpha-factor | Clone Number #1 | s3 |
|---|---|---|---|
| + | − | 0.0018188 | 0.0017428 |
| + | + | 0.0127902 | 0.0289228 |

When ARY84 is grown with growth selection there is a 32–58 fold increase in acid phosphatase activity in the medium after 48 hours compared to yeast grown under identical conditions in the absence of α-factor (Table 3).

TABLE 3

Acid phosphatase activity in the medium for ARY84 grown under "growth selection" conditions (i.e. lacking histidine, +10 mM 3-aminotriazole). Activity is in $OD_{405}$ units/minute utilizing the pNPP assay described in Payne et al (1995)
pNPP acid phosphatase assay, 48 hr. culture medium

| clone | No alpha-factor | 500 nM alpha-factor | Induction ratio |
|---|---|---|---|
| #1, + sel. | 0.001780952 | 0.05767619 | 32.4 |
| s3, + sel. | 0.001809524 | 0.106247619 | 58.7 |

These results show that in ARY84 secretion of acid phosphatase is stimulated by the addition of α-factor.

d. β-Galactosidase as a Reporter in Mammalian and Yeast Cells

For expression in mammalian CHO K1 cells, the *A. niger* gene for secreted β-galactosidase was cloned into a generic expression plasmid, (pAlpha+, T8, 12CA5, KH (see Koller et al., Analytical Biochem., 250, 51–60 (1997)) such that the native *A. niger* signal sequence was substituted by the mammalian T8 signal sequence, (MALPVTALLLPLALLLHAARPD); (SEQ ID NO:22). In this plasmid, named pCMG68, expression of the β-galactosidase gene was driven by the constitutive SR Alpha promoter which achieves high levels of secreted beta-galactosidase expression.

CHO K1 cells were transfected with pCMG68 and grown in selective media containing 1 mg/ml G418. Once activity of the transfected pool was established by addition of X-gal to pooled supernatant, individual clones were sorted into 96-well microtiter plates and grown for 7–14 days in selective media with frequent changes in media to promote cell growth.

β-galactosidase activity of individual clone supernatants was measured using the Galacton Star Assay (Tropics) using 24–48 hr supernatants. Ideally, 33 μl of cleared clone supernatant was added to 100 μl Galacton Star Mix (standard concentration) in Ph 6.15 MES at 50 mM or Ph 4.75 acetic acid at 50 Mm and allowed to react for 30–45 min at 37° C. in a black Microflor B plate (Dynatech). The plate was counted in a Packard Topcount machine. Typically 33 μl supernatant gave 100,000–500,000 counts per sec after a 30 min reaction.

For testing secreted β-galactosidase at its optimum Ph range (*A. niger* secreted beta-galactosidase appears to have a Ph optimum <Ph 4.75), an ONPG (2-nitrophenyl β-D-galactoside hydrolysis assay was used. As in the Galacton Star™ Assay, 33 μl of cleared supernatant was added to 917 μl 50 Mm citric acid buffer Ph 3.0 containing 0.8 mg/ml ONPG. The mix was allowed to react for 45 min at 30° C. and was then stopped by adding 500 μl M NaCO3. β-galactosidase activity was then determined as a function of ONPG hydrolysis by measuring the A420 of the solution. At 50 Mm citric acid, Ph 3.0, the secreted β-galactosidase activity was about six-fold higher than in 50 Mm MES buffer at Ph 6.15, and was about 15-fold higher than the same reaction run in 50 Mm MOPS buffer at Ph 7.2.

A second expression system links the *A. niger* secreted β-galactosidase gene to the yeast mating pathway/FUS1 promoter induction system. Using the integrating beta-galactosidase encoding plasmid pCMGy69 in concert with the yeast alpha factor receptor (STE2) encoding plasmid, PRS416-STE2 (centomeric), a yeast strain designated ARY 110 was produced with the following genotype; (far1 his3 sst2 FUS1-HIS3 FUS1-sBeta-Gal STE2). Tests for β-galactosidase activity using the substrates listed above, showed high levels of α-factor-inducible secreted β-galactosidase activity was observed in yeast cell supernatants of the β-factor-induced ARY 110 strain, but little beta-gal activity was observed in uninduced cultures of ARY 110.

When induced using the yeast mating pheromone peptide known as alpha-factor, beta-galactosidase activity levels up to 79 fold over non-induced levels were observed in the supernatants of ARY110 cultures. This demonstrates that in yeast, an inducible, receptor- transduction-mediated, secreted β-galactosidase reporter gene product can be actively produced.

e. Cre Reporter System

To regulate Cre function, the structural gene was placed under the transcriptional control of the NFAT promoter, the mouse mammary tumor virus (MMTV) promoter, and a synthetic promoter containing 6 copies of a cAMP response element (6cre). The NFAT construct was introduced into Jurkat cells along with a reporter plasmid containing from 5' to 3', a CMV promoter, a puromycin-resistant sequence flanked by loxP sites, and a luciferase coding sequence. A stable clone was isolated and then characterized. The cells were stimulated with ionomycin and a phorbol ester for 24 hr, and the luciferase activity was measured and compared to unstimulated cells. Luciferase activity increased about 2-fold compared with untreated cells, and was inhibited by cyclosporin. The response was also compared to that of a stable clone expressing luciferase directly from the NFAT promoter, and it was found that the stimulated luciferase activity of the NFAT-Cre clone was 40-fold higher than the NFAT-Luc clone.

To show that Cre recombinase functions in CHO reporter cells, a cell line was stably transfected with a construct containing from 5' to 3', a CMV promoter, a puromycin-resistance encoding sequence flanked by loxP sites and a luciferase coding sequence. Transient transfection of this cell line with a plasmid expressing Cre recombinase from the strong CMV promoter resulted in a 50-fold increase in luciferase expression. A similar experiment was performed with a CHO cell line transfected with a β-galactosidase reporter plasmid in which the β-galactosidase coding sequence was interrupted by a neomycin gene cassette flanked by frt sites, recognition sites for the Flp recombinase. Transient transfection of this cell line with a plasmid expressing Flp resulted in a 1000-fold increase in beta-galactosidase activity).

To show that Cre recombinase functions in yeast, Cre was placed under the yeast GALL promoter and transformed into a strain containing a URA3 gene flanked by loxP sites. Cells were grown in raffinose-containing medium, and the Gal1 promoter was induced by adding galactose. After 15 minutes of induction, over 60% of the yeast cells had undergone recombination and lost the URA3 marker. By 30 min, over 90% of the cells in the culture had recombined.

5. Tether Marking Assays a. Direct and Indirect Marking of Tether with SEAP

The following experiments illustrate two methods of marking a tether using SEAP. The first shows that SEAP expressed and secreted from transfected CHOK1 cells can directly mark a peptide tether on a bead complex. The second experiment shows that SEAP expressed and secreted from transfected CHOK1 cells can indirectly mark an antibody tether on a bead complex by alteration of a peptide in solution, whereby the altered peptide binds to the tether.

(1) Direct Tether Marking

Two sets of 10 μm monobead complexes were synthesized as before except that in one set the peptide tether was phosphorylated. The tether was thus, either (Phospho)-YGGFLGGGGSK[biotin]-streptavidin (SEQ ID NO:23) or YGGFLGGGGSK[biotin]-streptavidin (SEQ ID NO:16). The concentration of the beads was 6,000 beads/μl. The phospho-YGGFL (SEQ ID NO:24) beads are referred to as ET-pY (encoded peptide trimer+pYGGFL (SEQ ID NO:24)) and YGGFL (SEQ ID NO:6) beads are to as ET-Y (encoded peptide trimer+YGGFL (SEQ ID NO:6)).

The CMV SEAP clone 3B9 (see above) was grown to 90% confluence in two wells on a 6-well cell culture plates (Limbro, Flow Laboratories); this is about $2.6 \times 10^6$ cells/well. On another 6-well plate, nontransfected CHOK1 cells (without SEAP) were also grown to 90% confluence in one well of the plate. These monolayers of cells were grown in DMEM/F12, 10% FBS (Gibco), 1% Pen/Strep Fungizone (Bio Whittaker).

The monolayers were washed with 5 ml of D-PBS 2× (Gibco BRL) and once with 2 ml of the serum free assay media DMEM/F12 SF which is DMEM/F12 (Gibco BRL), 1.0% BSA (USB Fraction V, RIA grade), 10 mM L-homoarginine (Sigma), 1% Pen/Strept (Bio Whittaker). 1 ml DMEM/F12 SF was added to each monolayer. 300,000 ET-pY beads were added to one 3B9 monolayer and the CHOK1 monolayer. ET-Y beads were added to the other 3B9 monolayer. All beads were added to the monolayers in 50 μl DMEM/F12 SF. The bead complexes were incubated on the monolayers for six hr in a 37° C. cell incubator.

This experiment was designed to compare staining of the ET-pY beads added to 3B9 SEAP cells to those added to the control CHOK1 cells. The 3B9 cells, which produce SEAP, should remove the phosphate group from the peptide tether on ET-pY complexes thereby enabling detection of the YGGFL (SEQ ID NO:6) peptide with the monoclonal antibody 3E7 (Gramsch Laboratories). Conversely, the CHOK1 cells, which do not produce SEAP, should not remove the phosphate group from the peptide tether on ET-pY complexes. With the phosphate group still present, the peptide tether is incapable of binding with 3E7 Ab. ET-Y on 3B9 cells served as a positive control to show that incubation of the peptide tether with cells and cell products does not destroy the peptide. If intact after incubation, the YGGFL (SEQ ID NO:6) peptide on these beads is detectable with 3E7 Ab. Presence of bound 3E7 on all bead complexes was detected with goat anti-mouse IgG2a R-PE. The results were viewed with a Beckton Dickinson FACScan™ machine.

The beads were pipetted off the monolayers into eppendorf tubes and the cells discarded. The beads from the three different monolayers were kept separate. The beads were washed as before and each bead population (condition) was then divided in half. One half of each population was incubated with 12.5 nM 3E7 prebound to 1.0 mg/ml protected oligo 5347 (random 50mer) for 30 min to reduce binding of 3E7 to complex oligonucleotide tags. The other half was incubated with 12.5 Nm 3E7, prebound to 1.0 mg/ml protected oligo 5347, precompeted with soluble 100 μM leucine enkephalin (YGGFL) (SEQ ID NO:6) for 30 min, (Peninsula Laboratories)). The precompeted 3E7 control is to determine the background or nonspecific binding of 3E7 to the beads. All of the above were diluted in PBSTB for a final volume of 250 μl/tube of beads. The 3E7 mixtures were incubated with beads for 2 hr at 4° C. on a shaker.

After incubation with +/− precompeted 3E7, the beads were washed in 1 ml PBSTB 2× as before. Goat anti-mouse IgG2a R-PE (Southern Biotechnology), was diluted 1:50 in PBSTB. It was filtered through a 0.2 μm filter basket (Costar Spin-X), and added to the beads at 250 μl/tube. The beads were incubated with this stain for 20 min at room temperature on a shaker. The beads were washed with 1 ml PBSTB and resuspended in 250 μl of the same.

Results were analyzed by running the beads on a FACScan™ machine. FACScan settings were as follows: Parameter 1 (Forward Scatter (FSC) detector) was set at an amplifier gain of 2.03 in the linear mode. Parameter 2 (Side Scatter (SSC)) was set at an amplifier gain of 1.0 in the log mode with a voltage setting of 180. Parameter 3 (FL1 detector) was set at an amplifier gain of 1.0 in the log mode with a voltage setting of 150. Parameter 4 (FL2 detector) was set at an amplifier gain of 1.0 in the log mode with voltage setting of 260. There was no compensation. The phycoerythrin conjugate on the goat anti-mouse IgG2a excites at 488 nm and emits at 575–585; therefore, beads bound to goat anti-mouse IgG2a can be detected with FL2 which detects light from 564 nm to 606 nm.

The control, ET-Y complex peptides gave an FL2 signal of 300, a 24-fold increase over the precompeted control showing an FL2 signal of 12.5. The 24-fold increase in signal in the FACS is referred to as a shift of 24×. The test ET-pY complex peptides were dephosphorylated (i.e., marked), by the 3B9 SEAP cell monolayer, giving an FL2 signal of 22, but not marked by the CHOK1 cell monolayer showing an FL2 signal of only 8, a shift of 2.5×. This shift indicates that SEAP cells can directly mark the modifiable tether on monobead complexes in tether marking assays.

(2) Indirect Marking

In this experiment, SEAP is used to dephosphyorylate the phosphorylated biotinylated peptide described above, which then binds to a 3E7 tether on complexes. The modified tether was then detected with streptavidin conjugated to Phycoerythrin (R-PE).

The Gal4 DNA response element (5× UAS) was cloned upstream of the SEAP reporter gene, driven by the tk promoter, into the pGL3 vector (Promega). The pSG5 vector (Stratagene) was used to clone a Gal4 DNA Binding Domain/RARa (Retinoic Acid Receptor alpha)(carboxy end) fusion. These two plasmids were simultaneously transiently lipofected into CHOK1 cells using with Lipofectamine (Gibco BRL). The lipofected cells were seeded into individual wells on 2, 96-well culture plates (Falcon). The cells were grown for 16 hr in 100 μl/well Optimem Media (Gibco) with 10% dilapidated serum (Sigma) that was heat treated at 65° C. for 45 minutes before adding to the media. Serum was heated to inactivate endogenous phosphatases. After 16 hr growth at 37° C., there were $10^4$ cells/well. Cells in one plate were stimulated with 1 μM retinoic acid; the cells in the other plate were not stimulated. Media was the same. The plates were incubated in the 37°

C. cell culture incubator for another 24 hr. The supernatants were removed from the individual wells on the plates. All supernatants from stimulated cells were pooled; all supernatants from nonstimulated cells were pooled. Both were stored at 4° C. overnight. The cells were discarded.

The next day, 100 µl of each supernatant was tested for SEAP activity using the Tropix Chemiluminescent Assay Kit, as before. The supernatant from the cells stimulated with retinoic acid produced about 0.52 units of SEAP/ml after 24 hr stimulation with retinoic acid. The supernatant from the cells without stimulation with retinoic acid produced only 0.004 units of SEAP/ml after 24 hours. This is a 126-fold increase in SEAP production upon stimulation of the RARalpha with 1 µM retinoic acid.

A 10 µm bead complex was synthesized as before except that the tether was the 3E7 antibody. The antibody tether was added to beads after synthesis of peptides and nucleic acid tags. 3E7 was passively absorbed to the beads @ 0.1 mg/ml in PBS 0.01% azide for two hr at room temperature on a shaker. These beads are called ET-3E7 (encoded peptide trimer+3E7 antibody). The beads were washed twice in 1 ml PBSTB [PBS, 0.05% Tween20 (Sigma), 0.1% BSA (USB, Fraction V, RIA grade) 0.01% azide] by centrifuging at 14 krpm for 1 min, removing the supernatant from the bead pellet and resuspending the pellet. The beads were then blocked 1 ml PBS 0.05% Tween 20, 1.0% BSA, 0.01% azide overnight at 4° C. on a shaker. The beads were washed as before, resuspended in 200 µl PBSTB and stored at 4° C. The concentration of beads was 6,000/µl.

100 µl of cell supernatant, from aliquots of cells which had or had not been stimulated with retinoic acid, was added to 1.5 ml eppendorf tubes. 100 nM (1 µl of stock) soluble biotinylated peptide (AF12402), (phospho)-YGGFLGGGGSK[biotin] (SEQ ID NO:7) referred to as pY, was added to each supernatant. Lastly, 50,000 ET-3E7 beads (8.3 µl bead stock) were added to each supernatant. The two tubes were vortexed and incubated at 37° C. on a shaker for 2 hr.

The beads were centrifuged and the supernatant discarded. The beads were washed as before. The beads were then stained with 250 µl of Streptavidin R-PE (Phycoerythrin conjugate) (Sigma) @1:50 in PBSTB. The stain was filtered through a 0.2 µm filter basket (Costar Spin-X). Beads and stain were incubated together for 20 min at room temperature on a shaker. The beads were washed once as before, and resuspended in 250 µl of PBSTB.

The results were analyzed by running the beads on a FACScan™ machine, as before. The ET-3E7 complexes incubated with soluble peptide pY and supernatants from stimulated cells showed tether marking with an FL2 signal of 100. The ET-3E7 complexes incubated with soluble peptide pY and supernatants from nonstimulated cells showed little tether marking with an FL2 signal of 20. These results show that cells can indirectly mark the modifiable tether on bead complexes in tether marking assays.

b. Agonist Stimulated Marking by Secreted Acid Phosphatase

A plastic 96-well immunoassay plate (Beckman #373660) was coated with 0.41 µM streptavidin for 1 hour at 37° C. After washing, it was blocked with 1×PBS, 1% bovine serum albumin (BSA) for 1 hr at 37° C. After washing, 100 nM of AF12402 ((H)-(Phospho-Y)GGFLGGGGSK(biotin)(OH)) (SEQ ID NO:7) in 1×PBS, 0.1% BSA was incubated on the plate overnight at 4° C. The wells were washed with 1×PBS and a yeast culture containing ARY84 at a density of $OD_{600}$=0.1 in defined medium was added to the plate. The following conditions were tested: +growth selection, no α-factor; +growth selection, +500 nM α-factor.

After addition of yeast the culture was either removed immediately (t=0; wells were filled with 1×PBS/ 0.1% BSA) or after 24 hr incubation at 30° C. At the end of the incubation, the wells were washed and developed using a standard protocol with 1 nM 3E7 antibody for the primary development (4° C., 1 hr) and 1/1000 diluted alkaline phosphatase conjugated goat anti-mouse antibody (Gibco) at 4° C. for 1 hr. Binding of antibodies was quantitated using a standard colorimetric alkaline-phosphatase reaction (see Cull et al., PNAS 89, 1865–1869 (1992)).

TABLE 4

Well-marking activity by ARY84 grown under selective conditions. Activity is in $OD_{405}$ units/minute.
ELISA showing agonist-induced well marking by ARY84

|  | No alpha-factor | 500 nM alpha factor |
|---|---|---|
| T = 0 | 0.11 | 0.113 |
| T = 24 Hrs | 0.214 | 0.8 |

At t=0 the wells show an $OD_{600}$ =0.11 irrespective of whether α-factor was present. After 24 hr growth of yeast in the wells, there is a 4-fold increase in $OD_{405}$ in the wells containing α-factor compared to wells lacking a-factor ($OD_{405}$ =0.21 in the wells lacking α-factor, and 0.8 in the wells containing α-factor).

These results demonstrate agonist-induced dephosphorylation of pYGGFL (SEQ ID NO:24) leading to marking of ELISA wells which have the tether attached to the surface of the plate.

c. Tether Modification by Yeast Acid Phosphatase

This system employs yeast ARI 84 reporter cells bearing an STE2 receptor and containing a reporter construct in which a pho3 gene is linked to a FUS1 promoter. Acid phosphatase expressed by the yeast is used to dephosphorylate the substrate phospho-YGGFL-linker-biotin. (SEQ ID NO:25) As a result of dephosphorylation, the substrate can bind to a 3E7 antibody tether. The biotinylated portion of modified tethers is stained using a PE- or alkaline-phosphatase-conjugated streptavidin. Complexes with stained tethers are sorted by FACS™.

ARY84 culture from a fresh, 4–10 day old patch was grown in 3 ml SC minimal media minus Trp, Ura, Leu, pH adjusted to 6.15 using MES buffer 200 mM final at @30C overnight in a tube rotator. At A600, the growing culture was diluted to 0.1 A600 in duplicate in pH 6.15 SC media minus Trp, Ura, Leu. One diluted culture was induced by addition of alpha factor to 500 nM final concentration. 0.1 ml of the appropriate diluted induced or uninduced culture was added to wells of a BSA-blocked 96-well microtitre plate. Wells were blocked by treatment with 0.2 ml of PBS/1% BSA, overnight at 4° C. shaking in triplicate.

A desired amount of monobeads (at about $1 \times 10^7$ beads/ml) was washed once in 0.5 ml methanol, and twice in 1 ml PBS, pH 7.5. The beads were coated with antibody 3E7 using 0.5 ml 0.1 mg/ml 3E7 Ab solution for 2 hr at room temperature on a shaker. The beads were washed twice using PBS/1% BSA, and then blocked in 1 ml PBS/1% BSA overnight at 4° C. with shaking. The beads were washed twice in PBS/1% BSA then resuspended in 0.5 ml PBS/0.1% BSA/0.01% sodium azide. The density of beads was determined and about $1 \times 10^5$ beads were added to each well (after washing with PBS 0.1% BSA to remove the azide).

AF12402 ((H)-(Phospho-Y)GGFLGGGGSK(biotin)(OH)) (SEQ ID NO:7) substrate was added to each well to a final concentration of 200 nM. This was done in a small volume to prevent dilution of the cell growth media. 20 µl 1.2 μM stock in 200 mM Tris pH 7.4 was added to each well. AF12861 YGGFLGGGGSK(biotin)(OH)) (SEQ ID NO:15) was added in separate wells at 200 nM as a positive control.

After addition of beads and substrate to the wells, the plate was placed open in a humidified chamber in a 30° C. incubator and allowed to grow and induce for 18–24 hr. After 18–24 hr, cells and beads were removed from wells and placed into a 1.5 ml eppendorf tube, washed twice in pH 7.5 PBS/0.1% BSA, and resuspended in 300 μl of the same containing a 1:50 dilution of Streptavidin-PE conjugate stain. The stain was incubated at room temp for 2 hr with gentle shaking. The beads and yeast were washed four times in pH 7.5 PBS/0.1% BSA, and resuspended in 350 μl PBS pH 7.5.

Staining was analyzed by running the beads through a Becton Dickinson FACScan™ machine. A 10-fold shift was observed between beads exposed for 18 hr to ARY 84b induced with alpha factor compared to yeast cells that were not induced with alpha factor.

This procedure is adapted for screening a compound library for agonists of the yeast STE2 receptor in a nanowell grid as follows. Pre-synthesized encoded compound library beads are washed twice in 1 ml PBS, pH 7.5 and then blocked in 1 ml PBS/1% BSA at room temperature for 2 hr or overnight at 4° C. shaking. Beads are then washed twice in PBS/1% BSA/azide, and resuspended in pH 7.5 PBS/ 0.1% BSA/ 0.02% azide. The beads are coated with antibody 3E7 using 0.5 ml 0.1 mg/ml 3E7 Ab solution for 2 hr at room temperature on a shaker.

ARY84 is propagated from a fresh, 3–4 day old patch in 3 ml SC minimal media minus Trp., Ura., Leu., Ph adjusted to 6.15 using MES buffer 200 Mm final, and incubated at 30° C. overnight in a tube rotator. At A600, the growing culture is diluted to 0.2 A600 in duplicate in Ph 6.15 SC media minus Trp, Ura, Leu. 200 Nm AF12402 (Phospho-YGGFL-biotin) (SEQ ID NO:26) is added followed by library beads.

The mixture is added to a nano-well array, blocked using PBS/1% BSA, overnight at 4° C. About 1 ml of culture is used per array including about 300,000 beads per 7 cm$^2$ array. Yeast and beads were allowed to settle into nano-wells for 30–60 min.

After adding cells and beads to the nano-well array, photolysis is carried out to release compounds from the beads. Photolysis is carried out using a 30 minute exposure of 360 nm light at 8 mW/square cm intensity.

After photolysis, the plate is placed open (or covered with dialysis membrane) in a humidified chamber in a 30° C. incubator and allowed to grow and induce for 18–24 hr. After 18–24 hr, beads and yeast cells are removed from nano-wells and placed into a 1.5 ml eppendorf tube, washed twice in Ph 7.5 PBS/0.1% BSA, then resuspended in 300 μl of the same containing a 1:50 dilution of streptavidin-PE conjugate stain. The stain is incubated at room temp for 2 hr with mild shaking.

The beads and yeast are washed four times in pH 7.5 PBS/0.1% BSA, resuspended in 350 μl PBS pH 7.5. Results are analyzed by running the beads through a Becton Dickinson FACScan machine.

d. Marking of tether with BirA

Figure 9:
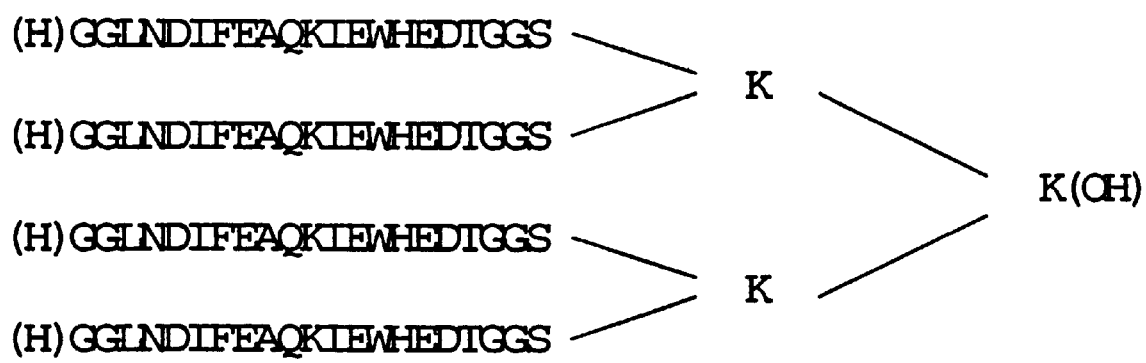
FIG. 9: A tetrameric, antigenic soluble peptide (containing SEQ ID NO:3) substrate for BirA.

The BirA enzyme, which is normally nonsecreted, catalyzes the addition of biotin onto a specific peptide sequence (Schatz, Bio/Technology 11, 1138–1143 (1993). The BirA peptide sequence was synthesized as a soluble, multiple antigenic, tetrameric peptide (FIG. 9). The sequence of each peptide is N-GGLNDIFEAQKIEWHEDTGGS-C (SEQ ID NO:3). The soluble peptide molecular weight was 9544.26. It was dissolved in 100% DMSO to 1 mM and diluted to 100 μM, 10 μM, and 1 μM in PBS 0.05% azide. The soluble tetrameric peptide was passively absorbed to 200,000 plain monobeads (no DNA tags, no compounds) at each of the above stated concentrations in 1.5 ml eppendorf tubes, at a final volume of 500 μl/tube, for 1 hr at room temperature on a shaker. The beads were washed twice in 1 ml PBSTB (PBS 0.05% Tween20 (Sigma), 0.1% BSA (USB, fraction V, RIA grade, 0.01% azide) by centrifuging at 14 krpm for 1 min, removing the supernatant from the bead pellets and resuspending the pellets. The beads were blocked in 1 ml PBS 0.05% Tween20, 1.0% BSA, 0.1% azide, for 1 hr at room temperature on a shaker. The beads were washed as before, resuspended in 200 μl PBSTB and stored at 4° C.

The next day, two tubes of beads were centrifuged at 14 krpm for 1 min, and the buffer removed from the bead pellets. 400 μl of BirA buffer containing the purified BirA enzyme was added to the beads, tubes were vortexed and incubated for 1 hr at room temperature on a shaker.

The BirA buffer was made up of 20 mM Tris pH 7.4 (Sigma), 100 μg/ml acetylated BSA (New England Biolabs), 10 μM biotin, 5 mM MgCl$_2$ (Sigma) plus 10 μl/ml 100 mM ATP (Pharmacia Biotech), 0.5% NP40 (Sigma) and 0.75 μg (1 μl) purified BirA enzyme (per 500 μl buffer). BirA is ATP-dependent, so ATP was added. Biotin was added so the enzyme biotinylates the peptide substrate on the beads.

After incubation with BirA enzyme, the beads were washed as before. Streptavidin conjugated to R-PE (Phycoerythrin) (Sigma) @ 1:20 in PBSTB was added to the beads in a final volume of 250 μl/tube. Incubation with this R-PE stain was for 20 min at room temperature on a shaker. The beads were washed twice and resuspended in 400 μl PBSTB.

Biotinylation of the peptides absorbed to the beads was detected by binding streptavidin R-PE to the biotin on marked peptides. Results were analyzed by running the beads on a Beckton-Dickinson FACScan machine as before.

The absorbed tetrameric peptide was marked well, even at a 1 μM coating giving an FL2 signal of 950. Background signal from BirA peptide substrate beads incubated with no BirA enzyme showed an FL2 signal of 15 for a shift, (+/– BirA enzyme) of 63×.

The next experiment shows similar marking of beads with cell-produced BirA. The BirA substrate peptide N-GGLNDIFBAQKIEWHEDTGGS-C (SEQ ID NO:3) was synthesized onto monobeads. The beads did not have DNA tags or compounds. The beads were blocked in 1 ml PBS 0.05% Tween20 (Sigma) 1.0% BSA (USB Fraction V, RIA grade), 0.01% azide for 1 hr at room temperature on a shaker.

The beads were washed twice in 1 ml PBSTB (PBS 0.05% Tween20 0.1% BSA 0.01% azide) by centrifuging at 14 krpm for 1 min, removing the supernatant from the bead pellet and resuspending the pellet. The beads were brought up in 200 μl PBSTB, counted in a hemocytometer and stored at 4° C.

The BirA gene was cloned into the alpha+KH vector and stably transfected into adherent CHOK1 cells. The alpha+KH vector without the BirA gene was also stably transfected into adherent CHOK1 cells to serve as a negative control. Cells were grown and expanded in T162 flasks (Falcon). At 80% confluence, both cell lines were harvested with Veresene 1:5000 (Gibco) and resuspended in 10 ml D-PBS (Gibco). The cells were centrifuged for 5 min at 800 rpm, washed with 10 ml D-PBS, counted in the hemocytometer and centrifuged again. The cells were resuspended in BirA buffer (20 mM Tris pH 7.4 (Sigma), 100 μg/ml acetylated BSA (New England Biolabs)), 10 μM biotin, 5 mM MgCl$_2$ (Sigma) plus 10 µl/ml 100 mM ATP (Pharmacia Biotech), 0.5% NP40 (Sigma)] at a concentration of 1×10^7 cells per 400 µl. Aliquots of 400 µl of each cell line were placed into 1.5 ml eppendorf tubes. The cells were lysed by freeze-thaw by alternating the tubes between a dry ice/ethanol bath and a 37° C. heat block. The tubes were alternated between these conditions three times, leaving the tubes in both conditions about 2 minutes each time. The lysis was to release the BirA gene from the cells since it is normally a non-secreted protein. The lysed cells were centrifuged at 14 krpm for 5 min to pellet the cell debris. The lysates (from 1×10^7 cells) of each cell line were transferred to new 1.5 ml eppendorf tubes. 40,000 of the BirA peptide substrate beads were added to both tubes of lysates. The lysates and beads were incubated together for 1 hr at 37° C. on a shaker.

The beads were pelleted by centrifuging at 14 krpm for 1 min. The lysate supernatants were discarded and the beads washed 3× in PBS 1% BSA, 0.01% azide by resuspending the beads, centrifuging as above and removing the wash supernatants. The beads were stained with streptavidin R-PE (Phycoerythrin) (Sigma) @ 1:20 in PBS 0.1% BSA 0.01% azide in a final volume of 250 µl/tube. Incubation was for 20 min at room temperature on a shaker. The beads were washed twice as before, and resuspended in 250 µl PBS 0.1% BSA, 0.01% azide.

Results were analyzed by running the beads on a Beckton-Dickinson FACScan™ machine, as before. The data showed that peptide substrated beads incubated with lysates containing the BirA enzyme were biotinylated and detectable with the streptavidin R-PE. The FL2 signal from these beads was 236. The peptide substrate beads incubated with lysates not containing the BirA enzyme did not get marked and were detectable with streptavidin R-PE at only a background level. The FL2 signal from these beads was 25. This is a ten-fold difference in signal +/− BirA enzyme production.

e. Tether Marking by Tpa/Plasminogen Reporter System

This procedure illustrates the use of signal amplification in tether marking. Tissue plasminogen activator (tPA) produced by CHO cells catalytically converts plasminogen into plasmin, which in turn cleaves the peptide on the bead at the R—Y bond. The exposed YGGFL (SEQ ID NO:6) N-terminus is then available to bind to the 3E7 antibody (i.e. the tether has been marked). A 1/1000 diluted culture supernatant gives an easily detectable shift.

Washed beads were coated with 1 ml of 1 mg/ml Streptavidin; RT, 1 hour on shaker. The beads were washed with PBS 2×. The beads were blocked with 1.5 ml of PBT for 1 hr on a shaker at room temperature. The beads were washed twice with PBS. 1 ml 10 µM Ac-GIYRYGGFLGGGGSK (biotin)(OH) (SEQ ID NO:27) (AFFY3-20-MBH, SynPrep) in PBT was added and the mixture was incubated at room temperature for 1 hr on shaker. The beads were washed twice with PBS. The beads were resuspended in 1.5 ml PBT and split into 13 microcentrifuge tubes. 25 µl of 0.25 U/ml Human Plasminogen (Sigma) was added to tubes #1 to 12 and then 1 ml of CHO/tPA (ATCC CRL-9606) culture supernatant with or without 10% FCS (Fetal Calf Serum) at 1:10, 1:10^2, 1:10^3, 1:10^4, 1:10^5 dilution was added to tube #1 to 10 respectively. 1 ml of CHO-K1 cell culture supernatant was added to tube #11 (negative control of CHO Cell supernatant); 1 ml of 25 U/ml tPA was added to tube #12 (positive control), and 1 ml of PBT (negative control of the reagents) was added to tube #13. The tubes were incubated at room temperature for 1 hour on shaker. The beads were washed twice with PBS. 0.5 ml/tube of 1 ug/ml 3E7 was added and the tubes were incubated at room temperature for 30 min on shaker. The beads were washed twice with PBS. 0.25 ml/tube of 1:50 goat anti-Mouse IgG2a-PE (Fisher Hamilton) in PBT was added and the tubes were incubated for 30 min on shaker. The beads were washed three times with PBST. The beads were resuspended in 300 µl PBT. Staining was analyzed on a FACScan (488/575, excitation/emission), as above.

It was found that beads treated with 1:10^4 to 1:10 diluted CHO/tPA supernatant with 10% FCS yielded a shift of 1.25× to 15× respectively compared with PBT negative control beads (see Table 5). There was almost no tPA activity from the negative control CHO-K1 cell supernatant. tPA activity from serum-free culture was about 10 times less compared with tPA activity from 10% FCS culture supernatant.

TABLE 5

| Dilution | Shift |
| --- | --- |
| 1:10 | 15 |
| 1:100 | 13 |
| 1:1000 | 4.2 |
|  | 1.25 |
|  | 1.05 |

6. Competition Assay a. Receptor Immobilized to Well

This procedure illustrates a competition assay that can be used to identify compounds that bind to the IL-1 receptor. In this experiment, an IL-1 type I receptor is fused to a human IgG1 Fc region (thus making a bivalent receptor). The bivalent receptor was immobilized to microtiter plate surface using a peptide (AF12413—see below for sequence) fused to MBP (maltose binding protein). Peptides from this family have previously been shown to bind in the ligand-binding pocket of the receptor (see Yanofsky et al., Proc. Natl. Acad. Sci. USA, 93, 7381–7386 (1996)). In a library screening for compounds that compete with the peptide for binding to the ligand binding pocket, the released AP activity modifies the tether of library complexes having active competitors.

A 96-well plate (Immulon 4, Dynatech) was coated with 100 µl/well 10 µg/ml MBP-AF12413 (MBP-G4S-DNTAWYERFLLQYN) SEQ ID NO:28 in PBS and incubated at 37° C. for 1 hour. The wells were washed three times with PBS. The wells were blocked with 300 µl/well PBT at 37° C. for 1 hr and wash twice with PBS. 100 µl/well of 1:100 IL-1RFc (OD280 of the sock is 0.24, baculovirus expressed, purified by protein A column) in PBT was added and incubated at room temperature for 1 hr on a shaker. The wells were washed twice with cold PBST. 100 µl of 1:500 goat anti-human IgGFc-AP (Sigma) in PBT was added, and incubated at room temperature for 90 min on a shaker. The wells were washed three times with warm (37° C) PBST. 100 µl/well 100, 10, 1, 0.1, 0.01 µM AF12304 (NH2-YEWTPGYYQJY-NH2) SEQ ID NO:29 (IC50 in IL-1R binding assay is about 2 nM) in PBT, and PBT only, were added to different wells in duplicate and incubated at room temperature for 45 min on shaker. 40 µl/well was transferred to wells containing 180 µl/well of alkaline phosphatase substrate (1 mg/ml of PNPP in Diethanolamine Buffer). The plate was read at A405 on kinetic mode for 3 hours (Table 6).

| Results | |
| --- | --- |
| Competitor Concentration (µM) | Amount of AP Activity Released Compared to No Competition |
| 0 | 1 |
| 0.01 | 1.2 |
| 0.1 | 4.2 |

-continued

Results

| Competitor Concentration (µM) | Amount of AP Activity Released Compared to No Competition |
|---|---|
| 1 | 23 |
| 10 | 29 |
| 100 | 28 |

The results show that released AP-labelled receptor increases as the concentration of competing peptide is increase.

b. Receptor Immobilized to Reservoir Bead

This example uses two classes of beads referred to as reservoir beads and library beads. The reservoir beads have receptor immobilized via a known ligand. The library beads have compounds to be screened, identifier tags and tethers as before. A compound released from a library bead competes a labelled receptor from a reservoir bead, and the labelled receptor, directly or indirectly, modifies a tether on proximate library beads. Both sets of beads can be added to nanowells for performing the assay.

500 µl beads (Polysciences, Inc., 2.5% Solids-latex, 2 µm) were washed twice with PBS, resuspended in 1 ml of PBS and split into 5 tubes (a, b, c, d, e). 300 µl 1 mg/ml coating protein was added per tube and incubated at 37° C. for 3 hr on shaker. The beads were washed with PBT. Coating proteins were added in the five tubes as follows: a. BSA-Biotin (Sigma), b. BSA (LC)-Biotin (Sigma), c. Hemocyanin-Biotin (Sigma), d. Streptavidin (Gibco BRL), e. Biotin-MBP-AF12413 [MAGGLNDIFEAQK(biotin)LEWHEDTGGS (SEQ ID NO:30)-maltose binding protein-DNTAWYERFLQYN (SEQ ID NO:31)].

The beads were blocked with 1 ml PBT and incubated at room temperature overnight on shaker and washed with PBT. 300 µl of 1 mg/ml streptavidin and 1.2 ml PBT were added to a, b, c, tubes, which were incubated at; 37° C. for 1 hour on shaker. The tubes were washed twice in PBS. 164 µl 0.347 mg/ml biotin-MBP-AF12413 and 1 ml of PBT were added to tubes a, b, c, d tubes, which were incubated at 37° C. for 1 hr on a shaker. The tubes were washed twice with PBS. 570 µl of 1:10 diluted IL-1RFc was added to each tubes (a to e) and the tubes were incubated at 37° C. for 1 hour on shaker, and washed twice with PBS. 570 µl 1:50 diluted goat anti-human IgGFc-AP was added to each tube and incubated at 37° C. for 1 hour on a shaker. The tubes were washed three times with warm (37° C.) PBST. The beads were resuspended with 1 ml PBT each tube and split into 5 tubes giving a total of 25 tubes. 570 µl 100, 10, 1, 0.1 µM AF12304 or PBT only, was added to the different tubes, which were incubated at 37° C. for 1 hour on shaker.

The tubes were spun at 14,000 rpm for 2 min. 2×50 µl supernatant from each tube was added to new wells of a 96-well plate. 200 µl of AP substrate buffer was added to each well. The Vmax of A405 of the wells are shown in Table 7.

TABLE 7

Amount of AP activity released compared to no competition

| Competitor concentration | BSA-Biotin | BSA (LC)-Biotin | Hemocyanin-Biotin | Streptavidin | Biotin-MBP-AF12413 |
|---|---|---|---|---|---|
| 100 | 3.4 | 5.7 | 5.2 | <1 | <1 |
| 10 | 2.7 | 4.4 | 4.2 | <1 | <1 |
| 1 | 3.1 | 5.4 | 4.2 | <1 | <1 |
| 0.1 | 1.1 | 1.5 | 1.6 | <1 | <1 |
| 0 | 1 | 1 | 1 | 1 | 1 |

The experiment shows that the beads coated with streptavidin or biotin-MBP-AF12413 produced only background signals, and the beads coated with protein-Biotin showed, at 1 µM AF12304 competition, a 3.1 to 5.4 increased AP activity released compared to beads without competition. Thus, a reporter immobilized to reservoir beads can be released by competitive binding thereby allowing it to modify the tethers of proximate beads bearing compounds to be screened.

7. Recovering Marked Beads by Gold Sorting

This example uses gold sorting to separate beads with a modified tether from those with an unmodified tether (or a less heavily modified tether). Gold sorting is particularly useful to perform separations with large numbers of beads (generally greater than $10^6$).

Monobeads were washed with 50% methanol in PBS 1×, then PBS 2×. The beads were coated with 1 ml of 1 mg/ml streptavidin in PBS and incubated at RT for 1 hour on shaker. The beads were washed with PBS 2×. The beads were blocked with 1 ml PBT (PBS+1% BSA+0.05% Tween-20) and incubated at room temperature for 1 hour on shaker. The beads were washed with PBS 2×. 1 ml of 10 µM AF12861 [(H)-YGGFLGGGGSK(biotin)(OH)] (SEQ ID NO:15) in PBT was added and incubated at room temperature for 1 hour. The beads were washed 2× with PBS. 3E7 was preincubated at 12.5 nM, with 1, 10, 100, 1,000 µM of YGGFL (SEQ ID NO:6) for about 45 min at room temperature on a shaker. The beads were split into 5 microcentrifuge tubes and 400 µl of 3E7 with 1, 10, 100, 1,000 µM YGGFL (SEQ ID NO:6) or without YGGFL (SEQ ID NO:6) inhibition, was added to different tubes. The tubes were incubated at room temperature on a shaker for 50 min and washed twice with PBS.

500 µl/tube of rabbit anti-mouse IgG (Tago Immunologicals), 1:1000 diluted with PBT was added and the tubes were incubated at room temperature for 40 min on a shaker, and washed twice with PBS. Goat anti-rabbit IgG-gold conjugate (Bio-rad) was passed through a 0.22 µm filter (Costar Spin-X) to remove aggregates. 250 µl gold conjugate was added to each tube and the tubes were incubated at room temperature on a shaker for 30 min, then left in a cold room, on shaker, overnight. The beads were washed on a 0.22 µm filter 2× with PBS (to remove unbound gold conjugate).

250 µl/tube 1:20 diluted goat anti-rabbit IgG-PE was added and incubated at room temperature for 30 min on shaker. The tubes were washed 2× with PBS. The beads were resuspended with 44% (Brix %, measured by digital refractometer, ATAGO) sucrose in PBS and the beads were mixed into one tube. The tube was spun at maximum speed and the pellet was collected (#1), and the Brix % of supernatant was measured. A small volume at a time of 22% sucrose in PBS was added to the supernatant, which was spun, and the pellet(#2) was collected, and the Brix % of the supernatant was determined. The previous step was repeated 11 several times until there were no more beads that precipitate from the supernatant. Each pellet was resuspended with 300 µl of PBT and analyzed on FACScan.

This experiment shows that gold sorting is a good tool to separate beads with modified tethers beads with unmodified tethers. Further, beads with different degrees of modification can be isolated by changing the concentration of the sucrose. In this case, the strong positive beads, 3E7 stained beads without YGGFL (SEQ ID NO:6) or with 1, 10 µM YGGFL (SEQ ID NO:6) competition, all precipitate at 44% sucrose. The weak positive beads, beads with 100 µM YGGFL (SEQ ID NO:6) competition, precipitate at 38.2% sucrose, and the negative beads, with 1 mM YGGFL (SEQ ID NO:6) competition and plain beads, precipitate at 36.1% sucrose. FACScan analysis of these beads indicates that this technique can separate positive beads from negative beads with as little as 3× shift.

From the foregoing, it should be apparent that many of the described methods have several general features which can be expressed concisely as follows. The methods entail the use of a complex comprising a compound under test, and a tether susceptible to modification to screen the compound for a desired activity, whereby the desired activity can be determined from the presence or absence of modification of the tether. In many uses, the complexes further comprise a tag recording at least one step in synthesis of the compound borne by the complex. After modification of tags, at least one step in the synthesis of a compound having the desired activity can be determined by decoding the tag. Although the foregoing invention has been described in detail for purposes of clarity of understanding, it will be obvious that certain modifications may be practiced within the scope of the appended claims. All publications and patent documents cited above are hereby incorporated by reference in their entirety for all purposes to the same extent as if each were so individually denoted.

What is claimed is:

1. A method of screening compounds for capacity to transduce a signal through a cellular receptor, comprising providing a plurality of supports, each support bearing multiple copies of a compound under test, and a tether susceptible to modification by a reporter molecule;

contacting the supports with cells having a receptor and a DNA fragment encoding the reporter molecule;

freeing a portion of the multiple copies of each of the compounds under test from the supports, whereby at least one compound transduces a signal through the receptor of a cell causing expression of the reporter molecule, which reporter molecule is released from the cell and modifies the tether of the support from which a portion of the multiple copies of the compound transducing the signal was freed; and isolating the support having the modified tether, which support bears the compound transducing the signal.

2. method of screening compounds for capacity to transduce a signal through a cellular receptor, comprising providing an array of compounds on a membrane, contacting the membrane with cells having a receptor and a DNA segment encoding a reporter molecule; whereby at least one compound transduces a signal through the receptor of a cell causing expression of the reporter molecule, which reporter molecule is released from the cell and modifies the membrane at a position proximate to the compound transducing the signal, whereby said modification of the membrane allows identification and isolation of the compound transducing the signal.

3. The method of claim 2, wherein the array of compounds is provided by:

providing an array of cells, each producing a compound under test;

contacting the cells with a membrane, whereby compounds are transferred from the cells to form the array of compounds attached to the membrane, the compounds occupying the same relative positions as the respective cells producing the compounds; and the compound transducing the signal is isolated by:
identifying the cell in the array of cells aligning with the modified position of the membrane, this cell producing the compound transducing the signal.

4. A method of screening compounds for capacity to transduce a signal through a cellular receptor, comprising providing a collection of cells, each secreting a compound under test and each bearing a tether on its surface;

contacting the collection of cells with reporter cells having a receptor and a DNA segment encoding a reporter molecule; whereby at least one compound transduces a signal through the receptor of a reporter cell causing expression of the reporter molecule, which reporter molecule is released from the reporter cell and modifies the tether of the cell from the collection of cells secreting the compound that transduce the signal;

isolating the cell having the modified tether, wherein the compound transducing the signal is isolated by culturing the cell.

* * * * *

```
                            SEQUENCE LISTING (1) GENERAL INFORMATION:

(iii) NUMBER OF SEQUENCES: 31

(2) INFORMATION FOR SEQ ID NO: 1:

(i) SEQUENCE CHARACTERISTICS:
             (A) LENGTH: 5 amino acids
             (B) TYPE: amino acid
             (C) STRANDEDNESS: <Unknown>
             (D) TOPOLOGY: linear (ii) MOLECULE TYPE: peptide (ix) FEATURE:
             (A) NAME/KEY: Modified-site
             (B) LOCATION: 1
             (D) OTHER INFORMATION: /product= "OTHER"
                  /note= "Xaa = Tyr linked to marked
                  tether bearing bead"

(xi) SEQUENCE DESCRIPTION: SEQ ID NO: 1:

Xaa Gly Gly Phe Leu
    1               5

(2) INFORMATION FOR SEQ ID NO: 2:

(i) SEQUENCE CHARACTERISTICS:
             (A) LENGTH: 6 amino acids
             (B) TYPE: amino acid
             (C) STRANDEDNESS: <Unknown>
             (D) TOPOLOGY: linear (ii) MOLECULE TYPE: peptide (xi) SEQUENCE DESCRIPTION: SEQ ID NO: 2:

His His His His His His
    1               5

(2) INFORMATION FOR SEQ ID NO: 3:

(i) SEQUENCE CHARACTERISTICS:
             (A) LENGTH: 21 amino acids
             (B) TYPE: amino acid
             (C) STRANDEDNESS: <Unknown>
             (D) TOPOLOGY: linear
```

```
        (ii) MOLECULE TYPE: peptide (xi) SEQUENCE DESCRIPTION: SEQ ID NO: 3:

Gly Gly Leu Asn Asp Ile Phe Glu Ala Gln Lys Ile Glu Trp His Gl
1               5                   10                  15

Asp Thr Gly Gly Ser
            20

(2) INFORMATION FOR SEQ ID NO: 4:

(i) SEQUENCE CHARACTERISTICS:
            (A) LENGTH: 5 amino acids
            (B) TYPE: amino acid
            (C) STRANDEDNESS: <Unknown>
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /product= "OTHER"
                /note= "Xaa = Tyr linked to
                beta-D-galactose"

(ix) FEATURE:
            (A) NAME/KEY: Modified-site
            (B) LOCATION: 5
            (D) OTHER INFORMATION: /product= "OTHER"
                /note= "Xaa = Leu linked to
                linker-biotin"

(xi) SEQUENCE DESCRIPTION: SEQ ID NO: 4:

Xaa Gly Gly Phe Xaa
1               5

(2) INFORMATION FOR SEQ ID NO: 5:

(i) SEQUENCE CHARACTERISTICS:
            (A) LENGTH: 5 amino acids
            (B) TYPE: amino acid
            (C) STRANDEDNESS: <Unknown>
            (D) TOPOLOGY: linear (ii) MOLECULE TYPE: peptide (ix) FEATURE:
            (A) NAME/KEY: Modified-site
            (B) LOCATION: 5
            (D) OTHER INFORMATION: /product= "OTHER"
                /note= "Xaa = Leu linked to
                linker-biotin"

(xi) SEQUENCE DESCRIPTION: SEQ ID NO: 5:

Tyr Gly Gly Phe Xaa
1               5

(2) INFORMATION FOR SEQ ID NO: 6:

(i) SEQUENCE CHARACTERISTICS:
            (A) LENGTH: 5 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 6:

Tyr Gly Gly Phe Leu
1               5
```

```
(2) INFORMATION FOR SEQ ID NO: 7:

(i) SEQUENCE CHARACTERISTICS:
        (A) LENGTH: 11 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /note= "Xaa = phosphotyrosine"

(ix) FEATURE:
        (A) NAME/KEY: Modified-site
        (B) LOCATION: 11
        (D) OTHER INFORMATION: /product= "OTHER"
            /note= "Xaa = Lys linked to biotin"

(xi) SEQUENCE DESCRIPTION: SEQ ID NO: 7:

Xaa Gly Gly Phe Leu Gly Gly Gly Gly Ser Xaa
1               5                   10

(2) INFORMATION FOR SEQ ID NO: 8:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /note= "Xaa = Tyr linked to galactose"

(ix) FEATURE:
        (A) NAME/KEY: Modified-site
        (B) LOCATION: 10
        (D) OTHER INFORMATION: /product= "OTHER"
            /note= "Xaa = Lys linked to biotin"

(xi) SEQUENCE DESCRIPTION: SEQ ID NO: 8:

Xaa Gly Gly Phe Leu Gly Gly Gly Ser Xaa
1               5                   10

(2) INFORMATION FOR SEQ ID NO: 9:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Peptide
        (B) LOCATION: 1..5
        (D) OTHER INFORMATION: /note= "Xaa at positions 1-5 allow
            efficient cleavage by plasmin"

(xi) SEQUENCE DESCRIPTION: SEQ ID NO: 9:

Xaa Xaa Xaa Xaa Xaa Tyr Gly Gly Phe Leu
1               5                   10
```

(2) INFORMATION FOR SEQ ID NO: 10:

(i) SEQUENCE CHARACTERISTICS:
        (A) LENGTH: 5 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Peptide
        (B) LOCATION: 1..5
        (D) OTHER INFORMATION: /note= "Xaa at positions 1-5 allow
           efficient cleavage by plasmin"

(xi) SEQUENCE DESCRIPTION: SEQ ID NO: 10:

Xaa Xaa Xaa Xaa Xaa
1               5

(2) INFORMATION FOR SEQ ID NO: 11:

(i) SEQUENCE CHARACTERISTICS:
        (A) LENGTH: 4 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
           /note= "Xaa = acetyl-glycine"

(xi) SEQUENCE DESCRIPTION: SEQ ID NO: 11:

Xaa Ile Tyr Arg
1

(2) INFORMATION FOR SEQ ID NO: 12:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 12:

Gly Leu Asn Asp Ile Phe Glu Ala Gln Lys Ile Glu Trp His
1               5                   10

(2) INFORMATION FOR SEQ ID NO: 13:

(i) SEQUENCE CHARACTERISTICS:
        (A) LENGTH: 47 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 13:

Cys Leu Glu Pro Tyr Thr Ala Cys Asp Leu Ala Pro Pro Ala Gly Th
1               5                   10                  15

Thr Asp Ala Ala His Pro Gly Arg Ser Val Val Pro Ala Leu Leu Pr
            20                  25                  30

Leu Leu Ala Gly Thr Leu Leu Leu Leu Glu Thr Ala Thr Ala Pro
         35                  40                  45

(2) INFORMATION FOR SEQ ID NO: 14:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 14:

CTCCCGGCCA ATTGTTTCAC AGCGTTATGC TCCGCACC                          38

(2) INFORMATION FOR SEQ ID NO: 15:

(i) SEQUENCE CHARACTERISTICS:
        (A) LENGTH: 11 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 11
        (D) OTHER INFORMATION: /product= "OTHER"
            /note= "Xaa = Lys linked to biotin"

(xi) SEQUENCE DESCRIPTION: SEQ ID NO: 15:

Tyr Gly Gly Phe Leu Gly Gly Gly Gly Ser Xaa
1               5                   10

(2) INFORMATION FOR SEQ ID NO: 16:

(i) SEQUENCE CHARACTERISTICS:
        (A) LENGTH: 11 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 11
        (D) OTHER INFORMATION: /product= "OTHER"
            /note= "Xaa = Lys linked to
            biotin-streptavidin"

(xi) SEQUENCE DESCRIPTION: SEQ ID NO: 16:

Tyr Gly Gly Phe Leu Gly Gly Gly Gly Ser Xaa
1               5                   10

(2) INFORMATION FOR SEQ ID NO: 17:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 17:

TGAGCCGGCA CTCCCGGCCA A                                           21

(2) INFORMATION FOR SEQ ID NO: 18:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 18:

ACGCTGACCC GTGGCGGAGC A                                        21

(2) INFORMATION FOR SEQ ID NO: 19:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 19:

TTACGGGCTA GCCATAGGGC AGAAGACGCT GACCCGTGGC GGAGCA              46

(2) INFORMATION FOR SEQ ID NO: 20:

(i) SEQUENCE CHARACTERISTICS:
        (A) LENGTH: 83 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 20:

TGAGCCGGCA CTCCCGGCCA ATTGTTTCAC AGCGTTATGC TCCGCCACGG GTCAGCGTCT      60

TCTGCCCTAT GGCTAGCCCG TAA                                      83

(2) INFORMATION FOR SEQ ID NO: 21:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 21:

TTACGGGCTA GCCATAGGGC A                                        21

(2) INFORMATION FOR SEQ ID NO: 22:

(i) SEQUENCE CHARACTERISTICS:
        (A) LENGTH: 22 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 22:

Met Ala Leu Pro Val Thr Ala Leu Leu Leu Pro Leu Ala Leu Leu Le
1              5                    10                    15

His Ala Ala Arg Pro Asp
          20

(2) INFORMATION FOR SEQ ID NO: 23:

(i) SEQUENCE CHARACTERISTICS:
        (A) LENGTH: 11 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /note= "Xaa = phosphotyrosine"

(ix) FEATURE:
        (A) NAME/KEY: Modified-site
        (B) LOCATION: 11
        (D) OTHER INFORMATION: /product= "OTHER"
            /note= "Xaa = Lys linked to
            biotin-streptavidin"

(xi) SEQUENCE DESCRIPTION: SEQ ID NO: 23:

Xaa Gly Gly Phe Leu Gly Gly Gly Gly Ser Xaa
1               5                   10

(2) INFORMATION FOR SEQ ID NO: 24:

(i) SEQUENCE CHARACTERISTICS:
        (A) LENGTH: 5 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /note= "Xaa = phosphotyrosine"

(xi) SEQUENCE DESCRIPTION: SEQ ID NO: 24:

Xaa Gly Gly Phe Leu
1               5

(2) INFORMATION FOR SEQ ID NO: 25:

(i) SEQUENCE CHARACTERISTICS:
        (A) LENGTH: 5 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /note= "Xaa = phosphotyrosine"

(ix) FEATURE:
        (A) NAME/KEY: Modified-site
        (B) LOCATION: 5
        (D) OTHER INFORMATION: /product= "OTHER"
            /note= "Xaa = Leu linked to
            linker-biotin"

(xi) SEQUENCE DESCRIPTION: SEQ ID NO: 25:

Xaa Gly Gly Phe Xaa
1               5

(2) INFORMATION FOR SEQ ID NO: 26:

(i) SEQUENCE CHARACTERISTICS:
        (A) LENGTH: 5 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /note= "Xaa = phosphotyrosine"

(ix) FEATURE:
        (A) NAME/KEY: Modified-site
        (B) LOCATION: 5
        (D) OTHER INFORMATION: /product= "OTHER"
            /note= "Xaa = Leu linked to biotin"

(xi) SEQUENCE DESCRIPTION: SEQ ID NO: 26:

Xaa Gly Gly Phe Xaa
1               5

(2) INFORMATION FOR SEQ ID NO: 27:

(i) SEQUENCE CHARACTERISTICS:
        (A) LENGTH: 15 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /note= "Xaa = acetyl-glycine"

(ix) FEATURE:
        (A) NAME/KEY: Modified-site
        (B) LOCATION: 15
        (D) OTHER INFORMATION: /product= "OTHER"
            /note= "Xaa = Lys linked to biotin"

(xi) SEQUENCE DESCRIPTION: SEQ ID NO: 27:

Xaa Ile Tyr Arg Tyr Gly Gly Phe Leu Gly Gly Gly Ser Xaa
1               5                   10                  15

(2) INFORMATION FOR SEQ ID NO: 28:

(i) SEQUENCE CHARACTERISTICS:
        (A) LENGTH: 19 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /note= "Xaa = Gly linked to maltose
            binding protein (MBP)"

(xi) SEQUENCE DESCRIPTION: SEQ ID NO: 28:

Xaa Gly Gly Gly Ser Asp Asn Thr Ala Trp Tyr Glu Arg Phe Leu Le
1               5                   10                  15

Gln Tyr Asn (2) INFORMATION FOR SEQ ID NO: 29:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 10
        (D) OTHER INFORMATION: /product= "OTHER"
            /note= "Xaa = tyrosinamide"

(xi) SEQUENCE DESCRIPTION: SEQ ID NO: 29:

```
Tyr Glu Trp Thr Pro Gly Tyr Tyr Gln Xaa
1               5                   10
```

(2) INFORMATION FOR SEQ ID NO: 30:

(i) SEQUENCE CHARACTERISTICS:
        (A) LENGTH: 23 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 13
        (D) OTHER INFORMATION: /product= "OTHER"
            /note= "Xaa = Lys linked to biotin"

(ix) FEATURE:
        (A) NAME/KEY: Modified-site
        (B) LOCATION: 23
        (D) OTHER INFORMATION: /product= "OTHER"
            /note= "Xaa = Ser linked to maltose
            binding protein (MBP) linked to peptide
            AF12413"

(xi) SEQUENCE DESCRIPTION: SEQ ID NO: 30:

```
Met Ala Gly Gly Leu Asn Asp Ile Phe Glu Ala Gln Xaa Ile Glu Tr
1               5                   10                  15

His Glu Asp Thr Gly Gly Xaa
            20
```

(2) INFORMATION FOR SEQ ID NO: 31:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /note= "Xaa = Asp linked to maltose
            binding protein linked to
            SEQ ID NO:30"

(xi) SEQUENCE DESCRIPTION: SEQ ID NO: 31:

```
Xaa Asn Thr Ala Trp Tyr Glu Arg Phe Leu Leu Gln Tyr Asn
1               5                   10
```